(12) United States Patent
Bergheim et al.

(10) Patent No.: US 9,675,426 B2
(45) Date of Patent: Jun. 13, 2017

(54) APPARATUS, METHODS, AND COMPOSITIONS FOR ENDODONTIC TREATMENTS

(75) Inventors: Bjarne Bergheim, Mission Viejo, CA (US); Mehrzad Khakpour, Laguna Beach, CA (US); Michele Pham, Anaheim, CA (US); Morteza Gharib, Altadena, CA (US); Richard S. Tebbs, Aliso Viejo, CA (US)

(73) Assignee: SONENDO, INC., Laguna Hills, CA (US)

( * ) Notice: Subject to any disclaimer, the term of this patent is extended or adjusted under 35 U.S.C. 154(b) by 0 days.

(21) Appl. No.: 13/279,199

(22) Filed: Oct. 21, 2011

(65) Prior Publication Data
US 2012/0237893 A1 Sep. 20, 2012

Related U.S. Application Data

(60) Provisional application No. 61/405,616, filed on Oct. 21, 2010, provisional application No. 61/485,089, filed on May 11, 2011.

(51) Int. Cl.
*A61C 5/02* (2006.01)
*A61C 5/04* (2006.01)
*A61C 17/20* (2006.01)
(52) U.S. Cl.
CPC .................. *A61C 5/02* (2013.01); *A61C 5/04* (2013.01); *A61C 17/20* (2013.01)
(58) Field of Classification Search
CPC ......... A61C 5/02; A61C 17/02–17/028; A61C 17/0208
(Continued)

(56) References Cited

U.S. PATENT DOCUMENTS 1,500,107 A 7/1924 Chandler
2,108,558 A 2/1938 Jackman
(Continued)

FOREIGN PATENT DOCUMENTS

AU 2012-202315 A1 4/2012
AU 2007140780 5/2014
(Continued)

OTHER PUBLICATIONS

European Extended Search Report received in European Patent Application No. 09743801.4, dated Jun. 4, 2012; in 5 pages.
(Continued)

*Primary Examiner* — Matthew Nelson
(74) *Attorney, Agent, or Firm* — Knobbe, Martens, Olson & Bear LLP

(57) ABSTRACT

Examples of apparatus, methods, and compositions for endodontic treatments are described. The apparatus can include a fluid platform configured to substantially retain fluid in a tooth chamber during treatment. The fluid platform can help maintain fluid circulation in the tooth chamber as fluid flows into and out of the tooth chamber. The apparatus can also include a pressure wave generator configured to generate acoustic waves that can be used for cleaning root canals and tooth surfaces in the tooth chamber. Examples of pressure wave generators include a liquid jet, an electromagnetic energy delivery device, and an ultrasonic device. The fluid can include antiseptic or antibacterial solutions to assist in tooth cleaning. The fluid may be degassed to have a reduced dissolved gas content (compared to non-degassed fluids used in endodontic treatments), which may improve the effectiveness of the pressure wave generation or the cleaning.

71 Claims, 33 Drawing Sheets

(58) Field of Classification Search
USPC ............... 433/80, 81, 91, 92, 94, 95, 224; 134/104.2
See application file for complete search history.

(56) References Cited

U.S. PATENT DOCUMENTS

| | | | |
|---|---|---|---|
| 3,023,306 A | 2/1962 | Kester | |
| 3,401,690 A | 9/1968 | Martin | |
| 3,460,255 A * | 8/1969 | Hutson | 433/91 |
| 3,514,328 A | 5/1970 | Malin | |
| 3,521,359 A | 7/1970 | Harris | |
| 3,522,801 A | 8/1970 | Seymour | |
| 3,547,110 A | 12/1970 | Balamuth | |
| 3,561,433 A | 2/1971 | Kovach | |
| 3,590,813 A | 7/1971 | Roszyk | |
| 3,624,907 A | 12/1971 | Brass et al. | |
| 3,703,170 A | 11/1972 | Ryckman, Jr. | |
| 3,756,225 A | 9/1973 | Moret et al. | |
| 3,828,770 A | 8/1974 | Kuris et al. | |
| 3,921,296 A | 11/1975 | Harris | |
| 3,930,505 A | 1/1976 | Wallach | |
| 3,962,790 A | 6/1976 | Riitano et al. | |
| 4,021,921 A | 5/1977 | Detaille | |
| 4,060,600 A | 11/1977 | Vit | |
| 4,215,476 A | 8/1980 | Armstrong | |
| 4,247,288 A | 1/1981 | Yoshii et al. | |
| 4,274,555 A | 6/1981 | Sneider | |
| 4,276,880 A | 7/1981 | Malmin | |
| 4,293,188 A | 10/1981 | McMahon | |
| 4,376,835 A | 3/1983 | Schmitt et al. | |
| 4,386,911 A | 6/1983 | Maloney et al. | |
| 4,424,036 A | 1/1984 | Lokken | |
| 4,474,251 A | 10/1984 | Johnson, Jr. | |
| 4,492,575 A | 1/1985 | Mabille | |
| 4,534,542 A * | 8/1985 | Russo | A61M 1/0047 137/843 |
| 4,539,987 A | 9/1985 | Nath et al. | |
| 4,608,017 A | 8/1986 | Sadohara | |
| 4,659,218 A | 4/1987 | de Lasa et al. | |
| 4,676,749 A | 6/1987 | Mabille | |
| 4,684,781 A | 8/1987 | Frish et al. | |
| 4,789,335 A | 12/1988 | Geller et al. | |
| 4,872,837 A | 10/1989 | Issalene et al. | |
| 4,941,459 A | 7/1990 | Mathur | |
| 4,957,436 A | 9/1990 | Ryder | |
| 4,973,246 A | 11/1990 | Black et al. | |
| 4,985,027 A | 1/1991 | Dressel | |
| 4,993,947 A * | 2/1991 | Grosrey | A61C 17/0208 433/224 |
| 5,013,300 A * | 5/1991 | Williams | A61M 1/008 433/91 |
| 5,029,576 A | 7/1991 | Evans, Sr. | |
| 5,037,431 A | 8/1991 | Summers et al. | |
| 5,046,950 A | 9/1991 | Favonio | |
| 5,055,048 A | 10/1991 | Vassiliadis et al. | |
| 5,094,256 A | 3/1992 | Barth | |
| 5,112,224 A | 5/1992 | Shirota | |
| 5,188,532 A | 2/1993 | Levy | |
| 5,188,634 A | 2/1993 | Hussein et al. | |
| 5,194,723 A | 3/1993 | Cates et al. | |
| 5,195,952 A * | 3/1993 | Solnit | A61C 17/043 433/91 |
| 5,224,942 A | 7/1993 | Beuchat et al. | |
| 5,267,856 A | 12/1993 | Wolbarsht et al. | |
| 5,267,995 A | 12/1993 | Doiron et al. | |
| 5,269,777 A | 12/1993 | Doiron et al. | |
| 5,295,828 A | 3/1994 | Grosrey | |
| 5,307,839 A | 5/1994 | Loebker et al. | |
| 5,322,504 A | 6/1994 | Doherty et al. | |
| 5,326,263 A | 7/1994 | Weissman | |
| 5,334,019 A | 8/1994 | Goldsmith et al. | |
| 5,380,201 A | 1/1995 | Kawata | |
| 5,387,376 A | 2/1995 | Gasser | |
| D356,866 S | 3/1995 | Meller | |
| 5,399,089 A | 3/1995 | Eichman et al. | |
| 5,428,699 A | 6/1995 | Pon | |
| 5,435,724 A | 7/1995 | Goodman et al. | |
| 5,474,451 A | 12/1995 | Dalrymple et al. | |
| 5,490,779 A | 2/1996 | Malmin | |
| 5,503,559 A | 4/1996 | Vari | |
| 5,540,587 A | 7/1996 | Malmin | |
| 5,547,376 A | 8/1996 | Harrel | |
| 5,554,896 A | 9/1996 | Hogan | |
| 5,562,692 A | 10/1996 | Bair | |
| 5,564,929 A | 10/1996 | Alpert | |
| 5,570,182 A | 10/1996 | Nathel et al. | |
| 5,591,184 A | 1/1997 | McDonnell et al. | |
| 5,601,430 A | 2/1997 | Kutsch et al. | |
| 5,620,414 A | 4/1997 | Campbell, Jr. | |
| 5,643,299 A | 7/1997 | Bair | |
| 5,660,817 A | 8/1997 | Masterman et al. | |
| 5,674,226 A | 10/1997 | Doherty et al. | |
| 5,720,894 A | 2/1998 | Neev et al. | |
| 5,730,727 A * | 3/1998 | Russo | A61M 1/0047 137/517 |
| 5,735,815 A | 4/1998 | Bair | |
| 5,740,291 A | 4/1998 | De Lasa et al. | |
| 5,755,752 A | 5/1998 | Segal | |
| 5,759,159 A | 6/1998 | Masreliez | |
| 5,795,153 A | 8/1998 | Rechmann | |
| 5,797,745 A | 8/1998 | Ruddle | |
| 5,810,037 A | 9/1998 | Sasaki et al. | |
| 5,816,807 A | 10/1998 | Matsutani et al. | |
| 5,820,373 A | 10/1998 | Okano et al. | |
| 5,825,958 A | 10/1998 | Gollihar et al. | |
| 5,839,896 A | 11/1998 | Hickok et al. | |
| 5,842,863 A | 12/1998 | Bruns et al. | |
| 5,846,080 A | 12/1998 | Schneider | |
| 5,853,384 A | 12/1998 | Bair | |
| 5,865,790 A | 2/1999 | Bair | |
| 5,868,570 A | 2/1999 | Hickok et al. | |
| 5,874,677 A | 2/1999 | Bab et al. | |
| 5,879,160 A | 3/1999 | Ruddle | |
| 5,915,965 A | 6/1999 | Ohlsson et al. | |
| 5,921,775 A | 7/1999 | Buchanan | |
| 5,968,039 A | 10/1999 | Deutsch | |
| 5,975,897 A * | 11/1999 | Propp | A61C 17/043 433/91 |
| 5,989,023 A | 11/1999 | Summer et al. | |
| 6,004,319 A | 12/1999 | Goble et al. | |
| 6,053,735 A | 4/2000 | Buchanan | |
| 6,079,979 A | 6/2000 | Riitano | |
| 6,122,300 A | 9/2000 | Freiberg et al. | |
| 6,129,721 A | 10/2000 | Kataoka et al. | |
| 6,139,319 A | 10/2000 | Sauer et al. | |
| 6,143,011 A | 11/2000 | Hood et al. | |
| 6,159,006 A | 12/2000 | Cook et al. | |
| 6,162,052 A | 12/2000 | Kokubu | |
| 6,162,177 A | 12/2000 | Bab et al. | |
| 6,162,202 A | 12/2000 | Sicurelli et al. | |
| 6,164,966 A | 12/2000 | Turdiu et al. | |
| 6,179,617 B1 | 1/2001 | Ruddle | |
| 6,190,318 B1 | 2/2001 | Bab et al. | |
| 6,221,031 B1 | 4/2001 | Heraud | |
| 6,224,378 B1 * | 5/2001 | Valdes | A61C 1/0084 433/224 |
| 6,227,855 B1 | 5/2001 | Hickok et al. | |
| 6,245,032 B1 | 6/2001 | Sauer et al. | |
| 6,282,013 B1 | 8/2001 | Ostler et al. | |
| 6,288,499 B1 | 9/2001 | Rizoiu et al. | |
| 6,290,502 B1 | 9/2001 | Hugo | |
| 6,312,440 B1 | 11/2001 | Hood et al. | |
| 6,315,557 B1 | 11/2001 | Messick | |
| 6,343,929 B1 | 2/2002 | Fischer | |
| 6,386,871 B1 | 5/2002 | Rossell | |
| 6,390,815 B1 | 5/2002 | Pond | |
| 6,428,319 B1 | 8/2002 | Lopez et al. | |
| 6,440,103 B1 | 8/2002 | Hood et al. | |
| 6,454,566 B1 | 9/2002 | Lynch et al. | |
| 6,464,498 B1 | 10/2002 | Pond | |
| 6,485,304 B2 | 11/2002 | Beerstecher et al. | |
| 6,497,572 B2 * | 12/2002 | Hood et al. | 433/81 |
| 6,511,493 B1 | 1/2003 | Moutafis et al. | |
| 6,514,077 B1 | 2/2003 | Wilk | |

(56) References Cited

U.S. PATENT DOCUMENTS

| | | |
|---|---|---|
| 6,527,766 B1 | 3/2003 | Bair |
| 6,538,739 B1 | 3/2003 | Visuri et al. |
| 6,562,050 B1 | 5/2003 | Owen |
| 6,572,709 B1 | 6/2003 | Kaneda et al. |
| 6,602,074 B1 | 8/2003 | Suh et al. |
| 6,616,447 B1 | 9/2003 | Rizoiu et al. |
| 6,638,219 B1 | 10/2003 | Asch et al. |
| 6,641,394 B2 | 11/2003 | Garman |
| 6,663,386 B1 | 12/2003 | Moelsgaard |
| 6,676,409 B2 | 1/2004 | Grant |
| 6,783,364 B1 | 8/2004 | Juan |
| 6,817,862 B2 | 11/2004 | Hickok |
| D499,486 S | 12/2004 | Kuhn et al. |
| 6,881,061 B2 | 4/2005 | Fisher |
| 6,910,887 B2 | 6/2005 | Van Den Houdt |
| 6,948,935 B2 | 9/2005 | Nusstein |
| 6,971,878 B2 | 12/2005 | Pond |
| 6,976,844 B2 | 12/2005 | Hickok et al. |
| 6,981,869 B2 | 1/2006 | Ruddle |
| 6,997,714 B1 | 2/2006 | Schoeffel |
| 7,011,521 B2 | 3/2006 | Sierro et al. |
| 7,011,644 B1 | 3/2006 | Andrew et al. |
| 7,044,737 B2 | 5/2006 | Fu |
| 7,108,693 B2 | 9/2006 | Rizoiu et al. |
| 7,115,100 B2 | 10/2006 | McRury et al. |
| 7,147,468 B2 | 12/2006 | Snyder et al. |
| 7,163,400 B2 | 1/2007 | Cozean et al. |
| 7,238,342 B2 | 7/2007 | Torabinejad et al. |
| 7,261,561 B2 | 8/2007 | Ruddle et al. |
| 7,269,306 B1 | 9/2007 | Koeneman et al. |
| 7,270,544 B2 * | 9/2007 | Schemmer .............. A61C 5/02 433/221 |
| 7,296,318 B2 | 11/2007 | Mourad et al. |
| 7,306,459 B1 | 12/2007 | Williams et al. |
| 7,306,577 B2 * | 12/2007 | Lemoine .............. A61C 17/043 604/118 |
| 7,326,054 B2 | 2/2008 | Todd et al. |
| 7,356,225 B2 | 4/2008 | Loebel |
| 7,384,419 B2 | 6/2008 | Jones et al. |
| 7,415,050 B2 | 8/2008 | Rizoiu et al. |
| 7,445,618 B2 | 11/2008 | Eggers et al. |
| 7,470,124 B2 | 12/2008 | Bornstein |
| 7,549,861 B2 | 6/2009 | Ruddle et al. |
| 7,620,290 B2 | 11/2009 | Rizoiu et al. |
| 7,630,420 B2 | 12/2009 | Boutoussov |
| 7,641,668 B2 | 1/2010 | Perry et al. |
| 7,670,141 B2 | 3/2010 | Thomas et al. |
| 7,696,466 B2 | 4/2010 | Rizoiu et al. |
| 7,748,979 B2 | 7/2010 | Nahlieli |
| 7,833,016 B2 | 11/2010 | Gharib et al. |
| 7,845,944 B2 * | 12/2010 | DiGasbarro ......... A61C 17/043 433/91 |
| 7,901,373 B2 | 3/2011 | Tavger |
| 7,909,817 B2 | 3/2011 | Griffin et al. |
| 7,916,282 B2 | 3/2011 | Duineveld et al. |
| 7,959,441 B2 | 6/2011 | Glover et al. |
| 7,980,854 B2 | 7/2011 | Glover et al. |
| 7,980,923 B2 | 7/2011 | Olmo et al. |
| 8,002,544 B2 | 8/2011 | Rizoiu et al. |
| 8,047,841 B2 | 11/2011 | Jefferies |
| 8,128,401 B2 | 3/2012 | Ruddle et al. |
| 8,204,612 B2 | 6/2012 | Feine et al. |
| D669,180 S | 10/2012 | Takashi et al. |
| 8,295,025 B2 | 10/2012 | Edel et al. |
| 8,298,215 B2 | 10/2012 | Zinn |
| 8,317,514 B2 | 11/2012 | Weill |
| 8,322,910 B2 | 12/2012 | Gansmuller et al. |
| 8,439,676 B2 | 5/2013 | Florman |
| 8,506,293 B2 | 8/2013 | Pond |
| 8,617,090 B2 | 12/2013 | Fougere et al. |
| 8,672,678 B2 | 3/2014 | Gramann et al. |
| 8,684,956 B2 | 4/2014 | McDonough et al. |
| 8,740,957 B2 | 6/2014 | Masotti |
| 8,747,005 B2 | 6/2014 | Kemp et al. |
| 8,753,121 B2 | 6/2014 | Gharib et al. |
| 8,758,010 B2 | 6/2014 | Yamanaka et al. |
| 8,801,316 B1 | 8/2014 | Abedini |
| 8,977,085 B2 | 3/2015 | Walsh et al. |
| D726,324 S | 4/2015 | Duncan et al. |
| 9,022,959 B2 | 5/2015 | Fusi, II et al. |
| 9,022,961 B2 | 5/2015 | Fougere et al. |
| 9,050,157 B2 | 6/2015 | Boyd et al. |
| 9,084,651 B2 | 7/2015 | Laufer |
| 9,101,377 B2 | 8/2015 | Boutoussov et al. |
| D745,966 S | 12/2015 | Piorek et al. |
| 9,216,073 B2 | 12/2015 | McDonough et al. |
| 9,308,326 B2 | 4/2016 | Hunter et al. |
| 9,333,060 B2 | 5/2016 | Hunter |
| 9,341,184 B2 | 5/2016 | Dion et al. |
| 2002/0012897 A1 | 1/2002 | Tingley et al. |
| 2002/0072032 A1 | 6/2002 | Senn et al. |
| 2002/0108614 A1 * | 8/2002 | Schultz ............... A61M 1/0047 128/207.14 |
| 2003/0096213 A1 | 5/2003 | Hickok et al. |
| 2003/0121532 A1 | 7/2003 | Coughlin et al. |
| 2003/0191429 A1 | 10/2003 | Andrew et al. |
| 2003/0207231 A1 | 11/2003 | Nance |
| 2003/0207232 A1 | 11/2003 | Todd et al. |
| 2003/0236517 A1 | 12/2003 | Appling |
| 2004/0048226 A1 | 3/2004 | Garman |
| 2004/0063074 A1 | 4/2004 | Fisher |
| 2004/0072122 A1 | 4/2004 | Hegemann |
| 2004/0073374 A1 | 4/2004 | Lockhart et al. |
| 2004/0101809 A1 | 5/2004 | Weiss et al. |
| 2004/0126732 A1 | 7/2004 | Nusstein |
| 2004/0127892 A1 | 7/2004 | Harris |
| 2005/0064371 A1 | 3/2005 | Soukos et al. |
| 2005/0096529 A1 | 5/2005 | Cooper et al. |
| 2005/0136375 A1 | 6/2005 | Sicurelli, Jr. et al. |
| 2005/0155622 A1 | 7/2005 | Leis |
| 2005/0170312 A1 | 8/2005 | Pond |
| 2005/0199261 A1 | 9/2005 | Vanhauwemeiren et al. |
| 2005/0271531 A1 | 12/2005 | Brown et al. |
| 2005/0277898 A1 | 12/2005 | Dimalanta et al. |
| 2006/0019220 A1 | 1/2006 | Loebel et al. |
| 2006/0021642 A1 | 2/2006 | Sliwa et al. |
| 2006/0036172 A1 | 2/2006 | Abe |
| 2006/0064037 A1 | 3/2006 | Shalon et al. |
| 2006/0184071 A1 | 8/2006 | Klopotek |
| 2006/0189965 A1 | 8/2006 | Litvak et al. |
| 2006/0234182 A1 | 10/2006 | Ruddle et al. |
| 2006/0234183 A1 | 10/2006 | Ruddle et al. |
| 2006/0246395 A1 | 11/2006 | Pond |
| 2006/0257819 A1 | 11/2006 | Johnson |
| 2006/0264808 A1 | 11/2006 | Staid et al. |
| 2007/0009449 A1 | 1/2007 | Kanca |
| 2007/0020576 A1 | 1/2007 | Osborn et al. |
| 2007/0042316 A1 | 2/2007 | Pichat et al. |
| 2007/0049911 A1 | 3/2007 | Brown |
| 2007/0072153 A1 | 3/2007 | Gross et al. |
| 2007/0083120 A1 | 4/2007 | Cain et al. |
| 2007/0148615 A1 | 6/2007 | Pond |
| 2007/0175502 A1 | 8/2007 | Sliwa |
| 2007/0179486 A1 | 8/2007 | Welch et al. |
| 2007/0248932 A1 * | 10/2007 | Gharib .................. A61C 5/02 433/81 |
| 2007/0287125 A1 * | 12/2007 | Weill .................... A61C 5/02 433/81 |
| 2008/0014545 A1 | 1/2008 | Schippers |
| 2008/0032259 A1 | 2/2008 | Schoeffel |
| 2008/0044789 A1 | 2/2008 | Johnson |
| 2008/0050702 A1 | 2/2008 | Glover et al. |
| 2008/0070195 A1 | 3/2008 | DiVito et al. |
| 2008/0085490 A1 | 4/2008 | Jabri |
| 2008/0138761 A1 | 6/2008 | Pond |
| 2008/0155770 A1 * | 7/2008 | Grez ......................... 15/22.1 |
| 2008/0159345 A1 | 7/2008 | Bornstein |
| 2008/0160479 A1 | 7/2008 | Ruddle et al. |
| 2008/0160480 A1 | 7/2008 | Ruddle et al. |
| 2008/0188848 A1 | 8/2008 | Deutmeyer et al. |
| 2008/0199831 A1 | 8/2008 | Teichert et al. |
| 2008/0255498 A1 | 10/2008 | Houle |
| 2008/0311540 A1 | 12/2008 | Gottenbos et al. |
| 2009/0004621 A1 | 1/2009 | Quan et al. |

(56) References Cited

U.S. PATENT DOCUMENTS

| | | |
|---|---|---|
| 2009/0011380 A1 | 1/2009 | Wang |
| 2009/0047624 A1 | 2/2009 | Tsai |
| 2009/0047634 A1 | 2/2009 | Calvert |
| 2009/0054881 A1 | 2/2009 | Krespi |
| 2009/0111068 A1* | 4/2009 | Martinez ............ A61C 17/0208 433/81 |
| 2009/0111069 A1* | 4/2009 | Wagner ................ A61B 17/244 433/95 |
| 2009/0130622 A1 | 5/2009 | Bollinger et al. |
| 2009/0208898 A1 | 8/2009 | Kaplan |
| 2009/0211042 A1 | 8/2009 | Bock |
| 2009/0220908 A1 | 9/2009 | Divito et al. |
| 2009/0227185 A1 | 9/2009 | Summers et al. |
| 2009/0263759 A1 | 10/2009 | Van Herpern |
| 2010/0047734 A1 | 2/2010 | Harris et al. |
| 2010/0092922 A1 | 4/2010 | Ruddle |
| 2010/0143861 A1 | 6/2010 | Gharib |
| 2010/0152634 A1 | 6/2010 | Dove |
| 2010/0160838 A1 | 6/2010 | Krespi |
| 2010/0229316 A1 | 9/2010 | Hohlbein et al. |
| 2010/0273125 A1 | 10/2010 | Janssen et al. |
| 2010/0330539 A1 | 12/2010 | Glover et al. |
| 2011/0027746 A1 | 2/2011 | McDonough et al. |
| 2011/0027747 A1 | 2/2011 | Fougere et al. |
| 2011/0072605 A1 | 3/2011 | Steur |
| 2011/0087605 A1 | 4/2011 | Pond |
| 2011/0111365 A1 | 5/2011 | Gharib et al. |
| 2011/0117517 A1 | 5/2011 | Bergheim et al. |
| 2011/0143310 A1 | 6/2011 | Hunter |
| 2011/0229845 A1 | 9/2011 | Chen |
| 2011/0256503 A1 | 10/2011 | Fraser |
| 2011/0269099 A1 | 11/2011 | Glover et al. |
| 2011/0281231 A1 | 11/2011 | Rizoiu et al. |
| 2012/0135373 A1 | 5/2012 | Cheng et al. |
| 2012/0141953 A1 | 6/2012 | Mueller |
| 2012/0148979 A1 | 6/2012 | Ruddle |
| 2012/0276497 A1 | 11/2012 | Gharib |
| 2012/0282570 A1 | 11/2012 | Mueller |
| 2013/0040267 A1 | 2/2013 | Bergheim |
| 2013/0084544 A1 | 4/2013 | Boutoussov et al. |
| 2013/0084545 A1 | 4/2013 | Netchitailo et al. |
| 2013/0143180 A1 | 6/2013 | Glover et al. |
| 2013/0177865 A1 | 7/2013 | Ostler |
| 2013/0216980 A1 | 8/2013 | Boronkay et al. |
| 2013/0236857 A1 | 9/2013 | Boutoussov et al. |
| 2013/0288195 A1 | 10/2013 | Mueller |
| 2013/0296910 A1 | 11/2013 | Deng |
| 2013/0330684 A1 | 12/2013 | Dillon et al. |
| 2013/0337404 A1 | 12/2013 | Feine |
| 2014/0032183 A1 | 1/2014 | Fisker et al. |
| 2014/0072931 A1 | 3/2014 | Fougere et al. |
| 2014/0087333 A1 | 3/2014 | DiVito et al. |
| 2014/0099597 A1 | 4/2014 | Bergheim |
| 2014/0113243 A1 | 4/2014 | Boutoussov et al. |
| 2014/0124969 A1 | 5/2014 | Blaisdell et al. |
| 2014/0127641 A1 | 5/2014 | Hilscher et al. |
| 2014/0170588 A1 | 6/2014 | Miller et al. |
| 2014/0220505 A1 | 8/2014 | Khakpour |
| 2014/0220511 A1 | 8/2014 | DiVito et al. |
| 2014/0242551 A1 | 8/2014 | Downs |
| 2014/0261534 A1 | 9/2014 | Schepis |
| 2014/0272782 A1 | 9/2014 | Luettgen et al. |
| 2014/0349246 A1 | 11/2014 | Johnson et al. |
| 2015/0010878 A1 | 1/2015 | Seibel et al. |
| 2015/0010882 A1 | 1/2015 | Bergheim |
| 2015/0044631 A1 | 2/2015 | Lifshitz et al. |
| 2015/0044632 A1 | 2/2015 | Bergheim et al. |
| 2015/0056567 A1 | 2/2015 | Fregoso et al. |
| 2015/0056570 A1 | 2/2015 | Kansal |
| 2015/0125811 A1 | 5/2015 | Lifshitz et al. |
| 2015/0132712 A1 | 5/2015 | Gharib |
| 2015/0140503 A1 | 5/2015 | Bergheim et al. |
| 2015/0147715 A1 | 5/2015 | Breysse |
| 2015/0147717 A1 | 5/2015 | Taylor et al. |
| 2015/0147718 A1 | 5/2015 | Khakpour |
| 2015/0150650 A1 | 6/2015 | Netchitailo et al. |
| 2015/0173850 A1 | 6/2015 | Garrigues et al. |
| 2015/0173852 A1 | 6/2015 | Khakpour |
| 2015/0190597 A1 | 7/2015 | Zachar et al. |
| 2015/0216597 A1 | 8/2015 | Boutoussov et al. |
| 2015/0230865 A1 | 8/2015 | Sivriver et al. |
| 2015/0268803 A1 | 9/2015 | Patton et al. |
| 2015/0277738 A1 | 10/2015 | Boutoussov et al. |
| 2015/0283277 A1 | 10/2015 | Schafer et al. |
| 2015/0327964 A1 | 11/2015 | Bock |
| 2015/0335410 A1 | 11/2015 | Zhao |
| 2015/0366634 A1 | 12/2015 | Gharib |
| 2015/0374471 A1 | 12/2015 | Stangel et al. |
| 2016/0022392 A1 | 1/2016 | Chang et al. |
| 2016/0095679 A1 | 4/2016 | Khakpour |
| 2016/0100921 A1 | 4/2016 | Ungar |
| 2016/0113733 A1 | 4/2016 | Pond et al. |
| 2016/0128815 A1 | 5/2016 | Birdee et al. |
| 2016/0135581 A1 | 5/2016 | Pai |

FOREIGN PATENT DOCUMENTS

| | | |
|---|---|---|
| AU | 2011316839 | 8/2015 |
| CA | 2361482 | 6/2002 |
| CN | 102724929 | 10/2012 |
| CN | 103027762 A | 4/2013 |
| CN | 104470464 A | 3/2015 |
| DE | 37 08 801 A1 | 9/1988 |
| DE | 102 48 336 | 5/2004 |
| DE | 103 31 583 | 7/2004 |
| EP | 1 214 916 | 6/2002 |
| EP | 0 902 654 | 8/2004 |
| EP | 2 498 713 | 9/2012 |
| EP | 2 821 027 | 1/2015 |
| EP | 2 836 156 | 2/2015 |
| EP | 2 836 157 | 2/2015 |
| EP | 2 934 364 | 10/2015 |
| EP | 2 951 019 | 12/2015 |
| EP | 3 013 277 | 5/2016 |
| FR | 1 225 547 | 7/1960 |
| FR | 2 831 050 | 10/2001 |
| GB | 917 633 | 2/1963 |
| IL | 219169 | 4/2012 |
| IN | 8681/DELNP/2010 | 3/2012 |
| JP | 09-276292 | 10/1997 |
| JP | 11-113927 A | 4/1999 |
| JP | 11-244303 A | 9/1999 |
| JP | 2000-254153 A | 9/2000 |
| JP | 2002-209911 | 7/2002 |
| JP | 2004-313659 | 11/2003 |
| JP | 3535685 B2 | 6/2004 |
| JP | 2005-095374 | 4/2005 |
| JP | 2008-93080 | 4/2008 |
| JP | 2008-132099 | 6/2008 |
| JP | 2009-114953 | 5/2009 |
| JP | 2015-510829 | 4/2015 |
| JP | 5902096 | 3/2016 |
| KR | 10-2008-0105713 A | 12/2008 |
| KR | 10-2012-0084897 A | 7/2012 |
| KR | 10-2013-0141103 A | 12/2013 |
| KR | 2004-72508 Y1 | 5/2014 |
| RU | 2326611 C1 | 12/2011 |
| WO | WO 92/04871 | 4/1992 |
| WO | WO 92/12685 | 8/1992 |
| WO | WO 98/25536 | 6/1995 |
| WO | WO 00/45731 | 8/2000 |
| WO | WO 01/93773 | 12/2001 |
| WO | WO 02/078644 | 10/2002 |
| WO | WO 03/086223 | 10/2003 |
| WO | WO 2004/034923 | 4/2004 |
| WO | WO 2004/082501 | 9/2004 |
| WO | WO 2005/007008 | 1/2005 |
| WO | WO 2005/032393 | 4/2005 |
| WO | WO 2006/082101 | 8/2006 |
| WO | WO 2007/124038 | 11/2007 |
| WO | WO 2008/024442 | 2/2008 |
| WO | WO 2008/092125 | 7/2008 |
| WO | WO 2008/120018 | 10/2008 |
| WO | WO 2009/064947 | 5/2009 |

(56) References Cited

FOREIGN PATENT DOCUMENTS

| WO | WO 2009/137815 | 11/2009 |
|----|----------------|---------|
| WO | WO 2010/099538 | 9/2010 |
| WO | WO 2011/060327 | 5/2011 |
| WO | WO 2012/054905 | 4/2012 |
| WO | WO 2013/015700 | 1/2013 |
| WO | WO 2013/061251 | 5/2013 |
| WO | WO 2013/142385 | 9/2013 |
| WO | WO 2013/155492 | 10/2013 |
| WO | WO 2014/100751 | 6/2014 |
| WO | WO 2014/121293 | 8/2014 |
| WO | WO 2015/168329 | 11/2015 |
| WO | WO 2016/005221 | 1/2016 |

OTHER PUBLICATIONS

Adachi et al; Jet Structure Analyses on High-Speed Submerged Water Jets through Cavitation 110 Noises; pp. 568-574; The Japan Society of Mechanical Engineers International Journal-Series B, vol. 39, No. 3; Nov. 1996.
Al-Jadaa et al; Acoustic Hypochlorite Activation in Simulated Curved Canals; pp. 1408-1411; Journal of Endodontics, vol. 35, No. 10; Oct. 2009.
Anand et al; Prevention of Nozzle Wear in High-Speed Slurry Jets Using Porous Lubricated Nozzles; pp. 1-13; Department of Mechanical Engineering, The Johns Hopkins University, Oct. 2000.
Anantharamaiah et al; A simple expression for predicting the inlet roundness of micro-nozzles; pp. N31-N39; Journal of Micromechanics and Microengineering, vol. 17; Mar. 21, 2007.
Anantharamaiah et al; A study on flow through hydroentangling nozzles and their degradation; pp. 4582-4594; Chemical Engineering Science, vol. 61; May 2006.
Anantharamaiah et al; Numerical Simulation of the Formation of Constricted Waterjets in Hydroentangling Nozzles Effects of Nozzle Geometry; pp. 31-238; Chemical Engineering Research and Design, vol. 84; Mar. 2006.
Attin et al; Clinical evaluation of the cleansing properties of the nonistrumental technique for cleaning root canals; pp. 929-933; International Endodontic Journal, vol. 35, Issue 11; Nov. 2002.
Batchelor et al; Analysis of the stability of axisymmetric jets; pp. 529-551; Journal of Fluid Mechanics, vol. 14; Dec. 1962.
Begenir et al; Effect of Nozzle Geometry on Hydroentangling Water Jets: Experimental Observations; pp. 178-184; Textile Research Journal, vol. 74; Feb. 2004.
Begenir, Asli; The Role of Orifice Design in Hydroentanglement; Thesis submitted to North Carolina State University; dated Dec. 2002, in 107 pages.
Borkent et al; Is there gas entrapped on submerged silicon wafers? Visualizing nano-scale bubbles with cavitation; pp. 225-228; Solid State Phenomena, vol. 134 (2008); available online Nov. 2007.
Bremond et al; Cavitation on surfaces; pp. S3603-S3608; Journal of Physics: Condensed Matter, vol. 17; Oct. 28, 2005.
Brennen, Christopher E.; Fission of collapsing cavitation bubbles; pp. 153-166; Journal of Fluid Mechanics, vol. 472; Dec. 2002.
Chang et al; Effects of Inlet Surface Roughness, Texture, and Nozzle Material on Cavitation; pp. 299-317; Atomization and Sprays, vol. 16 (2006).
Culjat et al., "B-Scan Imaging of Human Teeth Using Ultrasound," Apr. 2003, in 4 pages.
Didenkulov et al; Nonlinear Acoustic Diagnostics of Scatterer Spatial Distribution in a Cavitation Jet; Nov. 19-23, 2001, pp. 276-278, XI Session of the Russion Acoustical Society.
Dumouchel, Christophe; On the experimental investigation on primary atomization of liquid streams; pp. 371-422; Experimental Fluids, vol. 45; Jun. 22, 2008.
Eddingfield et al; Mathematical Modeling of High Velocity Water Jets; pp. 25-39; Proceedings of 1st U.S. Water Jet Conference; 1981.
EMS Electro Medical Systems, "Cleaning", in 2 pages, dated 2005, downloaded from http://www.ems-dent.com/en/endodontics cleaning. htm.
ESI Endo Soft Instruments, EMS Electro Medical Systems, Brochure in 2 pages, downloaded from www.emsdent.com, dated Jan. 2004.
European Extended Search Report, dated Sep. 22, 2011, for EP Application No. 07755777.5., in 7 pages.
Feng et al; Enhancement of ultrasonic cavitation yield by multifrequency sonication; pp. 231-236; Ultrasonics Sonochemistry, vol. 9; Oct. 2002.
Flint, E. B., et al., "The Temperature of Cavitation", Science, vol. 253, Sep. 20, 1991, pp. 1397-1399.
Foldyna et al; Acoustic wave propagation in high-pressure system; pp. e1457-e1460; Ultrasonics vol. 44 (Supplement 1); Jun. 8, 2006.
G.E. Reisman and C.E. Brennen, "Pressure Pulses Generated by Cloud Cavitation", FED-vol. 236, 1996 Fluids Engineering Division Conference, vol. 1, pp. 319-328, ASME 1996.
G.E. Reisman, Y.-C. Wang and C.E. Brennen, "Observations of shock waves in cloud cavitation", J. Fluid Mech. (1998), vol. 355, pp. 255-283.
Ghassemieh et al; Effect of Nozzle Geometry on the Flow Characteristics of Hydroentangling Jets; pp. 444-450; Textile Research Journal, vol. 73; May 2003.
Ghassemieh et al; The effect of nozzle geometry on the flow characteristics of small water jets; pp. 1739-1753; Proceedings of the Institute of Mechanical Engineers, Part C: Mechanical Engineering Science, vol. 12, Sep. 2006.
Hahn et al; Acoustic resonances in the bubble plume formed by a plunging water jet; pp. 1751-1782; Proceedings of the Royal Society of London A, vol. 459; May 16, 2003.
Hashish, Mohamed; Experimental Studies of Cutting with Abrasive Waterjets; pp. 402-416; Proceedings of 2nd American Water Jet Conference; 1983.
Herbert et al; Cavitation pressure in water; pp. 041603-1 to 041603-22; Physical Review E, vol. 74; Oct. 2006.
Hiroyasu, Hiro; Spray Breakup Mechanism from the Hole-Type Nozzle and its Applications; pp. 511-527; Atomization and Sprays, vol. 10 (2000).
Hmud R. et al. "Cavitational Effects in Aqueous Endodontic Irrigants Generated by Near-Infrared Lasers", Journal of Endodontics, vol. 36, Issue 2, Feb. 2010, available online Dec. 4, 2009, in 4 pages.
Hoque et al; Air entrainment and associated energy dissipation in steady and unsteady plunging jets at free surface; pp. 37-45; Applied Ocean Research, vol. 30; May 2008.
Hydrocision Products: SpineJet Hydrosurgery; system webpage in 2 pages, copyright 2010, downloaded from http://www.hydrocision.com on Apr. 22, 2010.
Hydrocision SpineJet XL HydroSurgery System; Brochure in 2 pages, copyright 2004-2006, downloaded from http://www.hydrocision.com on Apr. 22, 2010.
International Search Report and Written Opinion re App. No. PCT/US2010/056620, dated Jan. 12, 2011.
Jackson et al; Nozzle Design for Coherent Water Jet Production; pp. 53-89; Proceeding of the 2nd US Water Jet Conference; May 1983.
Junge et al; Cell Detachment Method Using Shock-Wave-Induced Cavitation; pp. 1769-1776; Ultrasound in Medicine & Biology, vol. 29, No. 12; Dec. 2003.
Kalumuck et al; Development of High Erosivity Well Scale Cleaning Tools; pp. 1-36; Dynaflow, Inc.; Report 98012 conducted under Contract No. DE-FG07-981013684 for the US Dept. of Energy; Jul. 1999, in 36 pages.
Karasawa et al; Effect of Nozzle Configuration on the Atomization of a Steady Spray; pp. 411-426; Atomization and Sprays, vol. 2 (1992).
Kato, Hiroharu; Utilization of Cavitation for Environmental Protection—Killing Planktons and Dispersing Spilled Oil; pp. 1-8; in CAV2001: Fourth International Symposium on Caviation; California Institute of Technology, Pasadena, CA; dated Jun. 2001.
Lee et al; The efficacy of ultrasonic irrigation to remove artificially placed dentine debris from different-sized simulated plastic root canals; pp. 607-612; International Endodontic Journal, vol. 37; May 2004.
Li et al; Cavitation Resonance; pp. 031302-1 to 031302-7; Journal of Fluids Engineering, vol. 130; Mar. 2008.

(56) References Cited

OTHER PUBLICATIONS

Lienhard V et al; Velocity Coefficients for Free Jets From Sharp-Edged Orifices; pp. 13-17; Reprinted from Mar. 1984, vol. 106, Journal of Fluids Engineering.
Lin et al; Drop and Spray Formation from a Liquid Jet; pp. 85-105; Jan. 1998: vol. 30; Annual Review of Fluid Mechanics.
Linfield, Kevin William; A Study of the Discharge Coefficient of Jets From Angled Slots and Conical Orifices; Thesis submitted to Dept. of Aerospace Science and Engineering; University of Toronto; dated 2000; in 148 pages.
Lussi et al; A new non-instrumental technique for cleaning and filling root canals; pp. 1-6; International Endodontic Journal, vol. 28; Jan. 1995.
Lussi et al; A Novel Noninstrumented Technique for Cleansing the Root Canal System; pp. 549-553; Journal of Endodontics, vol. 19, No. 11; Nov. 1993.
Lussi et al; In vivo performance of the new non-instrumentation technology (NIT) for root canal obturation; pp. 352-358; International Endodontic Journal, vol. 35; Apr. 2002.
Maximum Dental Inc., "Canal Clean Max", "Intra Canal Irrigation and Aspiration Device", and "SonicMax, Endo-Perio Sonic Handpiece", in 3 pages, downloaded from www.dentalmaximum.com on May 8, 2008.
Ohrn et al; Geometric Effects on Spray Cone Angle for Plain-Orifice Atomizers; pp. 253-268; Atomization and Sprays, vol. 1 (1991).
Ohrn et al; Geometrical Effects on Discharge Coefficients for Plain-Orifice Atomizers; pp. 137-153; Atomization and Sprays, vol. 1, No. 2 (1991).
Phinney, Ralph E.; The breakup of a turbulent liquid jet in a gaseous atmosphere; pp. 689-701; J. Fluid Mechanics, vol. 60, Part 4; Oct. 1973.
Piezon Master 600 Ultrasound a la carte, EMS Electro Medical Systems, EMS SA FA-319.EN ed. Mar. 2009; Brochure dated Mar. 2009, in 2 pages.
Quinn, W. R.; Experimental study of the near field and transition region of a free jet issuing from a sharp-edged elliptic orifice plate; pp. 583-614; European Journal of Mechanics—B/Fluids, vol. 26; Jul.-Aug. 2007; available online Dec. 2006.
Ramamurthi et al; Disintegration of Liquid Jets from Sharp-Edged Nozzles; pp. 551-564; Atomization and Sprays, vol. 4 (1994).
Reitz et al; Mechanism of atomization of a liquid jet; pp. 1730-1742; Physics Fluids, vol. 25, No. 10; Oct. 1982.
Sallam et al; Liquid breakup at the surface of turbulent round liquid jets in still gases; pp. 427-449; International Journal of Multiphase Flow, vol. 28; Mar. 2002.
Sawant et al; Effect of hydrodynamic cavitation on zooplankton: A tool for disinfection; pp. 320-328; Biochemical Engineering Journal, vol. 42, Issue 3; Dec. 2008.
Shi et al; Comparison-speed liquid jets; Experiments in Fluids, vol. 35; pp. 486-492; Oct. 7, 2003.
Sou et al; Effects of cavitation in a nozzle on liquid jet atomization; pp. 3575-3582; International Journal of Heat and Mass Transfer, vol. 50; Mar. 2007.
Soyama et al; High-Speed Observation of Ultrahigh-Speed Submerged Water Jets; pp. 411-416; Experimental Thermal and Fluid Science, vol. 12 1996).
Soyama, Hitoshi; High-Speed Observation of a Cavitating Jet in Air; Journal of Fluids Engineering, vol. 127; pp. 1095-1101; Nov. 2005.
Summers, David A; Considerations in the Comparison of Cavitating and Plain Water Jets; pp. 178-184; Rock Mechanics and Explosive Research Center, Rolla, Missouri.
Summers, David A; The Volume Factor in Cavitation Erosion; Proceedings of 6th International Conference on Erosion by Liquid and Solid Impact; University of Missouri-Rolla; Rolla, Missouri, 1983, in 12 pages.
Suslick, K. S., et al., "The Sonochemical Hot Spot", Journal of the American Chemical Society, vol. 108, No. 18, Sep. 3, 1986, pp. 5641-5642.
Suslick, K. S., et al., "Heterogeneous Sonocatalysis with Nickel Powder", Journal of the American Chemical Society, vol. 109, No. 11, May 27, 1987, pp. 3459-3461.
Tafreshi et al; Simulating Cavitation and Hydraulic Flip Inside Hydroentangling Nozzles; pp. 359-364; Textile Research Journal, vol. 74, Apr. 2004.
Tafreshi et al; Simulating the Flow Dynamics in Hydroentangling Nozzles: Effect of Cone Angle and Nozzle Aspect Ratio; pp. 700-704; Textile Research Journal, vol. 73; Aug. 2003.
Tafreshi et al; The effects of nozzle geometry on waterjet breakup at high Reynolds numbers; pp. 364-371; Experiments in Fluids, vol. 35; Sep. 2, 2003.
Zuo et al; An Attribution of Cavitation Resonance: Volumetric Oscillations of Cloud; pp. 152-158; Journal of Hydrodynamics, vol. 21; Apr. 2009.
European Extended Search Report, re EP Application No. 08728345.3, dated Mar. 3, 2014.
International Search Report and Written Opinion, re PCT Application No. PCT/US2013/077286, mailed May 27, 2014.
Fuchs, "Ultrasonic Cleaning: Fundamental Theory and Application," Blackstone-Ney Ultrasonics, Jamestown, NY, May 2002, 14 pages.
Hungarian Written Opinion and Search Report via/re Singapore Application No. 189554, mailed Oct. 13, 2013, in 81 pages.
International Search Report and Written Opinion mailed Jun. 28, 2013, re PCT Application No. PCT/US2013/036493, in 21 pages.
International Search Report and Written Opinion, re PCT Application No. PCT/US 13/32635, mailed Jun. 17, 2013 in 14 pages.
Sabeti, "Healing of apical periodontitis after endodontic treatment with and without obturation in dogs," Journal of Endodontics, Jul. 2006, pp. 628-633.
International Preliminary Report on Patentability received in International Patent Application No. PCT/US2011/057401, mailed on Jan. 25, 2013, filed on Oct. 21, 2011; in 13 pages.
International Preliminary Report and Written Opinion dated Nov. 9, 2010 for International Appl. No. PCT/US09/43386, in 7 pages.
International Preliminary Report on Patentability dated Aug. 6, 2009, for International Appl. No. PCT/US08/52122, in 14 pages.
International Preliminary Report on Patentability dated Oct. 30, 2008, for International Appl. No. PCT/US07/09633, in 5 pages.
International Preliminary Report on Patentability re App. No. PCT/US2010/056620, issued May 15, 2012, in 10 pages.
International Search Report and Written Opinion dated Apr. 11, 2008, for International Appl. No. PCT/US07/09633, in 11 pages.
International Search Report and Written Opinion dated Aug. 8, 2008, for International Appl. No. PCT/US08/52122, in 20 pages.
International Search Report and Written Opinion dated Jul. 29, 2009, for International Appl. No. PCT/US09/43386, in 9 pages.
International Search Report and Written Opinion from International Application No. PCT/US2011/057401, dated Jan. 30, 2012, in 20 pages.
European Extended Search Report re EP Application No. 14187012.1, dated Mar. 3, 2015, in 10 pages.
International Preliminary Report on Patentability and Written Opinion, mailed Oct. 14, 2014, re PCT Application No. PCT/US2013/036493, in 14 pages.
International Search Report and Written Opinion re App. No. PCT/US2014/014732, mailed Jul. 18, 2014.
International Search Report and Written Opinion, re PCT Application No. PCT/US2014/036451, mailed Jan. 21, 2015, in 20 pages.
International Search Report and Written Opinion, re PCT Application No. PCT/US2014/044186, mailed Jan. 21, 2015, in 19 pages.
U.S. Appl. No. 61/701,947, Sep. 17, 2012, Laufer.
U.S. Appl. No. 61/894,762, Oct. 23, 2013, Lifshitz et al.
U.S. Appl. No. 61/895,316, Oct. 24, 2013, Lifshitz et al.
European Extended Search Report, re EP Application No. 10830829.7, dated Oct. 21, 2015, in 6 pages.
European Extended Search Report, re EP Application No. 13763534.8, dated Jan. 15, 2016, in 8 pages.
European Extended Search Report, re EP Application No. 13775073.3, dated Nov. 3, 2015, in 10 pages.
International Preliminary Report on Patentability re PCT Application No. PCT/US2014/014732, issued Aug. 4, 2015, in 10 pages.

(56) References Cited

OTHER PUBLICATIONS

International Preliminary Report on Patentability, re PCT Application No. PCT/US2013/077286, issued Jun. 23, 2015, in 8 pages.
International Preliminary Report on Patentability, re PCT Application No. PCT/US2014/036451, issued Nov. 3, 2015, 2015, in 11 pages.
International Preliminary Report on Patentability, re PCT Application No. PCT/US2014/044186, mailed Dec. 29, 2015, in 19 pages.
International Search Report and Written Opinion, re PCT Application No. PCT/US2015/028360, mailed Sep. 28, 2015, in 24 pages.
Wohlgemuth et al.: "Effectiveness of GentleWave System in Removing Separated Instruments," JOE, vol. 41, No. 11, Nov. 2015, pp. 1895-1898.
European Extended Search Report, re EP Application No. 11835265.7, dated Mar. 30, 2016, in 9 pages.
Ebihara et al.: "Er:YAG laser modification of root canal dentine: Influence of pulse duration, repetitive irradiation and water spray," Lasers in Medical Science, 17(3), 198-207, Aug. 2002.
Nammour et al.: "External temperature during KTP-nd:YAG laser irradiation in root canals: An in vitro study," Lasers in Medical Science, 19(1), 27-32, Jul. 2004.
Ulrich Schoop et al.: "The use of the erbium, chromium:yttrium-scandium-gallium-garnet laser in endodontic treatment: The results of an in vitro study," The Journal of the American Dental Association: vol. 138, Issue 7, Jul. 2007, pp. 949-955.

\* cited by examiner

APPARATUS, METHODS, AND COMPOSITIONS FOR ENDODONTIC TREATMENTS

CROSS-REFERENCE TO RELATED APPLICATIONS

This application claims the benefit of U.S. Provisional Patent Application No. 61/405,616, filed Oct. 21, 2010, entitled "APPARATUS AND METHODS FOR ROOT CANAL TREATMENTS," and U.S. Provisional Patent Application No. 61/485,089, filed May 11, 2011, entitled "APPARATUS AND METHODS FOR ROOT CANAL TREATMENTS," each of which is hereby incorporated by reference herein in its entirety.

BACKGROUND

Field

The present disclosure relates generally to dentistry and endodontics and to apparatus, methods, and compositions for treating a tooth.

Description of Related Art

In conventional root canal procedures, an opening is drilled through the crown of a diseased tooth, and endodontic files are inserted into the root canal system to open the canal spaces and remove organic material therein. The root canal is then filled with solid matter such as gutta percha or a flowable obturation material, and the tooth is restored. However, this procedure will not remove all organic material from the canal spaces, which can lead to post-procedure complications such as infection. In addition, motion of the endodontic file may force organic material through an apical opening into periapical tissues. In some cases, an end of the endodontic file itself may pass through the apical opening. Such events may result in trauma to the soft tissue near the apical opening and lead to post-procedure complications.

SUMMARY

Various non-limiting aspects of the present disclosure will now be provided to illustrate features of the disclosed apparatus, methods, and compositions. Examples of apparatus, methods, and compositions for endodontic treatments are provided.

In one aspect, the apparatus can include a fluid platform configured to substantially retain fluid in a tooth chamber during treatment. The fluid platform can help maintain fluid circulation in the tooth chamber as fluid flows into and out of the tooth chamber. The fluid platform can regulate pressures within a tooth chamber in a tooth. The fluid platform can include one or move vents that permit fluid to leave the tooth (e.g., to inhibit over-pressurization or under-pressurization of the tooth chamber) and/or can inhibit air from flowing into the tooth chamber (which can inhibit generation of pressure waves or acoustic cavitation in fluid in the tooth chamber). The fluid platform may promote fluid circulation in the tooth chamber by retaining fluid (and fluid momentum) in the tooth chamber.

In another aspect, the apparatus can include a pressure wave generator configured to generate acoustic waves that can be used for cleaning root canals and tooth surfaces in the tooth chamber. The pressure wave generator can include one or more of a liquid jet device, a waveguide that propagates light energy into a tooth chamber, an ultrasonic device, or a mechanical stirrer.

In another aspect, the fluid can include antiseptic or antibacterial solutions to assist in tooth cleaning. The fluid may be degassed to have a reduced dissolved gas content (compared to non-degassed fluids used in endodontic treatments), which may improve the effectiveness of the pressure wave generation or the cleaning.

All possible combinations and subcombinations of the aspects and embodiments described in this application are contemplated. For example, one embodiment can include a fluid platform and a pressure wave generator. Another embodiment can include a fluid platform with one or more vents. Some embodiments can include a fluid platform with a fluid inlet for delivering fluid to the tooth chamber and/or a fluid outlet for removing fluid from the tooth chamber. In some such embodiments, the fluid outlet may be vented, which may help regulate pressure in the tooth chamber. Another embodiment can include a fluid platform that delivers a degassed fluid to the tooth chamber. Another embodiment can include a pressure wave generator comprising a liquid jet device, in which the liquid jet comprises a degassed liquid. Other examples of combinations of apparatus are described herein.

For purposes of this summary, certain aspects, advantages, and novel features of certain disclosed inventions are summarized. It is to be understood that not necessarily all such advantages may be achieved in accordance with any particular embodiment of the invention. Thus, for example, those skilled in the art will recognize that the inventions disclosed herein may be embodied or carried out in a manner that achieves one advantage or group of advantages as taught herein without necessarily achieving other advantages as may be taught or suggested herein. Further, the foregoing is intended to summarize certain disclosed inventions and is not intended to limit the scope of the inventions disclosed herein.

BRIEF DESCRIPTION OF THE DRAWINGS

FIGS. 2B-1 and 2B-2 are graphs that schematically illustrate possible examples of acoustic power that could be generated by different embodiments of the pressure wave generator.

FIG. 15A is a side view, FIG. 15B is a partial cutaway view that shows a pressure wave generator disposed in the tooth chamber, and FIG. 15C is a close-up view showing the distal end of the handpiece and the pressure wave generator.

Throughout the drawings, reference numbers may be re-used to indicate a general correspondence between referenced elements. The drawings are provided to illustrate example embodiments described herein and are not intended to limit the scope of the disclosure.

DETAILED DESCRIPTION

The present disclosure describes apparatus, methods, and compositions for performing dental procedures such as, e.g., endodontic procedures. The disclosed apparatus, methods, and compositions advantageously may be used with root canal cleaning treatments, for example, to efficiently remove organic and/or inorganic matter from a root canal system and/or to disinfect the root canal system. The apparatus, methods, and compositions may be used for other dental treatments such as, e.g., tooth cleaning, treatment of dental caries, removal of calculus and plaque, etc. Organic material (or organic matter) includes organic substances typically found in healthy or diseased teeth or root canal systems such as, for example, soft tissue, pulp, blood vessels, nerves, connective tissue, cellular matter, pus, and microorganisms, whether living, inflamed, infected, diseased, necrotic, or decomposed. Inorganic matter includes calcified tissue and calcified structures, which are frequently present in the root canal system.

Figure 1:
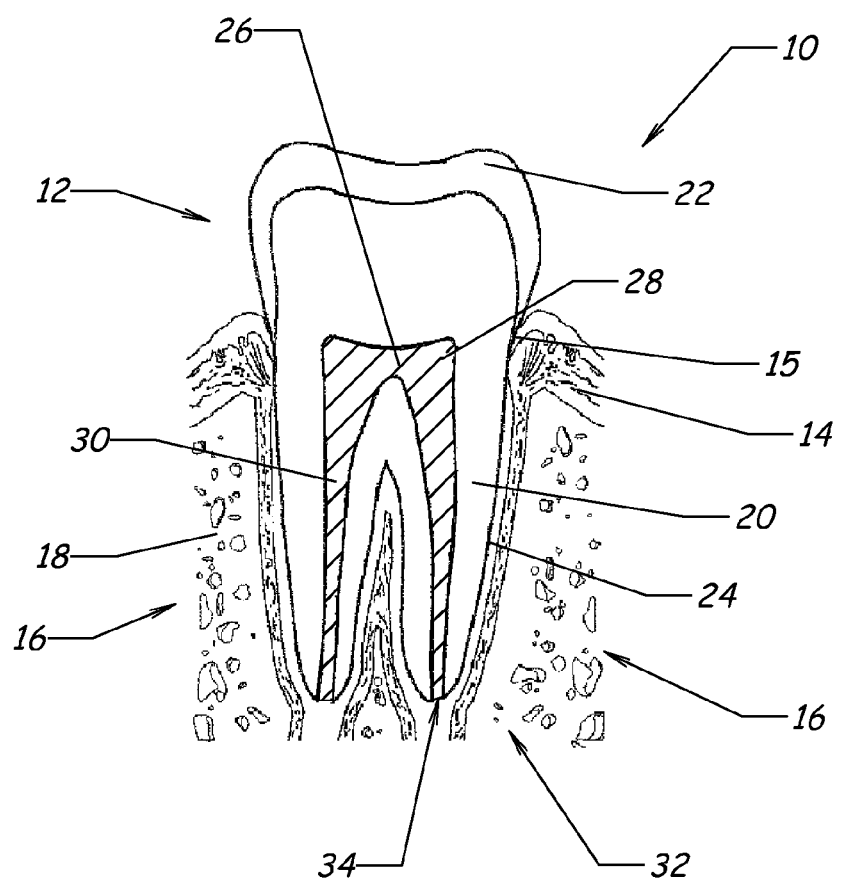
FIG. 1 is a cross-section view schematically illustrating a root canal system of a tooth.

FIG. 1 is a cross section schematically illustrating an example of a typical human tooth 10, which comprises a crown 12 extending above the gum tissue 14 and at least one root 16 set into a socket (alveolus) within the jaw bone 18. Although the tooth 10 schematically depicted in FIG. 1 is a molar, the apparatus and methods described herein may be used on any type of human or animal tooth such as an incisor, a canine, a bicuspid, a pre-molar, or a molar. The hard tissue of the tooth 10 includes dentin 20 which provides the primary structure of the tooth 10, a very hard enamel layer 22 which covers the crown 12 to a cementoenamel junction 15 near the gum 14, and cementum 24 which covers the dentin 20 of the tooth 10 below the cementoenamel junction 15.

A pulp cavity 26 is defined within the dentin 20. The pulp cavity 26 comprises a pulp chamber 28 in the crown 12 and a root canal space 30 extending toward an apex 32 of each root 16. The pulp cavity 26 contains dental pulp, which is a soft, vascular tissue comprising nerves, blood vessels, connective tissue, odontoblasts, and other tissue and cellular components. The pulp provides innervation and sustenance to the tooth 10 through the epithelial lining of the pulp chamber 28 and the root canal space 30. Blood vessels and nerves enter/exit the root canal space 30 through a tiny opening, the apical foramen 34, near a tip of the apex 32 of the root 16.

I. OVERVIEW OF EXAMPLES OF SYSTEMS FOR ENDODONTIC TREATMENTS

A. Examples of Pressure Wave Generators

Figure 2A:
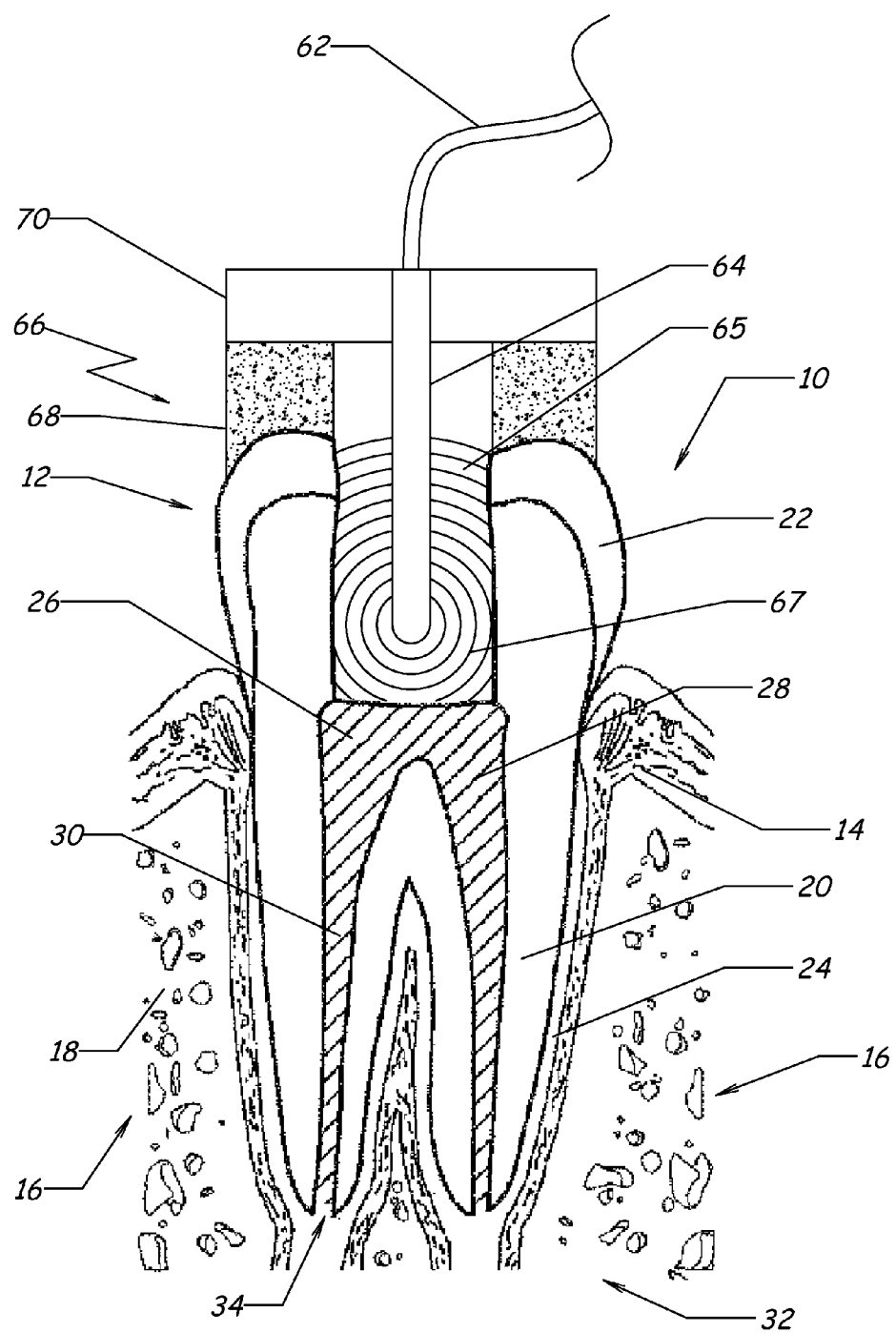
FIG. 2A schematically illustrates an example of a system for treating a tooth with a pressure wave generator.

FIG. 2A schematically illustrates an example of a system for treating a tooth 10 with a pressure wave generator 64. An endodontic access opening can be formed into the tooth 10, for example, on an occlusal surface, a buccal surface, or a lingual surface. The access opening provides access to a portion of the pulp cavity 26 of the tooth 10. The system can include a fluid retainer 66 and the pressure wave generator 64. The pressure wave generator 64 can be electrically connected to a source of electrical power by an electrical lead 62.

The fluid retainer 66 can comprise a cap 70 and a flow restrictor 68 that inhibits flow of fluid from the tooth 10. The flow restrictor 68 may also inhibit flow of air into the tooth 10. The cap 70 may be formed from a sufficiently durable, biocompatible substance such as metal or plastic. The flow restrictor 68 may include a sponge, a membrane (permeable or semi-permeable), or a vent. The flow restrictor 68 may limit fluid pressure in the tooth 10 such that if the fluid pressure rises above a threshold, fluid can leak or flow from the tooth chamber through the flow restrictor 68. The use of a flow restrictor 68 advantageously may prevent fluid pressure in the tooth chamber (e.g., in the pulp chamber 28 or at the apex 32 of the tooth) from rising to undesirable or unsafe levels. Fluids as described herein generally means liquids, and the liquids may include a certain amount of dissolved gas. For example, a fluid can include water (having a normal dissolved gas (e.g., air) content as can be determined from Henry's law for the appropriate temperature and pressure conditions) or degassed water, which can have a reduced dissolved gas content as compared to water with a normal dissolved gas content.

The fluid retainer 66 may include a handpiece (not shown) by which a dental practitioner can apply or maneuver the fluid retainer 66 relative to the tooth 10 during treatment. In some implementations, the fluid retainer 66 can be applied to the tooth with a mechanical clasp or clamp (see, e.g., FIGS. 10A and 10B), a dental adhesive, or by pressure applied by the patient by biting on the retainer (see, e.g., FIG. 11).

The fluid retainer 66 may be configured to be applied to the tooth, for example, by placing the retainer on an occlusal surface of the tooth (with or without an adhesive or flow restrictor such as a sponge), by covering or plugging an access opening to the tooth chamber, by wrapping a portion of the fluid retainer around the tooth, etc. For example, although FIG. 2A shows the fluid retainer 66 placed over the occlusal surface of the tooth 10, in other embodiments the distal end of the fluid retainer 66 is sized or shaped to fit into the access opening, e.g., as a plug.

As schematically illustrated in FIG. 2A, a distal end of the pressure wave generator 64 can be disposed in the fluid in a tooth chamber 65 in the tooth (sometimes the tooth chamber 65 may be referred to herein as a tooth cavity). The tooth chamber 65 may include at least a portion of any space, opening, or cavity of the tooth 10, including any portion of spaces, openings, or cavities already present in the tooth 10 (either by normal or abnormal dentin and/or tissue structure or by degeneration, deterioration, or damage of such structure) and/or any portion of spaces, openings, or cavities formed by a dental practitioner during a treatment. For example, the tooth chamber 65 may include at least a portion of the pulp chamber 28 and may also include at least a portion of one or more of the following: an access opening to the tooth, a root canal space 30, and a tubule. In some treatments, the tooth chamber 65 can include some or all of the root canal spaces 30, accessory canals, and tubules in the tooth 10. In some treatments, the access opening can be formed apart or separately from the tooth chamber.

The distal end of the pressure wave generator 64 may be disposed in the tooth chamber, for example, in the pulp chamber 28. The distal end of the pressure wave generator 64 may be sized or shaped to fit in the tooth chamber. For example, the distal end of the pressure wave generator may be sized to fit in or through an endodontic access opening formed in the tooth. In some treatment methods, the distal end of the pressure wave generator 64 may be disposed within a few millimeters of the floor of the pulp chamber 28 (see, e.g., FIG. 15C). In other methods, the distal end of the pressure wave generator 64 can be disposed in the fluid retained by the fluid retainer 66, but outside the pulp cavity 26 (e.g., beyond the occlusal surface of the tooth). In some implementations, the pressure wave generator 64 (in addition to or as an alternative to the fluid retainer 66) may be coupled to a handpiece or portable housing that may be maneuvered in the mouth of the patient so as to position or orient the pressure wave generator 64 relative to a desired tooth under treatment.

The distal end of the pressure wave generator 64 may be submerged in fluid in the tooth chamber during at least a portion of the endodontic procedure. For example, the distal end of the pressure wave generator 64 may be disposed in the tooth chamber 65 while there is little or not liquid in the tooth chamber. Fluid can be added to the tooth chamber such that a fluid level rises above the distal end of the generator 64. The pressure wave generator 64 may then be activated for at least a portion of the endodontic procedure. During other portions of the procedure, the generator 64 may be inactive and/or above the fluid level in the tooth chamber 65.

In various implementations, the pressure wave generator 64 comprises one or more embodiments of the various apparatus described herein. For example, the pressure wave generator 64 can include a liquid jet device. In some embodiments, the liquid jet device comprises a positioning member (e.g., a guide tube) having a channel or lumen along which or through which a liquid jet can propagate. The distal end portion of the positioning member may include an impingement surface on which the liquid jet impinges and is deflected into jets or spray. The distal end portion of the positioning member may include one or more openings that permit the jet to interact with the fluid in the surrounding environment (e.g., fluid in the tooth chamber) and also permit the deflected liquid to exit the positioning member and interact with the surrounding environment in the tooth 10 (e.g., the tooth chamber and the fluid in the tooth chamber). The result of these interactions can be generation of pressure waves and fluid circulation in the tooth chamber 65, which can at least partially clean the tooth. In some treatment methods, the openings disposed at or near the distal end portion of the positioning member are submerged in fluid retained in the tooth 10 by the fluid retainer 66. As will be further described below with reference to FIG. 3A, in some such embodiments the liquid jet device may function as a fluid inlet 71 to the tooth chamber 65 and may deliver fluid to at least partially fill the chamber. Accordingly, in some such embodiments, the liquid jet device functions as a pressure wave generator 64 and as a fluid inlet 71.

In some embodiments, the pressure wave generator 64 may include a sonic, ultrasonic, or megasonic device (e.g., a sonic, ultrasonic, or megasonic paddle, horn, or piezoelectric transducer), a mechanical stirrer (e.g., a motorized propeller or paddle or rotating/vibrating/pulsating disk or cylinder), an optical system that can provide optical energy to the tooth chamber 65 (e.g., an optical fiber that propagates laser light into the tooth chamber), or any other device that can cause a pressure wave to be generated in the tooth or in a propagation medium in the tooth (e.g., the fluid retained in a tooth chamber).

In some embodiments, the cap 70 is not used. For example, the flow restrictor 68 may be applied to the occlusal surface of the tooth 10 around or over the access opening, and the distal end of the pressure wave generator 64 can be inserted into the tooth chamber 65 through the flow restrictor 68 (or an opening in the flow restrictor).

(1) Examples of Acoustic Cavitation Produced by the Pressure Wave Generator

The pressure wave generator 64 can be configured to generate an acoustic wave 67 that can propagate through the tooth and/or the fluid in the tooth chamber 65 and can detach or dissolve organic and/or inorganic material from dentinal surfaces and/or dissociate pulpal tissue. The fluid in the tooth chamber 65 can act as a propagation medium for the acoustic wave 67 and can help propagate the acoustic wave 67 toward the apex 32 of the root canal space 30, into tubules, and into other spaces in the tooth where organic matter may be found. The acoustic wave 67 may cause or increase the efficacy of various effects that may occur in the tooth 10 including, but not limited to, acoustic cavitation (e.g., cavitation bubble formation and collapse, inertial cavitation, microjet formation), acoustic streaming, microerosion, fluid agitation, fluid circulation, voracity, sonoporation, sonochemistry, and so forth. The acoustic energy may be sufficient to cause organic and/or inorganic material in the tooth to be detached from surrounding dentin. It is believed (although not required) that the effects caused (or enhanced) by the acoustic energy may lead to a cleaning action that delaminates or detaches the pulpal tissue from the root canal wall, dentinal surfaces, and/or tubules, and may further break such tissue down into smaller pieces.

Without subscribing to or being limited by any particular theory or mode of operation, the acoustic field generated by the pressure wave generator 64 may generate a cavitation cloud within the fluid retained in the tooth chamber 65. The creation and collapse of the cavitation cloud (and/or the jet impacting the impingement surface) may, in some cases, generate a substantial hydroacoustic field in the tooth 10. This acoustic field may generate pressure waves, oscillations, and/or vibrations in or near the canal spaces of the tooth and/or interior dentinal surfaces, which are filled with dentinal tubules. Further cavitation effects may be possible, including growth, oscillation, and collapse of cavitation bubbles formed in or near the tubules (e.g., possibly at the high surface-energy sites of the tubules). These (and/or other) effects may lead to efficient cleaning of the pulp chamber 28 of the tooth.

(2) Examples of Acoustic Power Generated by Pressure Wave Generators

Figures 1, 2B:
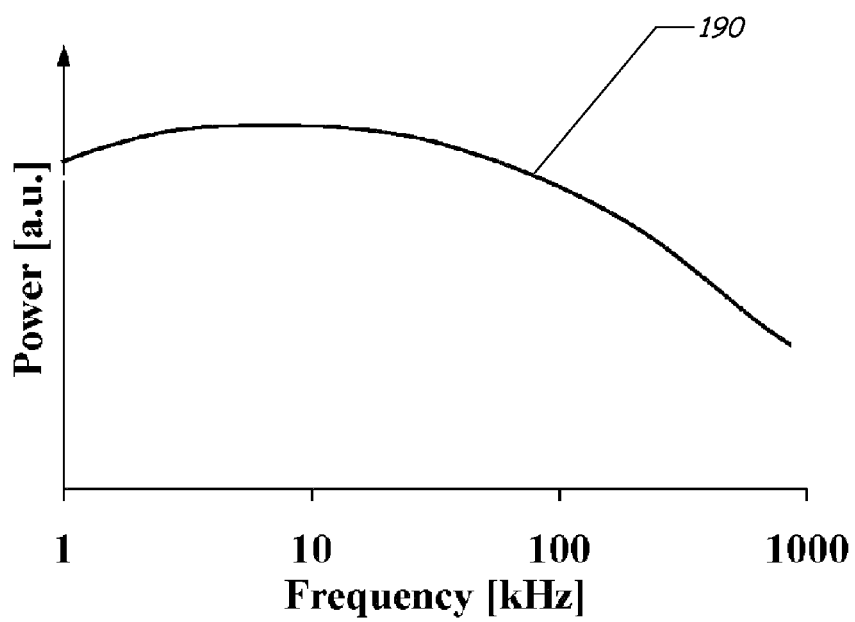
Figures 2, 2B:
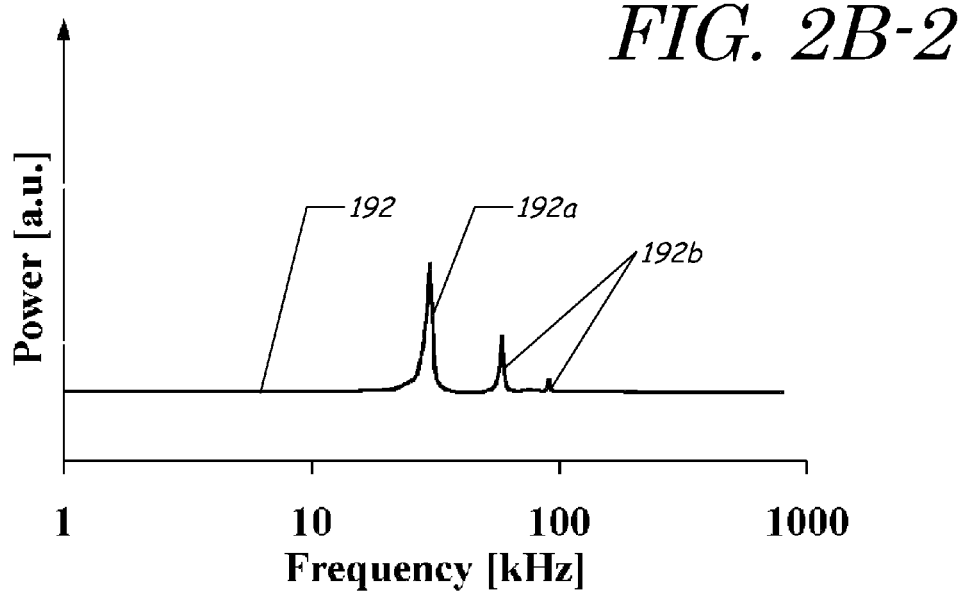

FIGS. 2B-1 and 2B-2 are graphs that schematically illustrate possible examples of acoustic power that could be generated by different embodiments of the pressure wave generator. These graphs schematically show acoustic power (in arbitrary units) on the vertical axis as a function of acoustic frequency (in kHz) on the horizontal axis. The acoustic power in the tooth may influence, cause, or increase the strength of effects including, e.g., acoustic cavitation (e.g., cavitation bubble formation and collapse, microjet formation), acoustic streaming, microerosion, fluid agitation, fluid circulation, sonoporation, sonochemistry, and so forth, which may act to dissociate organic material in the tooth 10 and effectively clean the pulp cavity 26 and/or the canal spaces 30. In various embodiments, the pressure wave generator 64 may produce an acoustic wave 67 including acoustic power (at least) at frequencies above: about 0.5 kHz, about 1 kHz, about 10 kHz, about 20 kHz, about 50 kHz, about 100 kHz, or greater. The acoustic wave 67 may have acoustic power at other frequencies as well (e.g., at frequencies below the aforelisted frequencies).

The graph in FIG. 2B-1 represents a schematic example of acoustic power generated by a liquid jet impacting a surface disposed in a tooth chamber 65 and by the interaction of the liquid jet with fluid in the tooth chamber. This schematic example shows a broadband spectrum 190 of acoustic power with significant power extending from about 1 kHz to about 1000 kHz (e.g., the bandwidth may about 1000 kHz). The bandwidth of the acoustic energy spectrum may, in some cases, be measured in terms of the 3-decibel (3-dB) bandwidth (e.g., the full-width at half-maximum or FWHM of the acoustic power spectrum). In various examples, a broadband acoustic power spectrum may include significant power in a bandwidth in a range from about 1 kHz to about 500 kHz, in a range from about 10 kHz to about 100 kHz, or some other range of frequencies. In some implementations, a broadband spectrum may include acoustic power above about 1 MHz. In some embodiments, the pressure wave generator 64 can produce broadband acoustic power with peak power at about 10 kHz and a bandwidth of about 100 kHz. In various embodiments, the bandwidth of a broadband acoustic power spectrum is greater than about 10 kHz, greater than about 50 kHz, greater than about 100 kHz, greater than about 250 kHz, greater than about 500 kHz, greater than about 1 MHz, or some other value. In some cleaning methods, acoustic power between about 20 kHz and 200 kHz may be particularly effective. The acoustic power may have substantial power at frequencies greater than about 1 kHz, greater than about 10 kHz, greater than about 100 kHz, or greater than about 500 kHz. Substantial power can include, for example, an amount of power that is greater than 10%, greater than 25%, greater than 35%, or greater than 50% of the total acoustic power (e.g., the acoustic power integrated over all frequencies).

The graph in FIG. 2B-2 represents a schematic example of acoustic power generated by an ultrasonic transducer disposed in a tooth chamber 65. This schematic example shows a relatively narrowband spectrum 192 of acoustic power with a highest peak 192a near the fundamental frequency of about 30 kHz and also shows peaks 192b near the first few harmonic frequencies. The bandwidth of the acoustic power near the peak is about 5 to 10 kHz, and can be seen to be much narrower than the bandwidth of the acoustic power schematically illustrated in FIG. 2B-1. In other embodiments, the bandwidth of the acoustic power can be about 1 kHz, about 5 kHz, about 10 kHz, about 20 kHz, about 50 kHz, about 100 kHz, or some other value. The acoustic power of the example spectrum 192 has most of its power at the fundamental frequency and first few harmonics, and therefore the ultrasonic transducer of this example may provide acoustic power at a relatively narrow range of frequencies (e.g., near the fundamental and harmonic frequencies). The acoustic power of the example spectrum 190 exhibits relatively broadband power (with a relatively high bandwidth compared to the spectrum 192), and the example liquid jet may provide acoustic power at significantly more frequencies than the example ultrasonic transducer.

It is believed, although not required, that acoustic waves having broadband acoustic power (see, e.g., the example shown in FIG. 2B-1) may generate cavitation that is more effective at cleaning teeth than cavitation generated by acoustic waves having a narrowband acoustic power spectrum (see, e.g., the example shown in FIG. 2B-2). For example, a broadband spectrum of acoustic power may produce a relatively broad range of bubble sizes in the cavitation cloud, and the implosion of these bubbles may be more effective at disrupting tissue than bubbles having a narrow size range. Relatively broadband acoustic power may also allow acoustic energy to work on a range of length scales, e.g., from the cellular scale up to the tissue scale. Accordingly, pressure wave generators that produce a broadband acoustic power spectrum (e.g., some embodiments of a liquid jet) may be more effective at tooth cleaning for some endodontic treatments than pressure wave generators that produce a narrowband acoustic power spectrum. In some embodiments, multiple narrowband pressure wave generators may be used to produce a relatively broad range of acoustic power. For example, multiple ultrasonic tips, each tuned to produce acoustic power at a different peak frequency, may be used.

B. Examples of Fluid Platforms for Fluid Management

Some apparatus and methods disclosed herein may perform more efficiently if at least a portion of the pulp cavity 26 of the tooth 10 under treatment is filled with fluid (e.g., liquid) during an endodontic procedure. In some such treatment methods, the pulp chamber 28 may be substantially filled with liquid with substantially no air (or gas) pockets remaining in the pulp chamber 28. For example, leakage of air into the pulp chamber 28 may reduce the effectiveness of the treatment in some circumstances (e.g., by reducing the effectiveness of cavitation and damping the pressure waves). In some treatment methods, leakage of the fluid from the pulp chamber 28 into the oral cavity (e.g., mouth) is not desired as such leakage may leave an unpleasant taste or smell or may lead to damaged tissues in the patient's mouth. Accordingly, in various treatment methods, a fluid platform can be used that maintains a substantially liquid-filled pulp chamber 28, inhibits leakage of air into the pulp chamber 28 during treatment, and/or inhibits leakage of treatment fluid, waste fluid, and/or material from the pulp cavity into the mouth of the patient.

The fluid platform 61 (e.g., a fluid retainer) can be used for maintaining fluid in a tooth chamber 65 in a tooth, which may advantageously enable cleaning of a root canal space 30 (or other portions of the tooth. In some procedures, fluid is delivered to the tooth chamber 65, and the fluid pressure in the tooth chamber 65 may rise. If the fluid pressure in the chamber becomes too great, organic material, fluid, etc. may be forced through the apex 32 of the tooth 10, which may lead to complications such as infection. Also, if for example due to suction negative pressure is created inside the tooth chamber, and if the absolute magnitude of the negative pressure is large enough, the negative pressure may cause problems such as pain and discomfort for the patient. Thus, in various embodiments, the fluid platform 61 is configured such that the pressure created at the apex 32 of the tooth 10 (or in a portion of the tooth chamber such as, e.g., the pulp chamber 28) is below an upper value of: about 500 mmHg, about 300 mmHg, about 200 mmHg, about 100 mmHg, about 50 mmHg, about 30 mmHg, about 20 mmHg, or some other value. (Note: 1 mmHg is one millimeter of mercury and is a measure of pressure equal to about 133.322 Pascal). Embodiments of the fluid platform can be configured so that if the fluid pressure in the tooth chamber 65 rises above an upper threshold, fluid can flow or leak from the chamber to maintain the fluid pressure at a safe or desired level. The threshold can be a predetermined pressure level. Certain predetermined pressure levels can be about 500 mmHg, about 300 mmHg, about 200 mmHg, about 100 mmHg, about 50 mmHg, about 30 mmHg, or about 20 mmHg.

In some implementations, it may be desired that the apical pressure or tooth chamber pressure be greater than a lower value of: about −1000 mmHg, about −500 mmHg, about −300 mmHg, about −200 mmHg, about −100 mmHg, about −50 mmHg, about 0 mmHg, or some other value. For example, if the pressure becomes too low (too negative), the patient may experience discomfort. Embodiments of the fluid retainer can be configured so that if the fluid pressure in the tooth chamber 65 decreases below a lower threshold, ambient air can flow or be drawn through a flow restrictor (e.g., a sponge or vent) to maintain the fluid pressure above a patient-tolerable or desired level. The lower threshold can be a predetermined pressure level. Certain predetermined pressure levels can be about −1000 mmHg, about −500 mmHg, about −300 mmHg, about −200 mmHg, about −100 mmHg, about −50 mmHg, about or 0 mmHg. Thus, various embodiments of the fluid retainer can self-regulate the pressure in the tooth chamber to be below a first (e.g., upper) threshold and/or above a second (e.g., lower) threshold. As discussed, either or both thresholds can be a predetermined pressure level.

The fluid pressure in the tooth chamber 65 may fluctuate with time as fluid flows in and out of the chamber and/or as a pressure wave generator 64 is activated to generate acoustic waves 67 (which comprise pressure oscillations). The acoustic waves 67 may induce cavitation, which can cause pressure fluctuations as well. In some implementations, a mean or average pressure may be used. The mean pressure can be a time average of the pressure (at a particular point in the fluid) over a time period corresponding to the pressure fluctuations occurring in the fluid, or in some contexts, a spatial average of the pressure over a spatial region (e.g., over some or all of the tooth chamber). The pressure at a given point (in space or time) may be much larger than the mean pressure (e.g., due to a cavitation-induced event), and certain embodiments of the fluid platform may provide safety features to inhibit the rise of pressure above an undesired or unsafe threshold (e.g., by providing a vent to allow liquid to flow from the tooth chamber).

In various treatment methods, when a fluid is delivered into a tooth chamber 65 of a tooth 10, management of the fluid in the tooth chamber 65 can be "controlled" or left "uncontrolled."

(1) Examples of Uncontrolled Fluid Platforms

In some types of uncontrolled fluid platforms, the tooth chamber 65 (e.g., a portion of the pulp cavity) may be substantially open to ambient air, fluids, etc., and the fluid inside the tooth chamber 65 may not be fully contained in the tooth chamber 65. For example, the fluid may splash, overflow, or be evacuated via an external system (e.g., a suction wand) during the dental procedure. In some such cases, the fluid can be replenished intermittently or continuously during the procedure (e.g., via irrigation or syringing). The excess waste fluid also may be evacuated from the patient's mouth or from a rubber dam (if used) intermittently or continuously during the procedure.

An example of an uncontrolled method of fluid management can be the irrigation of the root canals with endodontic irrigation syringes. During this procedure, the fluid is injected into and exits from the pulp cavity, flowing into the oral space or a rubber dam (if used) and/or is suctioned by an external evacuation system operated by dental assistant. Another example of uncontrolled fluid management can be activation of the irrigation fluid by ultrasonic tips that can be inserted into the root canals. Upon activation of the ultrasonic device, the fluid in the tooth may splash out of the pulp cavity. The fluid inside the pulp cavity can be replenished via a syringe or the waterline of the ultrasonic tip, and the excess fluid may be suctioned from the oral space or the rubber dam (if used) via an external suction hose operated by a dental assistant.

(2) Examples of Controlled Fluid Platforms

Another type of fluid platform can be categorized as a "controlled" fluid platform. In some types of controlled fluid platforms, the fluid can be substantially contained in the tooth chamber 65 (e.g., pulp cavity) by using an apparatus to at least partially cover an endodontic access opening. Some such fluid platforms may or may not include fluid inlets and/or outlets for the fluid to enter and exit the tooth chamber 65, respectively. Fluid flowing in and/or out of the tooth 10 during a procedure can be controlled. In some embodiments, the total volume (or rate) of fluid going into the tooth 10 can be controlled to be substantially equal to the total volume (or rate) of fluid going out of the tooth 10. Examples of two types of controlled fluid platforms will be described.

(i) Examples of Closed Fluid Platforms

A closed system can be a controlled system where the amount of fluid flowing into the tooth chamber 65 substantially equals the amount of fluid exiting the tooth chamber 65. An example of a closed system includes a fluid cap 70 that is applied or sealed to the tooth 10, around the endodontic opening. In some such systems, the fluid's driving force (e.g., a pressure differential) is applied to only one of the openings (e.g., either inlet or outlet). In other implementations, the driving force can be applied at both the inlet and the outlet, in which case the applied driving forces may be regulated to be substantially equal in magnitude in order to reduce or avoid the following possible problems: exerting pressure (positive or negative) onto the tooth 10 which may result in extrusion of fluid/debris periapically (e.g., positive pressure) or causing pain and/or bleeding due to excessive negative pressure, or breaking the seal of the fluid platform causing leakage of fluid and organic matter into the mouth (e.g., positive pressure) or drawing air into the chamber (e.g., negative pressure) which can reduce the treatment efficiency.

The operation of some closed fluid platforms can be relatively sensitive due to the regulation of the inlet and outlet fluid pressures to be substantially the same. Some such closed systems may lead to safety issues for the patient. For example, some such implementations may not ensure a substantially safe pressure that the patient's body can tolerate (e.g., apical pressures in a range from about −30 mmHg to +15 mmHg, or −100 mmHg to +50 mmHg, or −500 mmHg to +200 mmHg, in various cases). Some such closed systems can result in exertion of pressure (negative or positive) inside the tooth. For instance, if the driving force corresponds to the pressure at the inlet, a small obstruction on the outlet fluid line (which inhibits or reduces outflow of fluid from the tooth chamber) can result in increased pressure inside the tooth 10. Also, the elevation at which the waste fluid is discharged with respect to the tooth can cause static pressures inside the tooth 10.

(ii) Examples of Vented Fluid Platforms

Examples of a vented fluid platform include controlled systems where the inlet fluid flow rate and exit fluid flow rate may, but need not be, substantially the same. The two flow rates may in some cases, or for some time periods, be substantially the same. The fluid platform may include one or more "vents" that permit fluid to leave the tooth chamber 65, which can reduce the likelihood of an unsafe or undesired increase in fluid pressure (e.g., pressure at the periapical region). In some vented fluid platforms, the inlet and outlet flow rates may be driven by independent driving forces. For example, in some implementations, the fluid inlet can be in fluid communication with and driven by a pressure pump, while a fluid outlet can be in fluid communication with and controlled via an evacuation system (e.g., a suction or vacuum pump). In other implementations, the fluid inlet or outlet can be controlled with a syringe pump. The pressures of the fluid inlet and the fluid outlet may be such that a negative net pressure is maintained in the tooth chamber 65. Such a net negative pressure may assist delivering the treatment fluid into the tooth chamber 65 from the fluid inlet.

In various embodiments described herein, the "vents" can take the form of a permeable or semi-permeable material (e.g., a sponge), openings, pores, or holes, etc. The use of vents in a controlled fluid platform may lead to one or more desirable advantages. For example, the evacuation system can collect waste fluid from the tooth chamber 65, as long as there is any available. If there is a pause in treatment (e.g. the time between treatment cycles), waste fluid flow may stop, and the evacuation system may start drawing air through the one or more vents to at least partially compensate for the lack of fluid supplied to the evacuation system, rather than depressurizing the tooth chamber 65. If the evacuation system stops working for any reason, the waste fluid may flow out through the one or more vents into the patient's mouth or onto a rubber dam (if used), where it can be collected by an external evacuation line. Therefore, the use of vent(s) can tend to dampen the effects of the applied pressure differential, and therefore may inhibit or prevent negative or positive pressure buildup inside the tooth. Certain embodiments of vented fluid platforms may provide increased safety since the system can be configured to maintain a safe operating pressure in the tooth, even when the operating parameters deviate from those specified. Also note that positive or negative pressure inside the tooth chamber 65 can exert some amount of force on the sealing material(s), and as such a stronger seal may be required to withstand such force in some cases. Possible advantages of some vented systems include that the vent(s) help relieve pressure increases (or decreases) inside the tooth, reduce or eliminate the forces acting on the sealing material(s), and therefore render the sealing more feasible and effective.

Figure 3A:
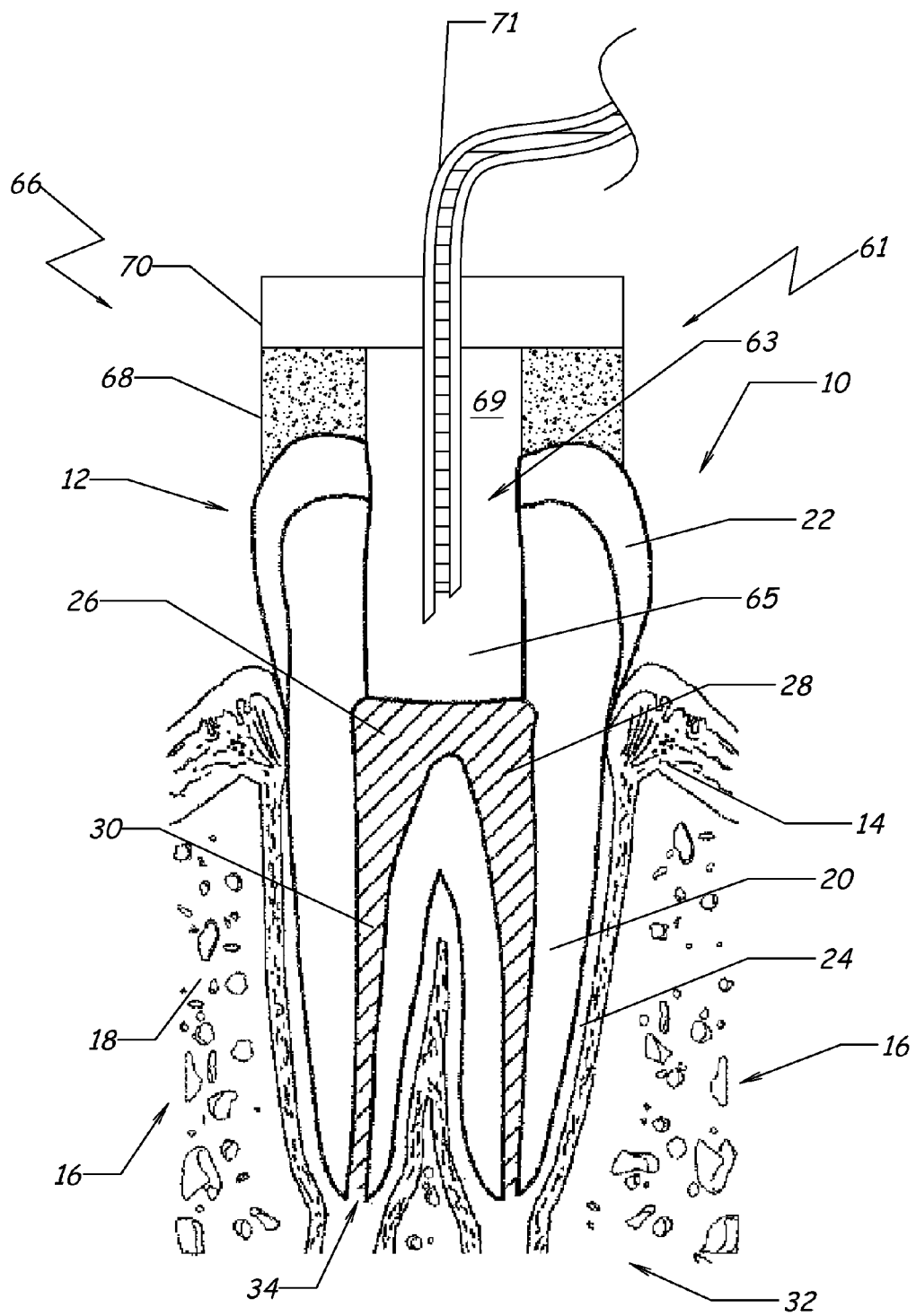
FIGS. 3A, 3B, and 3C schematically illustrate examples of fluid platforms that can be used in endodontic procedures.

FIG. 3A schematically illustrates an example of a fluid platform 61 that can be used in an endodontic procedure. In this example, the fluid platform 61 includes a fluid retainer 66 (e.g., cap 70 and flow restrictor 68) that can be generally similar to those described with reference to FIG. 2A. The fluid retainer 66 may be used to retain fluid in a chamber in the tooth 10. The fluid retainer 66 may include an internal (or inner) chamber 69 such that when the fluid retainer 66 is applied to the tooth, the internal chamber 69 and the tooth chamber 65 together form a fluid chamber 63. The fluid chamber 63 may be at least partially filled with fluid. In some advantageous embodiments, the fluid chamber 63 may be substantially or completely filled with fluid during a treatment procedure. The flow restrictor 68, which can function as the vent described above, may be used to permit fluid to flow from the chamber 63 (e.g., if the fluid pressure in the chamber becomes too large) and/or to inhibit flow of air into the chamber 63. The flow restrictor 68 can help retain fluid in the tooth chamber which may assist promoting fluid circulation in the tooth chamber, which may increase the effectiveness of irrigation or cleaning. The flow restrictor 68 can comprise a sponge (e.g., an open-cell or closed-cell foam) in some embodiments. An example of a flow restrictor 68 comprising an opening or port in the fluid platform 61 will be described with reference to FIG. 3B.

The fluid platform 61 also can include a fluid inlet 71 for delivering fluid to the chamber 63 in the tooth 10. The fluid inlet 71 can have a distal end that may be configured to be submerged in the fluid in the chamber 63 (after the chamber substantially fills with fluid). The distal end of the fluid inlet 71 may be sized and shaped so that it can be disposed in the pulp chamber 28 of the tooth 10, for example as shown in FIG. 3A. The distal end of the inlet 71 may be disposed within the pulp chamber 28 and above the entrances to the root canal spaces 30. Thus, in some such implementations, the fluid inlet 71 does not extend into the canal spaces. In other implementations, the distal end of the inlet 71 may be disposed in the fluid retained by the fluid retainer 66, but outside the pulp cavity 26 (e.g., above the occlusal surface of the tooth). In some cases, the distal end of the fluid inlet 71 can be sized/shaped to fit in a portion of a root canal space 30. For example, the distal end of the inlet 71 may comprise a thin tube or needle. In various implementations, the inlet 71 comprises a hollow tube, lumen, or channel that delivers the fluid to the tooth chamber 65. In other implementations, the fluid inlet 71 may be a liquid beam (e.g., a high-velocity liquid jet) that is directed into the tooth chamber 65. In some such embodiments, the liquid beam may deliver fluid to the tooth chamber 65 as well as generate pressure waves 67 in the fluid in the chamber 63.

In some embodiments, the fluid platform 61 can include a fluid introducer configured to supply fluid from a liquid source to the tooth chamber. The fluid introducer may comprise embodiments of the fluid inlet 71. In some implementations, the fluid introducer can also include a fluid line (or tubing) that provides fluidic communication between the fluid introducer and the liquid source. The fluid introducer may include a portion of a liquid jet device in some implementations.

The fluid inlet 71 may be in fluid communication with a fluid reservoir, supply, or source that provides the fluid to be delivered to the tooth via the inlet 71. The fluid may be delivered under pressure, for example, by use of one or more pumps or by using a gravity feed (e.g., by raising the height of the fluid reservoir above the height of the tooth chamber 65). The fluid platform 61 may include additional components (not shown in FIG. 3A) including, e.g., pressure regulators, pressure sensors, valves, etc. In some cases, a pressure sensor may be disposed in a tooth chamber 65, to measure the pressure in the tooth chamber 65 during treatment.

The flow of fluid from the inlet 71 may cause or augment fluid movement in the tooth chamber 65. For example, under various conditions of fluid inflow rate, pressure, inlet diameter, and so forth, the flow that is generated may cause (or augment) circulation, agitation, turbulence, etc. in the tooth chamber 65, which may improve irrigation or cleaning effectiveness in some cases. As described above, in some implementations a liquid jet device can be used to function as the inlet 71 and can deliver fluid to the tooth chamber 65 as well as generate pressure waves 67 in the chamber 65. Thus, the liquid jet device can serve as the pressure wave generator 64 and the fluid inlet 71 in such implementations. The fluid from the liquid jet (as well as its conversion to a spray if an impingement plate is used) can induce circulation in the tooth chamber 65. The flow of fluid from the inlet 71 can be used for a number of processes such as irrigation, cleaning, or disinfecting the tooth.

Figure 3B:
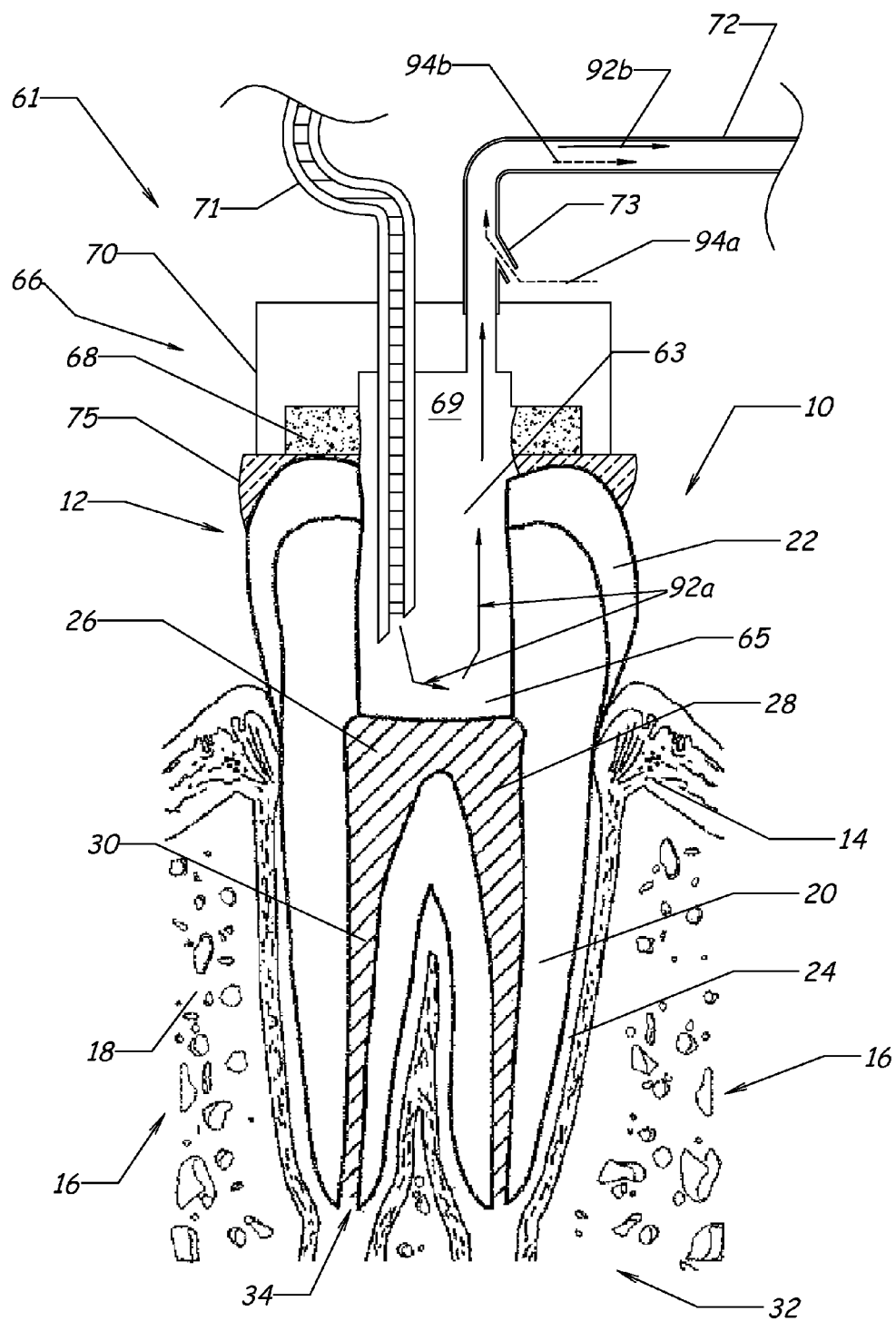

FIG. 3B schematically illustrates another example of a fluid platform 61 that can be used in an endodontic procedure. In this example, the fluid platform 61 comprises the fluid retainer 66, the fluid inlet 71, and a fluid outlet 72 configured to remove fluid from the tooth chamber 65. In the illustrated embodiment, the fluid retainer 66 comprises the cap 70 that can be applied or attached to a tooth seal formed on the tooth (a tooth seal 75 will be described below with reference to FIGS. 13B and 13C). An (optional) flow restrictor 68 comprising elastic material (e.g., a sponge or semi-permeable material) can be disposed within the gap to assist in providing a substantially water tight seal between the cap 70 and the tooth seal 75. The substantially water tight seal helps retain fluid within the tooth chamber 65 during treatment and may also inhibit ambient air from entering the tooth chamber 65 during treatment.

In some implementations the fluid outlet 72 functions passively, for example, the fluid moves through the outlet 72 because of capillary forces, gravity, or a slight overpressure created in the tooth. In other implementations, the fluid outlet 72 is actively pumped, and the fluid can be transferred using a pump, suction, or other device that draws fluid out through the outflow conduit. In one example, the fluid outlet 72 comprises a suction line operated under partial vacuum pressure to suction out fluid and may be connected to the suction system/vacuum lines commonly found in a dental office.

As described above with reference to FIG. 3A, fluid may be at least partially retained in the fluid chamber 63, which can comprise the internal chamber 69 in the fluid retainer 66 and the tooth chamber 65. The fluid chamber 63 may be at least partially filled with fluid. In some advantageous embodiments, the fluid chamber 63 may be substantially or completely filled with fluid during a treatment procedure. During treatment, the fluid inlet 71 and the fluid outlet 72 can be in fluid communication with fluid retained in the fluid chamber 63. In the embodiment illustrated in FIG. 3B, both the fluid inlet 71 and the fluid outlet 72 are in fluid communication with the fluid in the fluid chamber 63, and fluid can flow into the tooth from the fluid inlet 71 (solid arrowed lines 92a in FIG. 3B) and be removed from the tooth via the fluid outlet 72 (solid arrowed line 92b in FIG. 3B). Note that in this embodiment, there is a single fluid chamber 63 in which both fluid delivered from the inlet 71 and fluid removed from the outlet 72 can directly fluidly communicate (e.g., without passing through a valve, a tube, a needle, etc.). The delivery of fluid into the tooth chamber 65 via the fluid inlet 71 can cause a circulation in the tooth chamber 65 (see, e.g., arrowed lines 92a).

In this example, the fluid platform 61 comprises an additional flow restrictor in the form of a vent 73 that is disposed along the fluid outlet 72. The vent 73 can permit fluid from the tooth chamber 65 to flow out of the vent 73, for example if the fluid pressure becomes too large in the chamber. The vent 73 can act as a relief valve to inhibit over-pressurization of the tooth chamber 65.

In some embodiments, the vent 73 comprises a directionally biased valve that permits fluid to leave the tooth chamber 65 but inhibits ambient air from entering the tooth chamber 65. For example, the vent 73 may comprise one or more one-way (or check) valves. A one-way valve may have a cracking pressure selected to permit fluid to leave the tooth chamber 65 when the fluid pressure in the tooth chamber 65 exceeds a pressure threshold (e.g., about 100 mmHg in some cases). In other embodiments, a one-way valve may be used to permit ambient air to flow into the tooth chamber 65 when the pressure differential between ambient conditions and the pressure in the tooth chamber 65 is sufficiently large. For example, the cracking pressure of such a one-way valve may be selected such that if the fluid pressure in the chamber is less than a net (negative) threshold (e.g., the tooth chamber is under-pressurized), the valve will open to permit ambient air to flow into the fluid retainer 66. Such ambient air may be suctioned out of the fluid retainer 66 via a fluid outlet 72 (e.g., the one-way valve may be disposed along the fluid outflow line). In some embodiments, the vents 73 comprise a one-way valve to permit fluid to leave the fluid retainer 66 (while inhibiting ambient air from entering), and a one-way valve to permit ambient air to enter the fluid retainer 66. The cracking pressures of these two one-way valves may be selected so that in a desired pressure range, fluid is retained in the tooth chamber 65 and ambient air is inhibited from entering the tooth chamber 65. For example, the pressure range in the tooth may be between about −100 mmHg and +100 mmHg.

In other embodiments, the vent 73 may be configured to permit air to enter the fluid outlet 72 and be entrained with fluid removed from the tooth chamber 65. For example, as shown in FIG. 3B, the vent 73 may be positioned and oriented such that ambient air flows into the fluid outlet 72 in the direction of the fluid flow in the outlet 72 (see, e.g., dashed arrowed line 94a). In such embodiments, the flow in the fluid outlet 72 includes both fluid from the tooth chamber 65 (see, e.g., solid arrowed line 92b) and ambient air (see, e.g., dashed arrowed line 94b). In some implementations, the vent 73 is disposed near the entry point of fluid into the outlet 72, e.g., within a few millimeters, which may make it easier for fluid to flow from the tooth chamber 65 if the pressure therein rises too high. In various embodiments, a plurality of vents 73 may be used such as, two, three, four, or more vents. The vents 73 may be sized, shaped, positioned, and/or oriented to allow fluid to flow from the tooth chamber 65 while inhibiting air from entering the tooth chamber 65.

The example systems shown in FIGS. 3A and 3B can assist in inducing fluid circulation in the tooth chamber 65 due to the inflow of fluid from the fluid inlet 71 and/or the removal of fluid from the fluid outlet 72 (if present). The example systems may also advantageously have patient safety features. For example, if the fluid outlet 72 is blocked (e.g., a suction tube is kinked or the suction ceases to function), the flow of fluid into the tooth chamber 65 from the inlet 71 can lead to increasing fluid pressures, which can lead to the level of fluid rising up into the outlet 72. The flow restrictor 68 (e.g., a sponge or a vent) can relieve the fluid pressure by allowing fluid to leave the tooth chamber 65 (e.g., by flowing through the sponge or leaking out the vent). As another example, if the fluid inlet 71 is blocked (or ceases to function), the fluid outlet 72 may remove the fluid from the tooth chamber 65 and may lead to increasingly lower pressures in the tooth chamber 65. The flow restrictor 68 can tend to keep the pressure in the tooth 10 at a safe or desirable level by allowing ambient air to flow into the fluid outlet 72 to at least partially alleviate the depressurization of the tooth chamber 65. Thus, by allowing the pressure in the tooth chamber 65 to remain within safe or desirable bounds (e.g., above a lower pressure threshold and below an upper pressure threshold), certain such embodiments may provide advantages over closed fluid containers that do not include some form of fluid restrictor or pressure relief valve.

Accordingly, certain embodiments of the fluid platform 61 may be at least partially open to the ambient environment (e.g., via the flow restrictor 68) and may substantially allow the pressure in the tooth chamber 65 to self-regulate. An additional advantage of certain such embodiments can be that pressure regulators, pressure sensors, inlet/outlet control valves, etc. need not be used to monitor or regulate the pressure in the tooth chamber 65 under treatment, because the self-regulation of the flow restrictor 68 permits the pressure to remain within desired or safe levels. In other embodiments, pressure regulators, pressure sensors, and control valves may be used to provide additional control over the fluid environment in the tooth. For example, pressure sensor(s) could be used to measure pressure along a fluid inlet 71 or a fluid outlet 72, in a portion of the tooth chamber 65, etc. In yet other embodiments, a temperature sensor or temperature controller may be used to monitor or regulate the temperature of the fluid in the fluid inlet 71 or a fluid outlet 72, in the tooth chamber 65, etc.

(iii) Examples of Systems for Analyzing Fluid Leaving the Tooth

Substantially anything cleaned out from the pulpal chamber (in teeth that have pulpal chambers) and canals of a tooth (including pulp, debris, organic matter, calcified structures, etc.) can be monitored to determine the extent or progress of the tooth cleaning or to determine when the tooth becomes substantially clean. For example, when substantially no more pulp, calcified structures, organic matter, inorganic matter, and/or debris comes out of the tooth, the tooth may be substantially clean, and the system may provide a signal (e.g., audible/visible alarm, appropriate output on a display monitor) to the operator to stop the procedure. Such monitoring of the output from the tooth chamber 65 can be used with any of the embodiments described herein, including with open, closed, or vented fluid platforms.

Figure 3C:
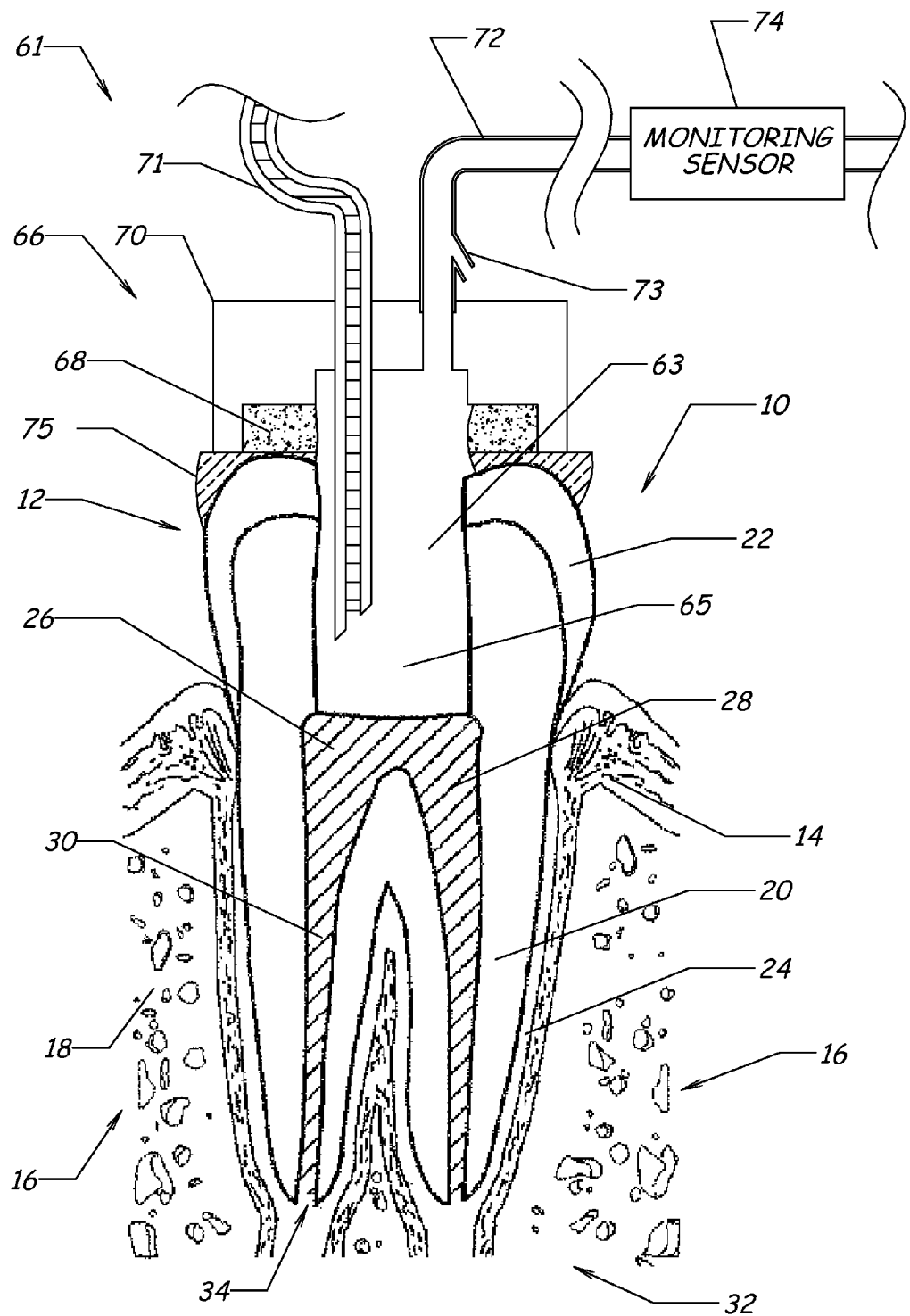

FIG. 3C schematically illustrates an example of a fluid platform 61 in which the fluid outlet 72 is in fluid communication with an optional monitoring sensor 74. The monitoring sensor 74 can monitor or analyze one or more properties of the fluid removed from the tooth 10. The monitoring sensor 74 can include an optical, electrical (e.g., resistive), chemical, and/or electrochemical sensor. Monitoring sensors 74 can include a liquid particle counter (e.g., configured to determine a range of particle sizes in the fluid), a liquid or gas chromatograph, a flame ionization detector, photoionization detector, a thermal conductivity detector, a mass spectrometer, etc. The monitoring sensor 74 can use elemental analysis techniques to determine properties of the fluid.

In some embodiments, the monitoring sensor includes an optical sensor such as, e.g., a photometric sensor, a spectroscopic sensor, a color sensor, or a refractive index sensor. Optical properties in any part of the electromagnetic spectrum can be measured (e.g., ultraviolet, visible, infrared, etc.). For example, an optical sensor can include a light source (e.g., an LED) and a light detector (e.g., a photodiode) disposed relative to a fluid (e.g., fluid in the fluid outlet 72). The light source can emit light into the fluid and the light detector can measure the amount of light reflected from or transmitted through the fluid in the fluid outlet 72. At early stages of an endodontic treatment, the fluid from the tooth may contain substantial amounts of pulpal matter such that the fluid is murky and reflects, and does not transmit, much light. As the treatment proceeds, the amount of pulpal matter in the fluid decreases, and the reflectivity may correspondingly decrease (or the transmittivity may increase). When relatively little additional pulpal matter is contained in the fluid from the tooth, the fluid in the outlet 72 may be substantially clear, and the reflectivity or transmittivity may reach a threshold value appropriate for fluid without pulpal matter (e.g., for clear water). The decrease of pulpal matter in the fluid outflow can be used as an indicator that the treatment is substantially complete or that the tooth chamber is substantially clean.

In some embodiments, a second monitoring sensor 74 is disposed upstream of the fluid platform 61 and can be used to provide a baseline measurement of properties of the fluid prior to entering the tooth chamber 65. For example, the threshold value may be based, at least in part, on the baseline measurement. Thus, in some embodiments, when the sensed property of the fluid property leaving the fluid platform is substantially the same as the sensed property of the fluid entering the fluid platform, it can be determined that the tooth treatment is substantially complete.

In various embodiments, the monitoring may be done continuously during the treatment or may be done at discrete times during the treatment. The monitoring sensor 74 may be configured to measure an amount of carbon in the fluid, e.g., total organic carbon (TOC), total inorganic carbon, or total carbon. The amount of total inorganic carbon may reflect removal of hard structures such as calcified tissues, pulp stone, or dentin (e.g., tertiary dentin) during the treatment. The monitoring sensor 74 may measure a property associated with removal of soft tissue (e.g., pulp, bacteria), hard tissue (e.g., pulp stone or calcified tissue), or both.

Thus when a property measured by the monitoring sensor 74 reaches a threshold value, the system can alert the operator that the treatment is complete (e.g., little additional organic or inorganic material is being removed from the tooth). In some embodiments, a change in a measured property (e.g., a change between measurements at two different times) can be monitored, and when the change is sufficiently small (indicating that a threshold or plateau has been reached), the system can alert the operator that treatment is complete.

In some implementations, feedback from the monitoring sensor 74 can be used to automatically adjust, regulate, or control one or more aspects of the endodontic treatment. For example, a tooth irrigation device, a tooth cleaning device, a fluid source, a fluid platform, a pressure wave generator, etc. may be adjusted based on the feedback to automate some or all of the treatment. In one implementation, the concentration of a tissue dissolving agent (e.g., sodium hypochlorite) or a fluid flow rate can be adjusted based at least in part on feedback for a monitored amount of organic material in the tooth outflow. For example, if the amount of organic matter flowing from the tooth remains relatively high, the concentration of the tissue dissolving agent in the treatment fluid or the flow rate of the treatment fluid may be increased. Conversely, if the amount of organic matter decreases quickly, the tooth cleaning may be nearly complete, and the concentration of the tissue dissolver or the fluid flow rate may be decreased. In some such implementations, if the organic matter has decreased sufficiently, the system may switch to a different solute (e.g., a decalcifying agent) to begin a different phase of the treatment. In another implementation, feedback from the monitoring sensor 74 can be used to adjust a pressure wave generator, for example, by increasing or decreasing the time the generator is activated (or deactivated). In some implementations using feedback, a proportional-integral-derivative (PID) controller or a fuzzy logic controller can be used to regulate or control aspects of the endodontic treatment.

(iv) Additional Features of Some Controlled Fluid Platforms

In some methods, little or substantially no treatment solution is injected through the apex 32 of the tooth 10 into the periapical region of the tooth 10 (the tissues that surround the apex 32 of the tooth). To limit injection of fluid into the periapical region, some embodiments are configured such that the pressure created inside the tooth and communicated to the apex 32 of the tooth 10 is equal to or lower than a pressure in the periapical region of the tooth 10 that is tolerable by patients. In various embodiments, the fluid platform 61 is configured such that the pressure created at the apex 32 of the tooth 10 (or in a portion of the tooth chamber such as, e.g., the pulp chamber 28) is below an upper value of about 500 mmHg, about 300 mmHg, about 200 mmHg, about 100 mmHg, about 50 mmHg, about 20 mmHg, or some other value. In some implementations, it may be desired that the apical pressure or tooth chamber pressure be above a lower value of about −1000 mmHg, about −500 mmHg, about −300 mmHg, about −200 mmHg, about −100 mmHg, about −50 mmHg, about 0 mmHg, or some other value. By selecting the size, number, and/or arrangement of fluid restrictors (e.g., sponges, vents, etc.), various systems can limit the apical pressure or the tooth chamber pressure to the foregoing values or ranges, as desired.

In some embodiments, it may be beneficial for the pressure at the apex 32 of the tooth 10 to be negative (e.g., lower than the pressure in the apical area). A negative pressure may allow inflamed bacteria, debris, and tissue (such as that found in a periapical lesion) to be suctioned out through the apex 32 of the tooth 10 and out of the mouth. It may be advantageous if the negative pressures created in the apex 32 of the tooth 10 are not too high (in magnitude) as this may induce pain in the patient. In one embodiment, the pressure created at the apex 32 of the tooth 10 is above about −1000 mmHg. In another embodiment, the pressure created at the apex 32 of the tooth 10 is above other values such as, e.g., about −600 mmHg, −500 mmHg, −250 mmHg, or some other value.

In some embodiments, substantially little or no treatment fluid, bacteria, tissue, debris, or chemicals enters the mouth during the procedure (e.g., substantially no leak from the handpiece and no leak between the handpiece and the tooth during the procedure), which may improve fluid management during the procedure. Spilling little or no material into the mouth during the procedure reduces the need to suction and remove waste fluid and material during the procedure. Accordingly, an assistant may not be needed during the procedure, which may simplify logistics and reduce manpower. Bacteria and debris removed from the infected tooth during the procedure should be avoided from being spilled into the mouth of the patient—so removing such material via the fluid platform may improve the cleanliness or hygiene of the procedure. Further, many of the chemicals used during endodontic procedures (e.g., NaOCl, etc.) may be corrosive or irritating to oral/gum tissue and reducing the likelihood of or preventing them from entering the patient's mouth is therefore desirable. Also, many of the chemicals and solutions used during endodontic procedures taste bad; therefore, not spilling such materials in the mouth during a procedure greatly improves patient comfort.

Delivering substances such as chemicals, medicaments, etc. in the treatment solution reduces the likelihood or prevents having to add such substances intermittently during an endodontic procedure (e.g. adding NaOCl intermittently during a root canal procedure). Embodiments of the fluid platform can allow one or more substances to be added during the procedure and in some implementations, the fluid can be automatically removed (e.g., via the fluid outlet). Substance concentration can be controlled or varied during procedure. One substance can be flushed out before introducing another substance, which may prevent unwanted chemical interactions. Embodiments in which the fluid platform is a closed system allow the use of more corrosive substances that may not be beneficial if spilled into the patient's oral environment. Substantially continuous replenishing of substances can help chemical reactions occur and may reduce the requirement for high concentration of such chemicals.

In various embodiments, a controlled fluid platform can be configured for one or more of the following. The fluid platform can allow analysis of fluid leaving the tooth to determine when procedure is complete. The fluid platform can prevent overheating of the tooth (if the pressure wave generator 64 or other components generate heat) by irrigating the tooth chamber 65 with fluid through the fluid inlet 71.

The fluid platform can reduce or prevent air (e.g., gas) from being introduced into the tooth chamber 65, which may lower the effectiveness of irrigation, pressure waves, or cavitation. A controlled fluid platform can allow cleaning action/energy to be more effective during a procedure, e.g. fewer losses through mechanisms such as splashing, which removes both fluid mass and fluid momentum from the tooth chamber (which otherwise could provide circulation). The fluid platform can allow teeth to be treated in any orientation in space (e.g. upper or lower teeth may be treated while the patient reclines in a dental chair). The fluid platform can allow macroscopic circulation within the tooth to, for example, effectively remove tissue and debris from canals and canal spaces and/or effectively replenish new treatment solution.

C. Examples of Combinations of Pressure Wave Generators and Fluid Platforms

Figure 4A:
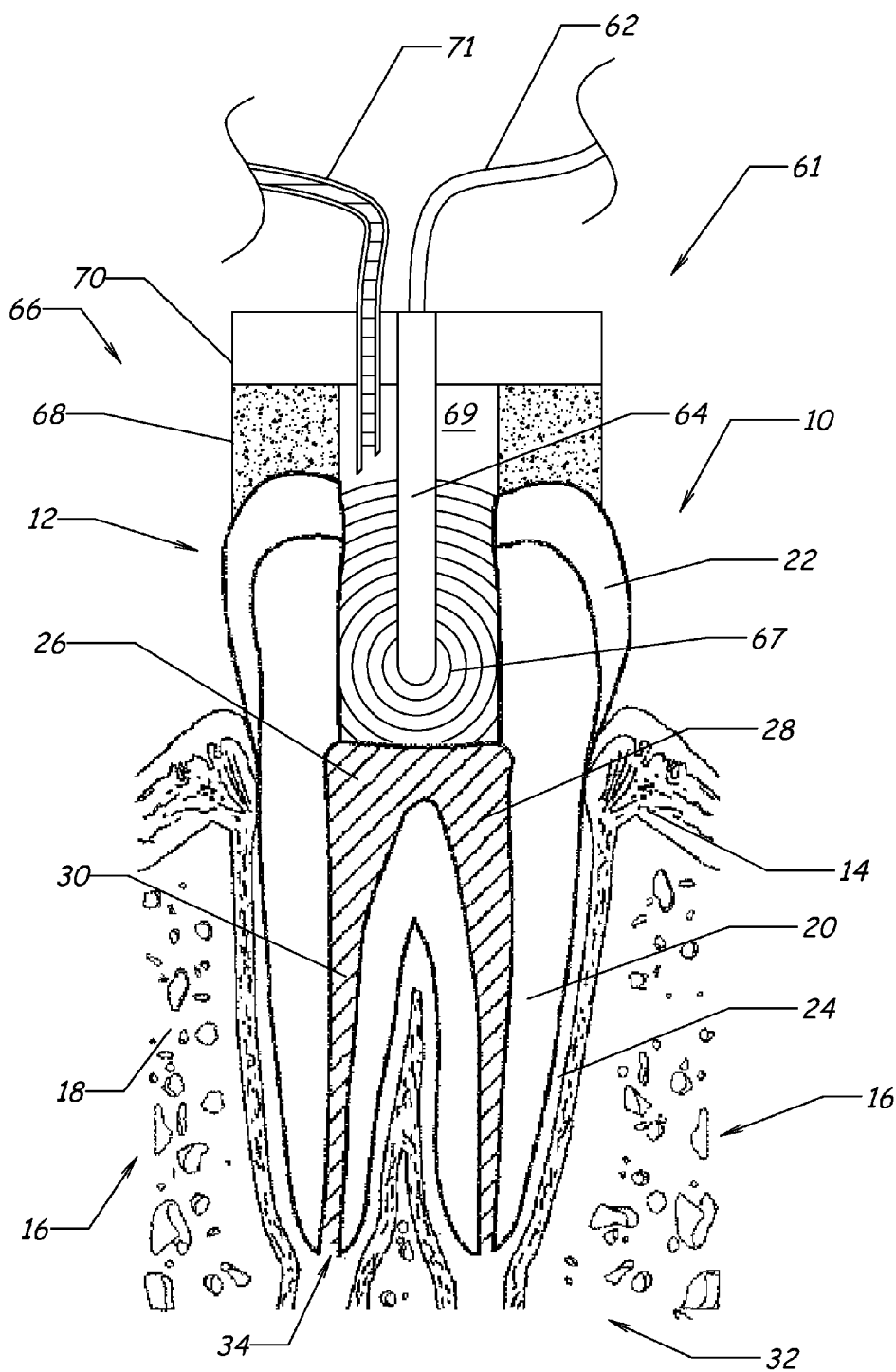
FIGS. 4A, 4B, 4C, and 4D schematically illustrate examples of systems for endodontic procedures.

In various embodiments, systems and methods may utilize some or all of the features of the apparatus shown in FIGS. 2, 3A, 3B, and 3C in various combinations. These embodiments may include additional or different features as well. For example, FIG. 4A schematically illustrates an example system for cleaning a tooth using pressure waves 67. The system comprises a fluid retainer 66, a pressure wave generator 64, and a fluid inlet 71. In some embodiments, the pressure wave generator 64 may deliver fluid to the tooth chamber 65 (e.g., a liquid jet) in combination with the fluid delivered from the fluid inlet 71. In some such embodiments, the fluid inlet 71 may deliver fluid from a different fluid source than is used to provide the fluid for the liquid jet. For example, the inlet 71 may deliver a tissue dissolving agent or an antiseptic or antibacterial solution, and the pressure wave generator 64 may deliver a beam of distilled water.

In other implementations, the pressure wave generator 64 may not act as a source of fluid, e.g., the pressure wave generator 64 may comprise an optical fiber delivering laser light energy to the tooth chamber 65 or a mechanical paddle or rotor. In such implementations, the fluid inlet 71 can be used to deliver fluid to the tooth chamber 65 so as to provide a fluid propagation medium for acoustic waves 67 generated by the pressure wave generator 64. Although the example system of FIG. 4A is shown as having a single fluid inlet 71 and a single pressure wave generator 64, this is for illustrative purposes, and in other embodiments, multiple fluid inlets 71 and/or pressure wave generators 64 can be used. For example, an optical fiber delivering light energy could be used in conjunction with a mechanical stirrer to provide pressure waves 67 and circulation in the fluid chamber 63. In another example, the optical fiber could be used with a liquid jet device.

The distal end of the pressure wave generator 64 may be submerged in fluid in the tooth chamber during at least a portion of the endodontic procedure. For example, the distal end of the pressure wave generator 64 may be disposed in the tooth chamber 65 while there is little or not liquid in the tooth chamber. Fluid can be added to the tooth chamber via the fluid inlet 71 such that a fluid level rises above the distal end of the generator 64. The pressure wave generator 64 may then be activated for at least a portion of the endodontic procedure. During other portions of the procedure, the pressure wave generator 64 may be inactive and/or disposed above the fluid level in the tooth chamber 65.

Figure 4B:
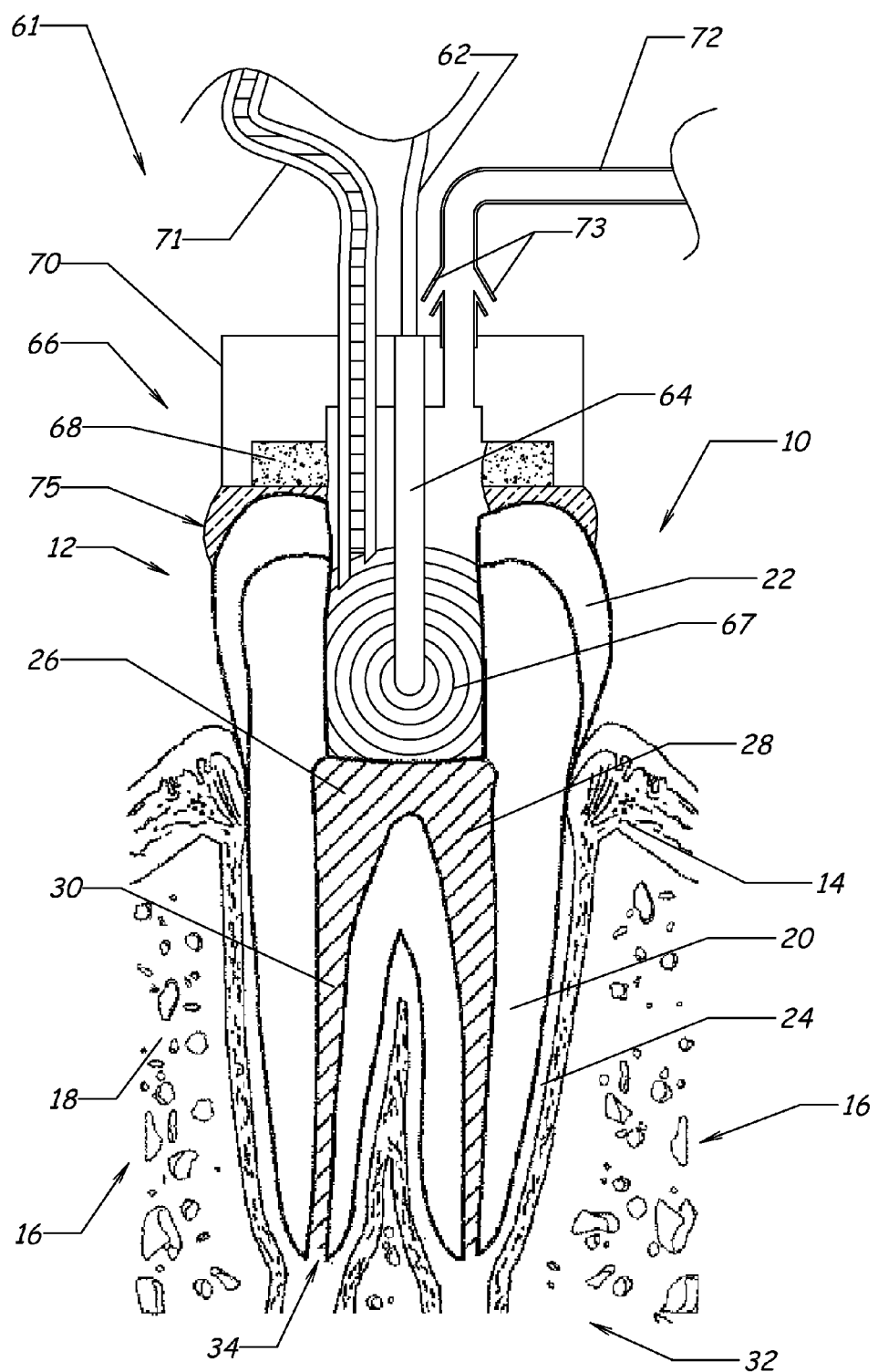

FIG. 4B schematically illustrates another example system for cleaning a tooth 10 using pressure waves 67. In this example, the system includes the fluid retainer 66, the pressure wave generator 64, and the fluid outlet 72, which includes two vents 73. The use of multiple vents 73 may be advantageous in cases where one of the vents 73 becomes blocked. Also, the dental practitioner may apply a suction tube to one of the vents to assist removal of fluid from the tooth chamber 65, while the other vent(s) remain available to inhibit under-pressurization or overpressurization of the tooth chamber 65.

In the example shown in FIG. 4B, a tooth seal 75 is applied to a perimeter of a crown 12 of the tooth 10. As will be further described herein, the tooth seal 75 may be formed from a substantially pliable or semi-flexible material that sets in a relatively short time by itself or with curing. The upper surface of the tooth seal 75 can be made substantially flat after application and removal of a flat plate to the upper surface (see, e.g., FIGS. 13B-14B). The upper surface of the tooth seal 75 advantageously may provide a substantially flat working surface upon which the cap 70 of the fluid retainer 66 may be disposed or attached so that fluid in the tooth chamber 65 is inhibited from leaking out. FIG. 4B also shows an (optional) elastomeric material disposed under the cap 70, which can help increase the water-tight seal between the cap 70 and the tooth seal 75.

Figure 4C:
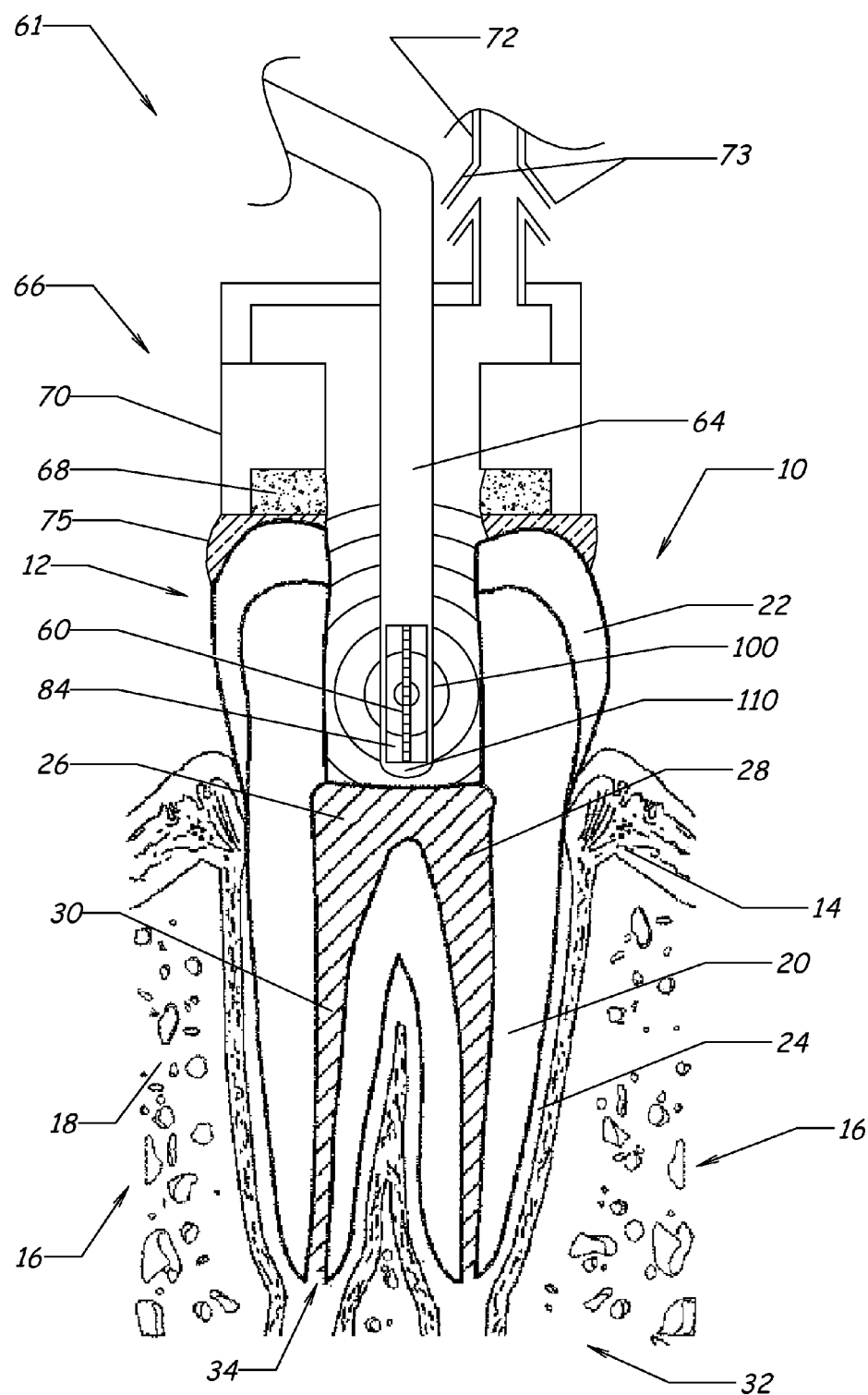

FIG. 4C shows another example system for cleaning a tooth 10 using a pressure wave generator 64. In this example, the pressure wave generator 64 comprises a liquid jet device having a guide tube 100 with a distal end that extends into the pulp cavity 26 of the tooth 10. In this example, the guide tube 100 comprises a channel or lumen 84 along which the liquid jet 60 can propagate until the jet 60 strikes an impingement plate 110 at the distal end. The impact of the jet 60 on the impingement plate 110 creates a spray of liquid that can exit one or more openings at the distal end of the guide tube 100. A surface of the impingement plate 110 may reverberate due to the impact of the jet. The distal end of the guide tube 100 (including the openings) can be submerged below the surface of fluid retained in the tooth 10 by the fluid retainer 66. The impact of the jet 60 on the impingement surface 110 and/or the interaction of the jet or spray with the fluid in the tooth chamber 65 can create pressure waves 67 that may at least partially lead to effective tooth cleaning as described herein. In this example, the distal end of the guide tube 100 functions as a fluid inlet 71 to deliver the jet liquid to the tooth chamber 65 and as a pressure wave generator 64. This example system also includes a fluid outlet 72 with vents 73 to remove fluid from the tooth chamber 65 and to limit under-pressurization or overpressurization of the tooth chamber 65.

Figure 4D:
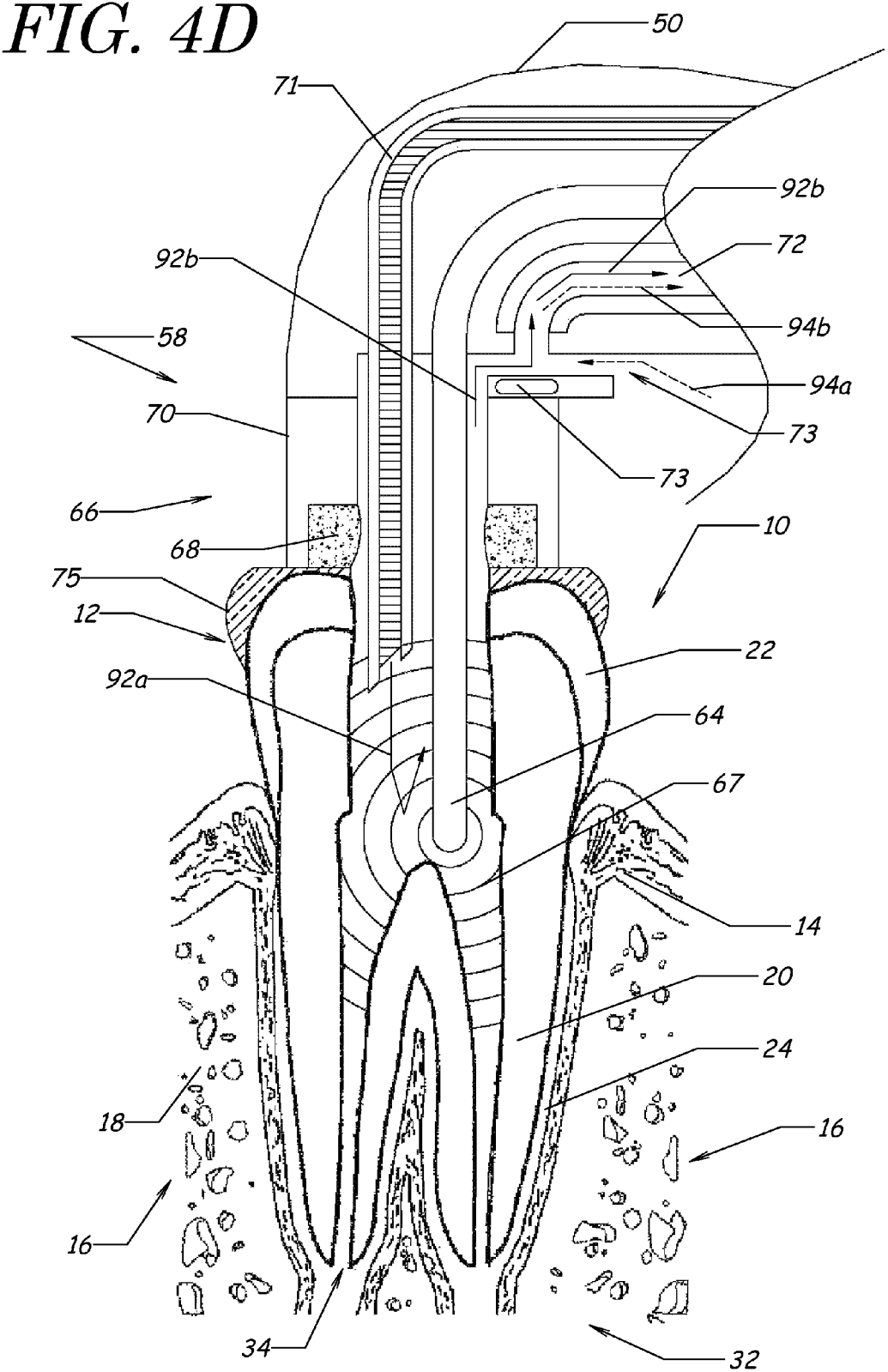

FIG. 4D shows another example system for cleaning a tooth 10 using a pressure wave generator 64. In this example, the system includes a handpiece 50 with a distal end 58 that can be applied or attached to a tooth seal 75 formed on the tooth 10. The distal end 58 includes the fluid retainer 66 (e.g., the cap 70). The handpiece 50 includes the fluid inlet 71, the fluid outlet 72, and the pressure wave generator 64. Portions of the fluid inlet 71 and the pressure wave generator 64 extend beyond the cap 70 so that they can be disposed in the pulp chamber 28.

The handpiece 50 shown in FIG. 4D also includes vents 73 that are in fluid communication with the fluid outlet 72. The vents 73 permit ambient air to be drawn into the fluid outlet 72 and to be entrained with fluid removed from the tooth 10. The vents 73 may help prevent the tooth chamber 65 from being depressurized (e.g., in the event that most of the fluid is withdrawn from the tooth chamber 65), because as the pressure in the tooth chamber 65 decreases, air can be drawn in from the vents 73 rather than from the tooth chamber 65. The vents 73 may also help prevent the tooth chamber 65 from being over-pressurized (e.g., in the event that the fluid outlet 72 ceases to remove fluid), because as the fluid pressure in the tooth increases, fluid can flow out of the vents 73 rather than being retained in the tooth chamber 65. The size, shape, and/or configuration of the vents 73 and/or their locations with respect to the tooth chamber and/or the fluid outlet line 72 can be selected so that air is inhibited from entering the vents 73 and passing to the tooth chamber 65, where such air may decrease the effectiveness of acoustic cavitation. Further details regarding vents will be provided with reference to FIGS. 12A and 12B. One, two, three, four, or more vents may be used in various embodiments.

FIGS. 2-4D are intended to illustrate various example systems and combinations of components and features that can be used in various implementations for endodontic treatment. The example systems illustrated in FIGS. 2-4D are not intended to limit the scope of the disclosure. All possible variations and combinations of the components shown and described with respect to FIGS. 2-4D (and the other figures to be described below) are contemplated.

(i) Additional Features of Some Fluid Platforms and Pressure Wave Generators

Some dental procedures require instrumentation (e.g., endodontic files) to be inserted in the canals, which may not be desirable. For example, instrumentation may create a smear layer in the canal or force organic matter out the apex 32 of the tooth 10, and instrumentation may weaken the tooth. Also, for some teeth, not all portions of the root canal spaces can be instrumented because of canal curvature or complex canal geometries, thus inhibiting instrumentation from being introduced into some canals or from reaching the apex of the canal. Instrumentation going inside the canals may increase the chance of extrusion of fluid/debris through the apex. Thus, as described herein, embodiments of the fluid platform can allow pressure waves 67 to be generated in fluid retained in the pulp cavity 26. The pressure waves 67 may be used to clean the tooth without instrumentation in some treatments. In some embodiments, the methods and systems described herein can be used with instrumented methods. For example, endodontic files can be used to enlarge, shape, or clean root canals, and then a fluid platform may be applied to the tooth and used to circulate a treatment fluid (e.g., sodium hypochlorite solution) through the tooth chamber 65. A pressure wave generator 64 may be used to provide additional cleaning in the tooth chamber 65. Many variations and combinations of possible techniques are contemplated that can be used by a dental practitioner.

Embodiments of the disclosed apparatus and method may allow removal of calcified structures (such as, but not limited to, pulp stones, calcified tissue covering the canal orifices, etc), which may limit or prevent access to and visualization of canals. Clearing such calcified structures in the pulp chamber 28 can allow the system to find entrances to canals automatically. For example, an undetected Mesiobuccal 2 (MB2) canal may appear by itself in some treatment methods. Embodiments of systems that create pressure waves only in the canals (and not in the pulp chamber) may require that canals be found or even enlarged in advance.

In some embodiments, the pressure waves 67 generated in the pulp chamber 28 can also remove calcified tissues and structures (e.g., pulp stones, tertiary dentin, etc.) inside the root canals. In some embodiments, the pressure waves 67 generated in the pulp chamber 28 can be used to remove smear layer and debris in instrumented canals. In some embodiments, the pressure waves 67 generated can reach all or substantially all interior spaces of the tooth, e.g., substantially everything in contact with the fluid, including accessory canals, tubules, etc. In some embodiments, the pressure waves 67 can clean the pulp chamber and all canals simultaneously, without requiring entering the root canals. In some treatments, there is no need to find or locate the canals prior to the procedure. The pressure wave cleaning may be able to reach the apex 32 of the tooth and reach farther into canal spaces and tubules than other treatment methods (e.g., with endodontic files or an ultrasonic tip). Embodiments of the fluid platform can allow pressure waves 67 to be created in canals or to reach the canals via propagation through the fluid in the pulp cavity. Small probes can allow embodiments of the fluid platform to clean small canals, e.g., if the probes can be inserted into the canals. However, in some implementations, this may require the operator to find the canals prior to the procedure.

D. Examples of Treatment Fluids

The treatment fluid used in any of the systems and methods described herein may include sterile or distilled water, a medical-grade saline solution, an antiseptic, an antibiotic, a decalcifying solution or agent, a tissue-dissolving solution or agent, etc. The treatment fluid may include chemicals, medications, salts, anesthetics, bleaches, detergents, surfactants, irrigants, growth promoters, or any combination thereof. The fluid may include a disinfectant, an oxidizing solution/agent (e.g., hydrogen peroxide), a debriding solution/agent, a chelating solution/agent, a bactericide, a deodorant, and/or a tissue solvent. The treatment fluid can include endodontic solutions, solutes, or agents such as, e.g., sodium hypochlorite (NaOCl), ethylenediaminetetraacetic acid (EDTA), anolyte, chlorhexidine, calcium hydroxide, calcium hypochlorite, citric acid, boric acid, Dakin's solution, propylene glycol alginate (PGA), etc. The fluid may be acidic, neutral, or basic, and in some cases, the pH of the solution may be adjusted to provide a desired cleaning effect. The fluid may be changed during treatment, for example, by changing the fluid reservoir or source that supplies fluid to the fluid inlet or the liquid jet device (if used). In some treatments, a fluid comprising a tissue dissolver can be used during a cleaning phase of the treatment, and an irrigant can be used to flush the cleaned pulp tooth chamber. Combinations of the foregoing (or other) fluids can be used, for example, mixtures of solutions or a sequence of different applied solutions. The type(s) and/or concentration(s) of chemical(s) in the fluid can change during treatment. One example of a treatment solution is water or saline with about 0.3% to about 6% NaOCl.

In some cases, the treatment fluid may include small particles, abrasives, or biologically-active particles (e.g., biopowders), etc. The fluid may include nanoparticles (e.g., nanorods or nanoshells). For example, in some systems where the pressure wave generator comprises a laser device, the light energy delivered from the laser may excite the nanoparticles and lead to more efficient photo-induced cavitation or pressure wave generation.

As will be described below, the treatment fluid (and/or any of solutions added to the treatment fluid) can be degassed compared to normal liquids used in dental offices. For example, degassed distilled water may be used (with or without the addition of chemical agents or solutes).

(1) Examples of Possible Effects of Dissolved Gases in the Treatment Fluid

Figure 5A:
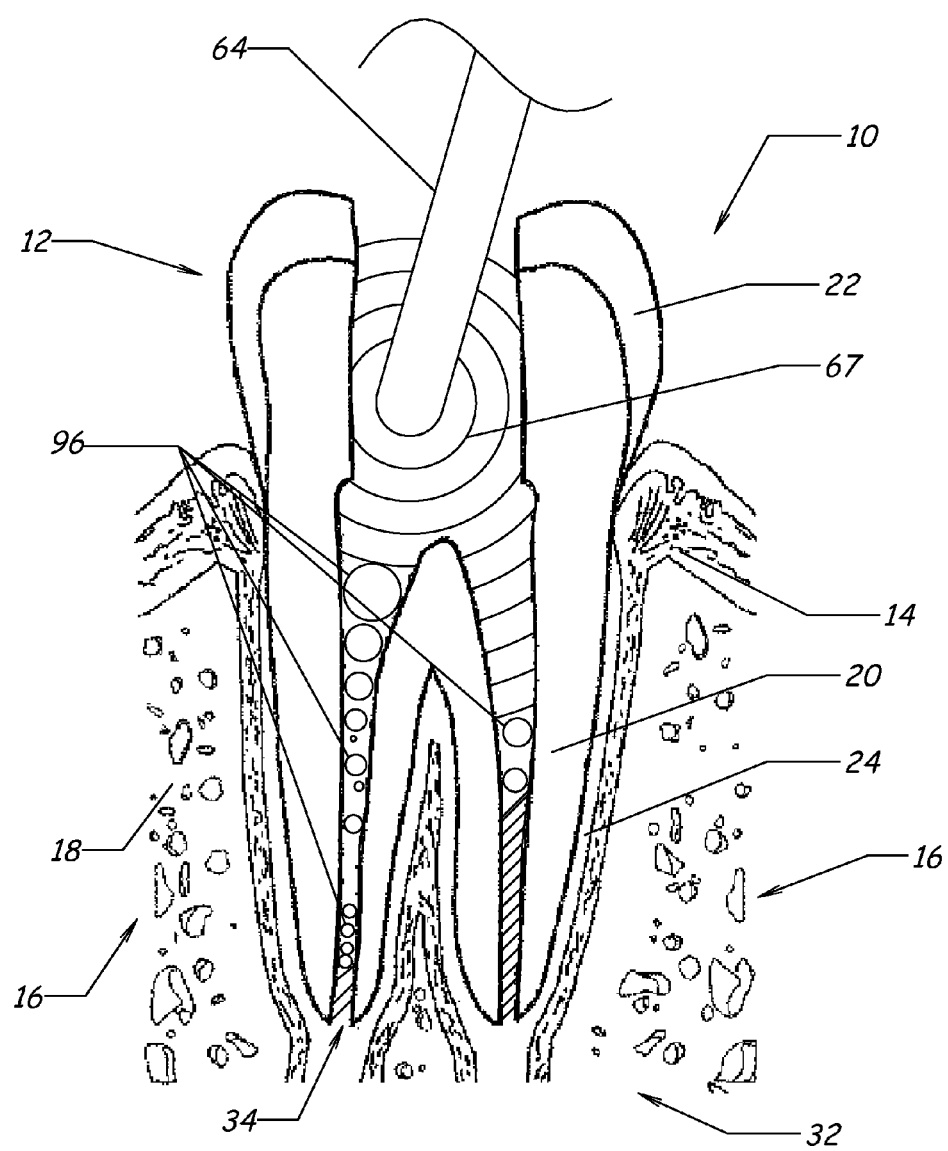
FIGS. 5A and 5B schematically illustrate examples of dental procedures in which the treatment fluid includes dissolved gases such that bubbles in the treatment fluid can come out of solution and block small passageways in the tooth.
Figure 5B:
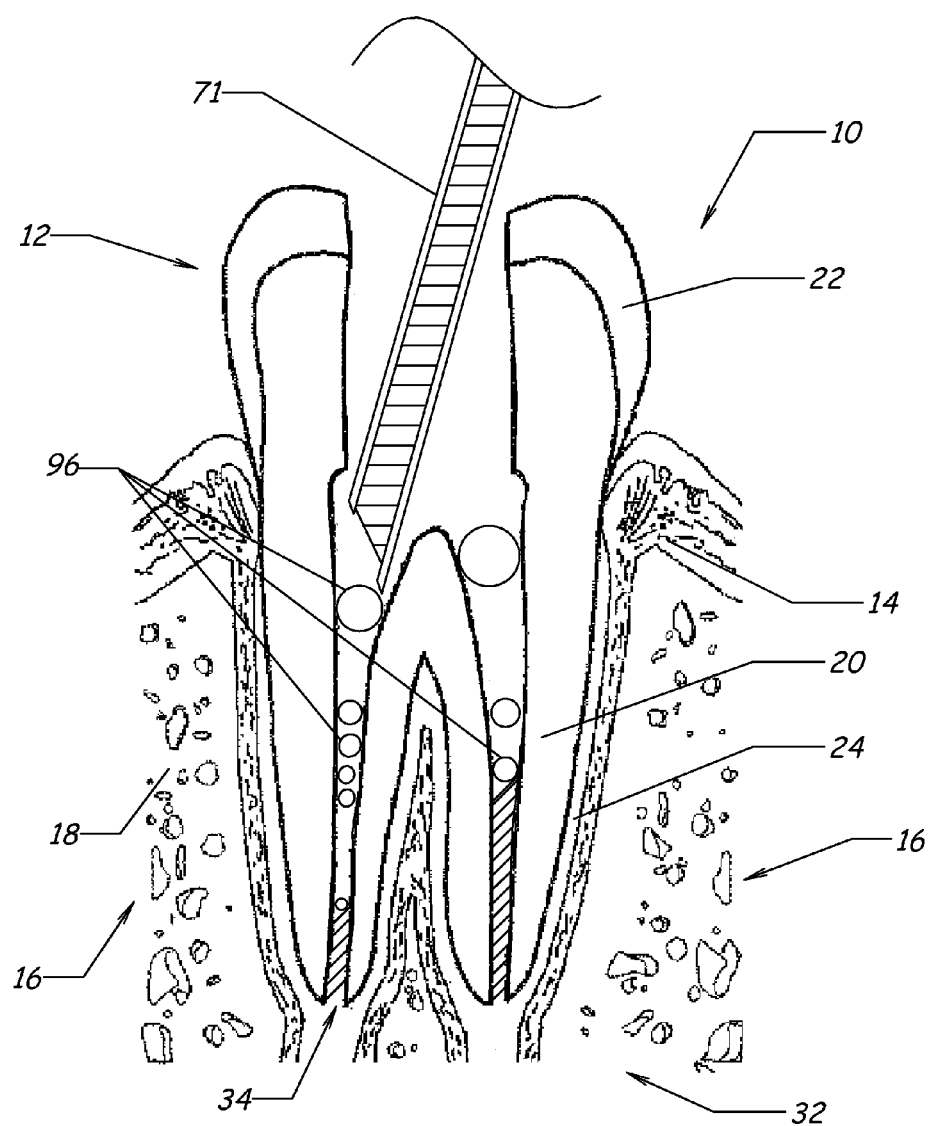

In some procedures, the fluid may include dissolved gases (e.g., air). For example, the fluids used in dental offices generally have a normal dissolved gas content (e.g., determined from the temperature and pressure of the fluid based on Henry's law). FIGS. 5A and 5B schematically illustrate examples of procedures in with a pressure wave generator 64 (FIG. 5A) and a fluid inlet 71 (FIG. 5B) operate with or in a fluid environment that contains a fluid with dissolved gases. The acoustic field of the pressure wave generator 64 and/or the flow or circulation of fluids in the tooth chamber 65 can cause some of the dissolved gas to come out of solution and form bubbles 96 as schematically illustrated in FIGS. 5A and 5B.

The bubbles 96 can block small passageways in the tooth 10 (e.g., small root canal spaces 30 or dentinal tubules) and such blockages can act as if there were a "vapor lock" in the small passageways. In some such procedures, the presence of bubbles 96 may at least partially block, impede, or redirect propagation of acoustic waves 67 past the bubbles 96 and may at least partially inhibit or prevent cleaning action from reaching, for example, the apical regions of the root canal (see, e.g., FIG. 5A). The bubbles 96 may block fluid flow or circulation from reaching the apical regions or tubules, which may prevent or inhibit a treatment solution from reaching these areas of the tooth 10 (see, e.g., FIG. 5B).

In certain endodontic procedures, cavitation is believed to play a role in cleaning the tooth. Without wishing to be bound by any particular theory, the physical process of cavitation inception may be, in some ways, similar to boiling. One possible difference between cavitation and boiling is the thermodynamic paths that precede the formation of the vapor in the fluid. Boiling can occur when the local vapor pressure of the liquid rises above the local ambient pressure in the liquid, and sufficient energy is present to cause the phase change from liquid to a gas. It is believed that cavitation inception can occur when the local ambient pressure in the liquid decreases sufficiently below the saturated vapor pressure, which has a value given in part by the tensile strength of the liquid at the local temperature. Therefore, it is believed, although not required, that cavitation inception is not determined by the vapor pressure, but instead by the pressure of the largest nuclei, or by the difference between the vapor pressure and the pressure of the largest nuclei. As such, it is believed that subjecting a fluid to a pressure slightly lower than the vapor pressure generally does not cause cavitation inception. However, the solubility of a gas in a liquid is proportional to pressure; therefore lowering the pressure may tend to cause some of the dissolved gas inside the fluid to be released in the form of gas bubbles that are relatively large compared to the size of bubbles formed at cavitation inception. These relatively large gas bubbles may be misinterpreted as being vapor cavitation bubbles, and their presence in a fluid may have been mistakenly described in certain reports in the literature as being caused by cavitation, when cavitation may not have been present.

In the last stage of collapse of vapor cavitation bubbles, the velocity of the bubble wall may even exceed the speed of sound and create strong shock waves inside the fluid. The vapor cavitation bubble may also contain some amount of gas, which may act as a buffer and slow down the rate of collapse and reduce the intensity of the shockwaves. Therefore, in certain endodontic procedures that utilize cavitation bubbles for tooth cleaning, it may be advantageous to reduce the amount of the dissolved air in the fluid to prevent such losses.

The presence of bubbles 96 that have come out of solution from the treatment fluid may lead to other disadvantages during certain endodontic procedures. For example, if the pressure wave generator 64 produces cavitation, the agitation (e.g. pressure drop) used to induce the cavitation may cause the release of the dissolved air content before the water molecules have a chance to form a cavitation bubble. The already-formed gas bubble 96 may act as a nucleation site for the water molecules during the phase change (which was intended to form a cavitation bubble). When the agitation is over, the cavitation bubble is expected to collapse and create pressure waves 67. However, cavitation bubble collapse might happen with reduced efficiency, because the gas-filled bubble may not collapse and may instead remain as a bubble. Thus, the presence of gas in the treatment fluid may reduce the effectiveness of the cavitation process as many of the cavitation bubbles may be wasted by merging with gas-filled bubbles. Additionally, bubbles 96 in the fluid may act as a cushion to damp pressure waves 67 propagating in the region of the fluid comprising the bubbles 96, which may disrupt effective propagation of the pressure waves 67 past the bubbles 96. Some bubbles 96 may either form inside the root canals 30 or be transferred there by the flow or circulation of fluid in the tooth. Once inside the canals 30, the bubbles 96 may be hard to remove due to relatively high surface tension forces. This may result in blocking the transfer of chemicals and/or pressure waves into the canals and therefore may disrupt or reduce the efficacy of the treatment.

(2) Examples of Degassed Treatment Fluids

Figure 5C:
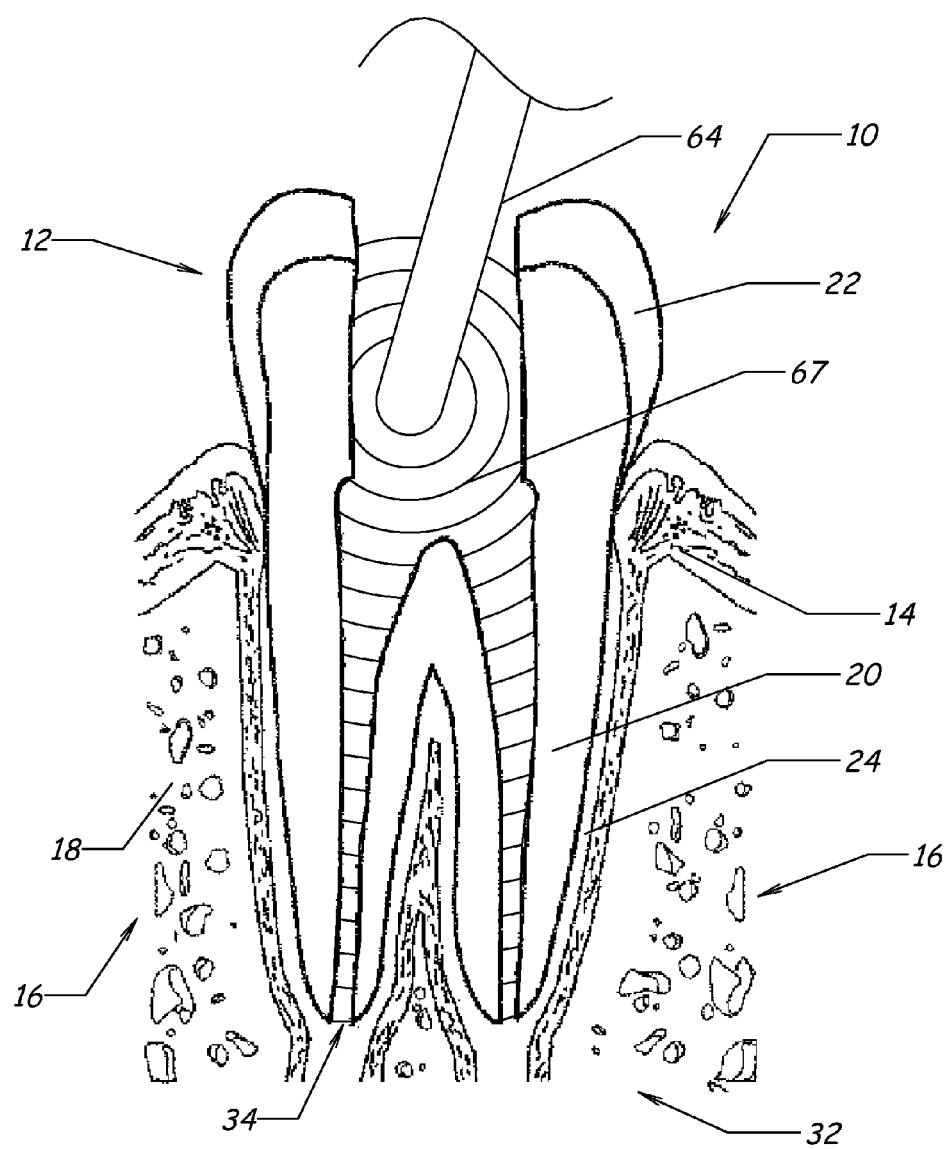
FIGS. 5C and 5D schematically illustrate examples of dental procedures in which the treatment fluid comprises a degassed fluid that has a reduced dissolved gas content (compared with the treatment fluid in the examples of FIGS. 5A and 5B) such that the passageways of the tooth are substantially free of bubbles released from the treatment fluid.
Figure 5D:
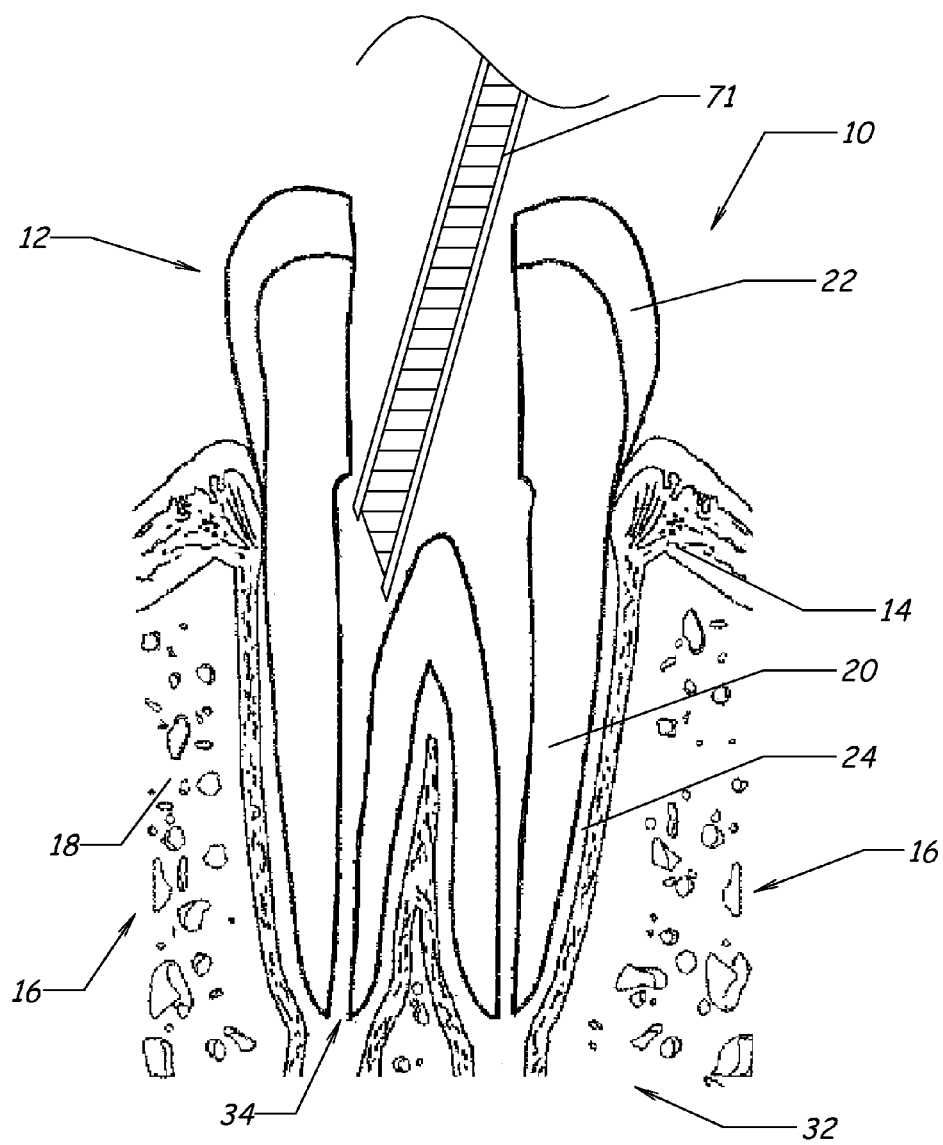

Accordingly, it may be advantageous in some systems and methods to use a degassed fluid, which may inhibit, reduce, or prevent bubbles 96 from coming out of solution during treatments as compared to systems and methods that use normal (e.g., non-degassed) fluids. FIGS. 5C and 5D schematically illustrate examples of dental procedures in which the treatment fluid has a reduced gas content (compared with the normal fluids in the examples of FIGS. 5A and 5B) such that the root canals 30 of the tooth 10 are substantially free of bubbles 96 that have come out of solution. As schematically illustrated in FIGS. 5C and 5D, acoustic waves 67 generated by the pressure wave generator 64 can propagate through the degassed fluid to reach and clean the apical regions 32 of the tooth 10 (FIG. 5C) and the degassed fluid from a fluid inlet 71 can reach the small root canal passages near the apex 32 of the tooth 10 (FIG. 5D). The degassed fluid may also be able to flow or penetrate dentinal tubules and clean matter from these hard to reach spaces. In some procedures, the degassed fluid may be able to penetrate spaces as small as about 500 microns, 200 microns, 100 microns, 10 microns, 5 microns, 1 micron, or smaller, because the degassed fluid is sufficiently gas-free that bubbles are inhibited from coming out of solution and blocking these spaces (as compared to use of fluids with normal dissolved gas content).

For example, in some systems and methods, the degassed fluid can have a dissolved gas content that is reduced when compared to the "normal" gas content of water. For example, according to Henry's law, the "normal" amount of dissolved air in water (at 25 C and 1 atmosphere) is about 23 mg/L, which includes about 9 mg/L of dissolved oxygen and about 14 mg/L of dissolved nitrogen. In some embodiments, the degassed fluid has a dissolved gas content that is reduced to approximately 10%-40% of its "normal" amount as delivered from a source of fluid (e.g., before degassing). In other embodiments, the dissolved gas content of the degassed fluid may be reduced to approximately 5%-50% or 1%-70% of the normal gas content of the fluid. In some treatments, the dissolved gas content may be less than about 70%, less than about 50%, less than about 40%, less than about 30%, less than about 20%, less than about 10%, less than about 5%, or less than about 1% of the normal gas amount.

In some embodiments, the amount of dissolved gas in the degassed fluid can be measured in terms of the amount of dissolved oxygen (rather than the amount of dissolved air), because the amount of dissolved oxygen may be more readily measured (e.g., via titration or optical or electrochemical sensors) than the amount of dissolved air in the fluid. Thus, a measurement of dissolved oxygen in the fluid may serve as a proxy for the amount of dissolved air in the fluid. In some such embodiments, the amount of dissolved oxygen in the degassed fluid can be in a range from about 1 mg/L to about 3 mg/L, in a range from about 0.5 mg/L to about 7 mg/L, or some other range. The amount of dissolved oxygen in the degassed fluid may be less than about 7 mg/L, less than about 6 mg/L, less than about 5 mg/L, less than about 4 mg/L, less than about 3 mg/L, less than about 2 mg/L, or less than about 1 mg/L.

In some embodiments, the amount of dissolved gas in the degassed fluid can be in a range from about 2 mg/L to about 20 mg/L, in a range from about 1 mg/L to about 12 mg/L, or some other range. The amount of dissolved gas in the degassed fluid may be less than about 20 mg/L, less than about 18 mg/L, less than about 15 mg/L, less than about 12 mg/L, less than about 10 mg/L, less than about 8 mg/L, less than about 6 mg/L, less than about 4 mg/L, or less than about 2 mg/L.

In other embodiments, the amount of dissolved gas may be measured in terms of air or oxygen percentage per unit volume. For example, the amount of dissolved oxygen (or dissolved air) may be less than about 5% by volume, less than about 1% by volume, less than about 0.5% by volume, or less than about 0.1% by volume.

The amount of dissolved gas in a liquid may be measured in terms of a physical property such as, e.g., fluid viscosity or surface tension. For example, degassing water tends to increase its surface tension. The surface tension of non-degassed water is about 72 mN/m at 20° C. In some embodiments, the surface tension of degassed water can be about 1%, 5%, or 10% greater than non-degassed water.

Figure 6A:
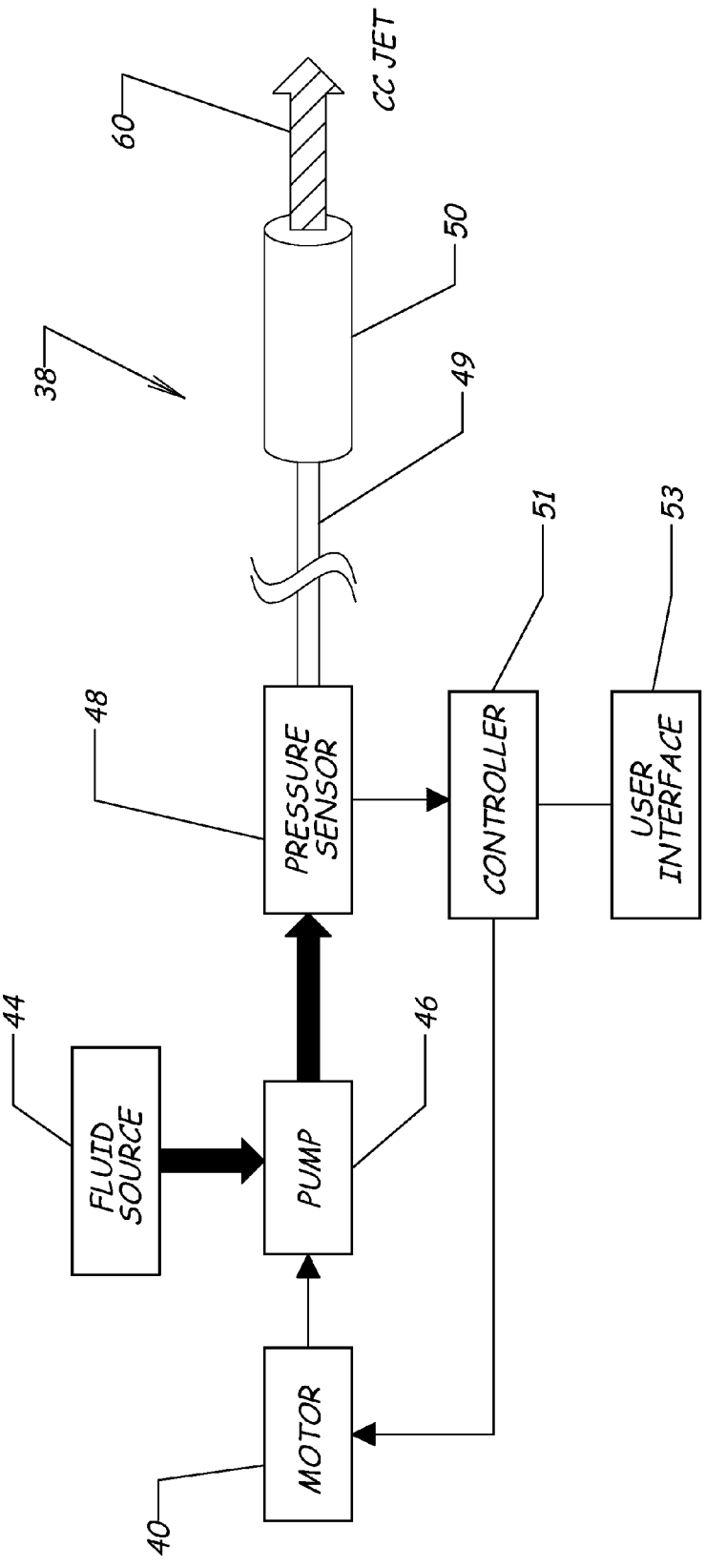
FIGS. 6A and 6B are block diagrams schematically illustrating embodiments of a system adapted to produce a high-velocity liquid jet (FIG. 6A) and to provide fluid to a fluid platform (FIG. 6B).
Figure 6B:
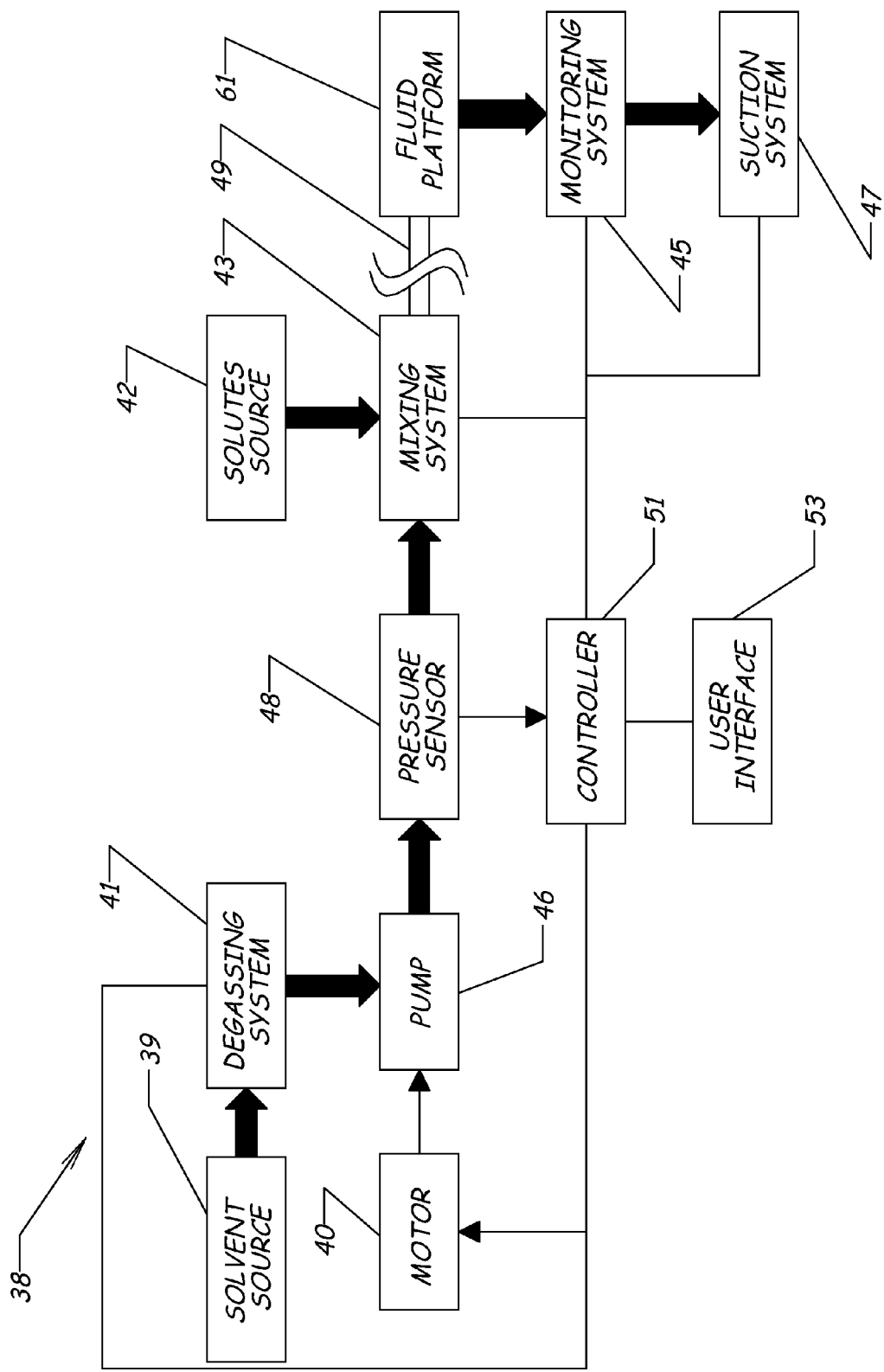

In some treatment methods, one or more secondary fluids may be added to a primary degassed fluid (e.g., an antiseptic solution can be added to degassed distilled water) (see, e.g., FIG. 6B). In some such methods, the secondary solution(s) may be degassed before being added to the primary degassed fluid. In other applications, the primary degassed fluid can be sufficiently degassed such that inclusion of the secondary fluids (which may have normal dissolved gas content) does not increase the gas content of the combined fluids above what is desired for a particular dental treatment.

In various implementations, the treatment fluid may be provided as degassed liquid inside sealed bags or containers. The fluid may be degassed in a separate setup in the operatory before being added to a fluid reservoir. In an example of an "in-line" implementation, the fluid can be degassed as it flows through the system, for example, by passing the fluid through a degassing unit attached along a fluid line (e.g., the fluid inlet 71). Examples of degassing units that can be used in various embodiments include: a Liqui-Cel® MiniModule® Membrane Contactor (e.g., models 1.7×5.5 or 1.7×8.75) available from Membrana-Charlotte (Charlotte, N.C.); a PermSelect® silicone membrane module (e.g., model PDMSXA-2500) available from MedArray, Inc. (Ann Arbor, Mich.); and a FiberFlo® hollow fiber cartridge filter (0.03 micron absolute) available from Mar Cor Purification (Skippack, Pa.). The degassing may be done using any of the following degassing techniques or combinations of thereof: heating, helium sparging, vacuum degassing, filtering, freeze-pump-thawing, and sonication.

In some embodiments, degassing the fluid can include de-bubbling the fluid to remove any small gas bubbles that form or may be present in the fluid. De-bubbling can be provided by filtering the fluid. In some embodiments, the fluid may not be degassed (e.g., removing gas dissolved at the molecular level), but may be passed through a de-bubbler to remove the small gas bubbles from the fluid.

In some embodiments, the degassing system 41 can include a dissolved gas sensor to determine whether the treatment fluid is sufficiently degassed for a particular endodontic treatment. A dissolved gas sensor can be disposed downstream of the mixing system 43 and used to determine whether mixing of solutes has increased the dissolved gas content of the treatment fluid after addition of solutes, if any. The solute source 42 may include a dissolved gas sensor For example, a dissolved gas sensor may measure the amount of dissolved oxygen in the fluid as a proxy for the total amount of dissolved gas in the fluid, since dissolved oxygen may be measured more readily than dissolved gas (e.g., nitrogen or helium). Dissolved gas content can be inferred from dissolved oxygen content based at least partly on the ratio of oxygen to total gas in air (e.g., oxygen is about 21% of air by volume). Dissolved gas sensors can include electrochemical sensors, optical sensors, or sensors that perform a dissolved gas analysis. Examples of dissolved gas sensors that can be used with embodiments of various systems disclosed herein include a Pro-Oceanus GTD-Pro or HGTD dissolved gas sensor available from Pro-Oceanus Systems Inc. (Nova Scotia, Canada) and a D-Opto dissolved oxygen sensor available from Zebra-Tech Ltd. (Nelson, New Zealand). In some implementations, a sample of the treatment can be obtained and gases in the sample can be extracted using a vacuum unit. The extracted gases can be analyzed using a gas chromatograph to determine dissolved gas content of the fluid (and composition of the gases in some cases).

Accordingly, in the example systems shown in FIGS. 2-4C (and the example systems shown and described below), the fluid delivered to the tooth from a fluid inlet and/or the fluid used to generate the jet in a liquid jet device may comprise a degassed fluid that has a dissolved gas content less than normal fluid. The degassed fluid may be used, for example, to generate the high-velocity liquid beam for generating pressure waves, to substantially fill or irrigate a chamber in the tooth (e.g., the pulp cavity and/or canal spaces), to provide a propagation medium for acoustic waves, to inhibit formation of air (or gas) bubbles in the tooth chamber (e.g., in canal spaces or tubules), and/or to provide flow of the degassed fluid into small spaces in the tooth (e.g., small canals, tubules, etc.). In embodiments utilizing a liquid jet, use of a degassed fluid may inhibit bubbles from forming in the jet due to the pressure drop at a nozzle orifice where the liquid jet is formed.

Thus, examples of methods for endodontic treatment comprise flowing a degassed fluid onto a tooth or tooth surface or into a tooth chamber. The degassed fluid may comprise a tissue dissolving agent and/or a decalcifying agent. The degassed fluid may have a dissolved oxygen content less than about 9 mg/L, less than about 7 mg/L, less than about 5 mg/L, less than about 3 mg/L, less than about 1 mg/L, or some other value. A fluid for endodontic treatment may comprise a degassed fluid with a dissolved oxygen content less than about 9 mg/L, less than about 7 mg/L, less than about 5 mg/L, less than about 3 mg/L, less than about 1 mg/L, or some other value. The fluid may comprise a tissue dissolving agent and/or a decalcifying agent. For example, the degassed fluid may comprise an aqueous solution of less than about 6% by volume of a tissue dissolving agent and/or less than about 20% by volume of a decalcifying agent.

II. EXAMPLE EMBODIMENTS OF APPARATUS AND METHODS FOR DENTAL TREATMENTS

A. Examples of Pressure Wave Generators

1. Examples of Liquid Jet Apparatus (i) Example Systems for Generating a High-Velocity Jet FIG. 6A is a block diagram that schematically illustrates an embodiment of a system 38 adapted to generate a high-velocity jet 60 of fluid for use in dental procedures. The system 38 comprises a motor 40, a fluid source 44, a pump 46, a pressure sensor 48, a controller 51, a user interface 53, and a handpiece 50 that can be operated by a dental practitioner to direct the jet 60 toward desired locations in a patient's mouth. The pump 46 can pressurize fluid received from the fluid source 44. The pump 46 may comprise a piston pump in which the piston is actuatable by the motor 40. The high-pressure liquid from the pump 46 can be fed to the pressure sensor 48 and then to the handpiece 50, for example, by a length of high-pressure tubing 49. The pressure sensor 48 may be used to sense the pressure of the liquid and communicate pressure information to the controller 51. The controller 51 can use the pressure information to make adjustments to the motor 40 and/or the pump 46 to provide a target pressure for the fluid delivered to the handpiece 50. For example, in embodiments in which the pump 46 comprises a piston pump, the controller 51 may signal the motor 40 to drive the piston more rapidly or more slowly, depending on the pressure information from the pressure sensor 48. In some embodiments, the pressure of the liquid that can be delivered to the handpiece 50 can be adjusted within a range from about 500 psi to about 50,000 psi (1 psi is 1 pound per square inch and is about 6895 Pascal (Pa)). In certain embodiments, it has been found that a pressure range from about 2,000 psi to about 15,000 psi produces jets that are particularly effective for endodontic treatments. In some embodiments, the pressure is about 10,000 psi.

The fluid source 44 may comprise a fluid container (e.g., an intravenous bag) holding any of the treatments fluids described herein. The treatment fluid may be degassed, with a dissolved gas content less than normal (e.g., non-degassed) fluids. Examples of treatment fluids include sterile water, a medical-grade saline solution, an antiseptic or antibiotic solution (e.g., sodium hypochlorite), a solution with chemicals or medications, or any combination thereof. More than one fluid source may be used. In certain embodiments, it is advantageous for jet formation if the liquid provided by the fluid source 44 is substantially free of dissolved gases, which may reduce the effectiveness of the jet and the pressure wave generation. Therefore, in some embodiments, the fluid source 44 comprises degassed liquid such as, e.g., degassed distilled water. A bubble detector (not shown) may be disposed between the fluid source 44 and the pump 46 to detect bubbles in the liquid and/or to determine whether liquid flow from the fluid source 44 has been interrupted or the container has emptied. Also, as discussed above degassed fluids may be used. The bubble detector can be used to determine whether small air bubbles are present in the fluid that might negatively impact jet formation or acoustic wave propagation. Thus in some embodiments, a filter or de-bubbler (not shown) can be used to remove small air bubbles from the liquid. The liquid in the fluid source 44 may be at room temperature or may be heated and/or cooled to a different temperature. For example, in some embodiments, the liquid in the fluid source 44 can be chilled to reduce the temperature of the high velocity jet 60 generated by the system 38, which may reduce or control the temperature of the fluid inside a tooth 10. In some treatment methods, the liquid in the fluid source 44 can be heated, which may increase the rate of chemical reactions that may occur in the tooth 10 during treatment.

The handpiece 50 can be configured to receive the high pressure liquid and can be adapted at a distal end to generate a high-velocity beam or jet 60 of liquid for use in dental procedures. In some embodiments, the system 38 may produce a coherent, collimated jet of liquid. The handpiece 50 may be sized and shaped to be maneuverable in the mouth of a patient so that the jet 60 may be directed toward or away from various portions of the tooth 10. In some embodiments, the handpiece 50 comprises a housing or cap that can be coupled to the tooth 10.

The controller 51 may comprise a microprocessor, a special or general purpose computer, a floating point gate array, and/or a programmable logic device. The controller 51 may be used to control safety of the system 38, for example, by limiting system pressures to be below safety thresholds and/or by limiting the time that the jet 60 is permitted to flow from the handpiece 50. The system 38 may also include a user interface 53 that outputs relevant system data or accepts user input (e.g., a target pressure). In some embodiments, the user interface 53 comprises a touch screen graphics display. In some embodiments, the user interface 53 may include controls for a dental practitioner to operate the liquid jet apparatus. For example, the controls can include a foot switch to actuate or deactuate the jet.

The system 38 may include additional and/or different components and may be configured differently than shown in FIG. 6A. For example, the system 38 may include an aspiration pump that is coupled to the handpiece 50 (or an aspiration cannula) to permit aspiration of organic matter from the mouth or tooth 10. In other embodiments, the system 38 may comprise other pneumatic and/or hydraulic systems adapted to generate the high-velocity beam or jet 60.

(ii) Example Systems for Providing a Fluid Platform

FIG. 6B is a block diagram that schematically illustrates an embodiment of a system 38 for providing fluid to a fluid platform 61 that is in fluid communication with a tooth 10. Some of the components in this system 38 can be generally similar to those described with respect to the system 38 shown in FIG. 6A. The system 38 includes a solvent source 39 (which may be the same or different from the fluid source 44 shown in FIG. 6A). The solvent may comprise water. The solvent flows to a degassing system 41 where it can be degassed to a desired level. The system 38 can include a mixing system 43 configured to mix solute(s) from a solutes source 42 into the fluid. The solute(s) can include any solid, liquid, or gas substances that may be added to the solvent. For example, the solute(s) can include antiseptic or antibacterial fluids or compounds (e.g., NaOCl or EDTA), surfactants, medicaments, nanoparticles, etc. Liquid solute(s) may, but need not be, degassed. The solvent and solutes flow to the fluid platform 61 via the tubing 49. The fluid platform 61 can include any of the example fluid platforms or other components described herein. For example, the fluid platform 61 can include a pressure wave generator to generate acoustic waves in the tooth to provide tooth cleaning.

In the illustrated system 38, the tubing 49 can be fluidly attached to a fluid inflow to the fluid platform 61. In some embodiments the flow rate of the treatment fluid (e.g., solvent plus solute(s)) in the fluid inflow can be in the range of about 0.4-1.2 cc/s. In other embodiments, the flow rate range can be about 0.2 to 2 cc/s, 0.01 to 5 cc/s, or other values (e.g., up to about 10, 20, or 50 cc/s). In one embodiment, the influx of the fluid can be pulsating. In other embodiments, the influx of the fluid can be intermittent. In one embodiment, the influx of the fluid can be substantially uniform over time.

In the illustrated system 38, the fluid platform 61 can include a fluid outlet that can remove fluid from the tooth. At least a portion of this fluid may be passed to a monitoring system 45, which can monitor the fluid flowing from the tooth to determine the extent or progress of the treatment. For example, the monitoring system 45 can include one or more monitoring sensors 74 that may be generally similar to the monitoring sensors described with reference to FIG. 3C. The monitoring system 45 may monitor the extent or progress of tooth cleaning and may signal the dental practitioner, via the user interface 53, when the cleaning is complete. In some implementations, the controller 51 (or the monitoring system 45) may use feedback (e.g., based on properties monitored by the monitoring system) to regulate, adjust, or control components of the system during the treatment. Such use of feedback advantageously may allow aspects of the endodontic treatment to be automated. For example, feedback can be used to activate or deactivate a pressure wave generator or fluid source to more efficiently provide treatment to the patient.

A fluid outlet can be connected to a suction system 47, which may be similar to suction or evacuation units found in dental offices. For example, some dental evacuation units are designed to operate at about −6 in-Hg to about −8 in-Hg and have an airflow rate of about 7 standard cubic feet per minute (SCFM) per chairside high-volume inlet. Independent vacuum systems can be used. In one embodiment, the operating pressure of the evacuation unit is about −4 to −10 in-Hg. In other embodiments, the operating pressure is in a range of about −0.1 to −5 in-Hg or −5 to −10 in-Hg or −10 to −20 in-Hg, or other values. In some embodiments, the flow provided by the evacuation unit can be pulsating. In another embodiment, the evacuation unit flow can be intermittent. In one embodiment, the evacuation unit flow can be substantially uniform. The air flow rate of the evacuation unit can be 5 to 9 SCFM or 2 to 13 SCFM or 0.1 to 7 SCFM or 7 to 15 SCFM or 15 to 30 SCFM or 30 to 50 SCFM, or other values.

In some implementations, it may be desired that the fluid entering the fluid platform 61 be degassed to a certain degree (e.g., about 40% of normal dissolved gas amount in one example). In some such implementations, the degassing system 41 may "over-degas" the solvent so that the solvent's dissolved gas content is below the desired degree (e.g., about 35% in this example) so that when solute(s) are added by the mixing system 43, the resulting fluid (solvent plus solute) is degassed to less than the desired degree (e.g., adding un-degassed antiseptic solution may raise the dissolved gas content to 38% in this example).

In the system 38 shown in FIG. 6B, the solute mixing system 43 is downstream from the degassing system 41. Some solutes may be able to chemically degrade wet components of the degassing system 41 (e.g., bleach can attack gaskets, filters, etc.). An advantage of the downstream arrangement shown in FIG. 6B is that such solutes can be added after the solvent has been degassed; therefore, these solutes will not pass through (and possibly degrade) the degassing system 41.

In some implementations, heat dissipated by the pressure wave generator 64 may accumulate and may cause a temperature increase in the fluid in the tooth chamber 65 (and/or in the tooth). A sufficient temperature increase may be damaging to the oral tissues. A significant temperature increase may occur during some procedures utilizing certain embodiments of uncontrolled fluid platforms. In some embodiment of the vented fluid platform, the mean fluid temperature and the mean tooth temperature may remain below temperatures safely tolerated by oral tissues. In some embodiments, the mean temperature remains between about 30 to 40° C. In other embodiments, the mean temperature remains between about 20 to 50° C., 10 to 60° C., 5 to 70° C., or else. The temperature may fluctuate and vary throughout the pulp cavity during the treatment and therefore the mean value of temperature may vary or fluctuate.

The temperature of the fluid inside the pulp cavity and the temperature of the tooth can depend at least in part on factors including the temperature of the treatment fluid supplied to the tooth, the heat dissipation rate of the pressure wave generator 64, the temperature of the fluid supply line (including the pump), and the flow rate of the treatment fluid. One or more of these factors (or others) may be adjusted during treatment to maintain a desired temperature of the fluid in the tooth, the tooth itself, the fluid flowing from the pulp chamber, etc. In various embodiments, one or more temperature sensors (e.g., thermistors) may be disposed in the handpiece, in or near the pressure wave generator 64, in the pulp cavity in the tooth, or in the fluid inflow and/or fluid outflow to the fluid platform, or elsewhere to monitor temperatures during the treatment. The systems shown in FIGS. 6A and 6B can include additional components (not shown) to regulate the temperature of the fluid anywhere along the fluid paths illustrated.

The system 38 may include additional and/or different components and may be configured differently than shown in FIG. 6B. For example, the mixing system 43 and the degassing system 41 can be combined. Either or both of these systems can be disposed anywhere in the fluid flow path upstream of the fluid platform 61. Also, other embodiments do not need to include all the components shown in FIGS. 6A and 6B. For example, some embodiments do not include a degassing system, a mixing system, and/or a monitoring system. FIGS. 6A and 6B are intended to be illustrative of the type of fluid arrangements that are possible and are not intended to be limiting.

Embodiments of the systems shown in FIGS. 6A and 6B may utilize components described in or be configured similarly to embodiments of the apparatus and systems described in U.S. Pat. No. 6,224,378, issued May 1, 2001, entitled "METHOD AND APPARATUS FOR DENTAL TREATMENT USING HIGH PRESSURE LIQUID JET," U.S. Pat. No. 6,497,572, issued Dec. 24, 2002, entitled "APPARATUS FOR DENTAL TREATMENT USING HIGH PRESSURE LIQUID JET," U.S. Patent Publication No. 2007/0248932, published Oct. 25, 2007, entitled "APPARATUS AND METHODS FOR TREATING ROOT CANALS OF TEETH," U.S. Patent Publication No. 2010/0143861, published Jun. 10, 2010, entitled "APPARATUS AND METHODS FOR MONITORING A TOOTH," U.S. Patent Publication No. 2011/0111365, published May 12, 2011, entitled "APPARATUS AND METHODS FOR ROOT CANAL TREATMENTS," and/or U.S. Patent Publication No. 2011/0117517, published May 19, 2011, entitled "LIQUID JET APPARATUS AND METHODS FOR DENTAL TREATMENTS"; the entire disclosure of each of the foregoing patents and publications is hereby incorporated by reference herein for all that it teaches or discloses.

(iii) Examples of a Coherent Collimated Jet

In certain embodiments, the system 38 may be configured to produce a liquid jet 60 that forms a substantially parallel beam (e.g., is "collimated") over distances ranging from about 0.01 cm to about 10 cm. In some embodiments, the velocity profile transverse to the propagation axis of the jet is substantially constant (e.g., is "coherent"). For example, in some implementations, away from narrow boundary layers near the outer surface of the jet 60 (if any), the jet velocity is substantially constant across the width of the jet. Therefore, in certain advantageous embodiments, the liquid jet 60 delivered by the dental handpiece 50 may comprise a coherent, collimated jet (a "CC jet"). In some implementations, the CC jet may have velocities in a range from about 100 m/s to about 300 m/s, for example, about 190 m/s in some embodiments. In some implementations, the CC jet can have a diameter in a range from about 5 microns to about 1000 microns, in a range from about 10 microns to about 100 microns, in a range from about 100 microns to about 500 microns, or in a range from about 500 microns to about 1000 microns. Further details with respect to CC jets that can be produced by embodiments of the system and apparatus described herein can be found in U.S. Patent Publication No. 2007/0248932 and/or U.S. Patent Publication No. 2011/0117517, each of which is hereby incorporated by reference herein in its entirety for all that it discloses or teaches.

(iv) Examples of Handpieces

Figure 7:
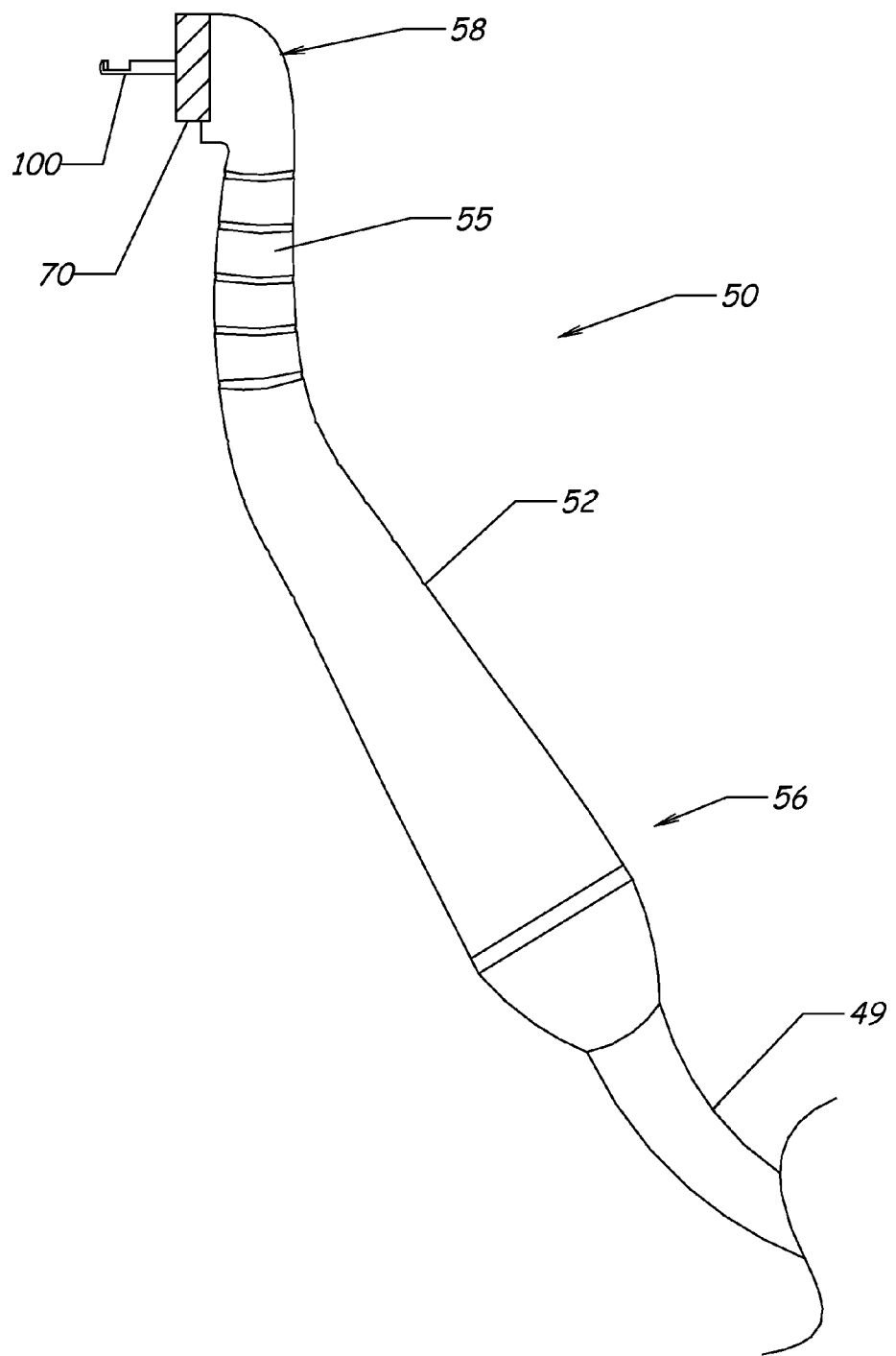
FIG. 7 is a side view schematically illustrating an embodiment of a handpiece comprising an embodiment of a guide tube for delivery of the liquid jet to a portion of a tooth.

FIG. 7 is a side view schematically illustrating an embodiment of a handpiece 50 comprising an embodiment of a positioning member configured to deliver the liquid jet 60 to a portion of the tooth 10. In various embodiments, the positioning member comprises a guide tube 100. The handpiece 50 comprises an elongated tubular barrel 52 having a proximal end 56 that is adapted to engage tubing 49 from the system 38 and a distal end 58 adapted to be coupled or attached to the tooth 10. The barrel 52 may include features or textures 55 that enhance grasping the handpiece 50 with the fingers and thumb of the operator. The handpiece 50 can be configured to be handheld. In some cases, the handpiece 50 can be configured to be portable, movable, orientable, or maneuverable with respect to the patient. In some implementations, the handpiece 50 can be configured to be coupled to a positioning device (e.g., a maneuverable or adjustable arm).

The distal end 58 of the handpiece 50 can comprise a housing or cap 70 that can be coupled to the tooth 10 (see, e.g., FIG. 4D). The cap 70 may be a detachable member that can be sized/shaped to fit on the patient's tooth and/or to position the distal end of the guide tube 100 at a desired location in the pulp cavity 26. A kit of caps may be provided such that a dental practitioner can select an appropriately-sized cap and attach it to the handpiece 50 (see, e.g., description of tooth sizing below).

The handpiece 50 may include a fluid inlet 71 for delivering treatment fluid to the tooth chamber 65, a fluid outlet 72 for removing fluid from the tooth (e.g., waste fluid), a pressure wave generator 64, a power line (e.g., to provide energy to a pressure wave generator), or a combination of some or all of the foregoing. The handpiece 50 may include other components such as, e.g., an irrigation line to irrigate the tooth area, a light source to illuminate the tooth area, etc. In some cases, the pressure wave generator 64 (e.g., a liquid jet) comprises the fluid inlet 71 (e.g., the jet). The handpiece 50 can be used to apply the pressure wave generator 64 relative to the tooth 10. The handpiece 50 can be applied to the tooth 10 so as to create a substantially closed fluid circuit as the distal end 58 of the handpiece 50 engages the tooth 10, thereby enabling fluid to be delivered into and out of the tooth chamber 65 without substantial spillage or leakage into the patient's mouth. As described herein, the handpiece 50 may include a fluid retention member (e.g., sponge or vent) to reduce the likelihood of fluid leakage and/or to allow fluid to flow from the tooth chamber 65 (e.g., to inhibit overpressurization or under-pressurization). The fluid retention member can be configured to inhibit air from entering the tooth chamber 65 (which may reduce the effectiveness of cavitation) while permitting air to enter a fluid outlet 72 (e.g., suction line).

The handpiece 50 can be shaped or sized differently than shown in FIG. 7. For example, the elongated tubular barrel 52 may not be used, and a dental practitioner may maneuver the cap 70 into a desired location in the patient's mouth. The patient may bite down on the cap 70 to hold the cap 70 in place during a treatment (see, e.g., FIG. 11). In other embodiments, the handpiece 50 can include a device that is clamped or attached to the tooth 10 (e.g., via a rubber dam clamp commonly used in endodontic procedures) such that the device doesn't require substantial user intervention during the procedure (see, e.g., FIGS. 10A and 10B).

The handpiece 50 can be disposable (e.g., single-use) or reusable. In one embodiment, the handpiece 50 is disposable, but the pressure wave generator 64 is reusable. In another embodiment, the handpiece 50 is reusable, and certain components of the pressure wave generator 64 (e.g., a guide tube) are disposable. In some embodiments, the distal end 58 of the handpiece 50 can include additional components such as, for example, a sealer or gasket (which may be an elastomeric material or a closed-cell foam), spacers (e.g., to position the distal end of the guide tube 100 at a desired location in the tooth chamber), vents, etc.

(v) Examples of Guide Tubes

Figure 8:
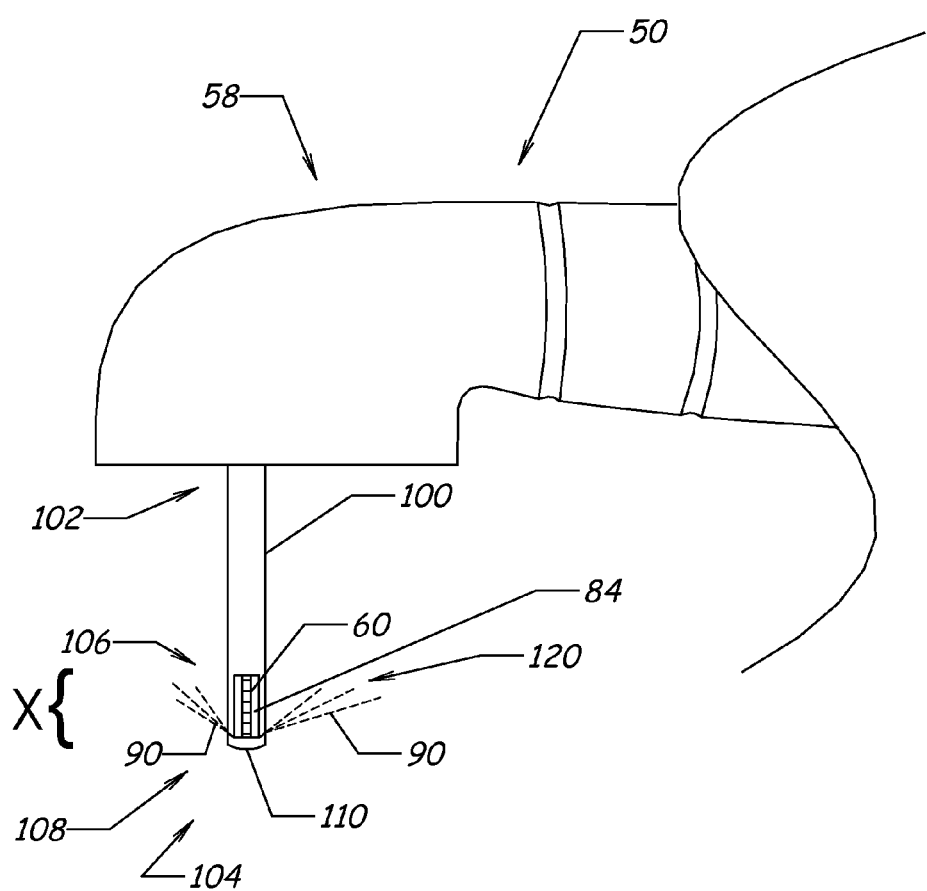
FIG. 8 is a side view schematically illustrating an embodiment of a distal end of a handpiece comprising an embodiment of a guide tube for delivering a liquid jet.

FIG. 8 schematically illustrates a distal end 58 of an example handpiece 50 comprising a guide tube 100. In this example, the fluid retainer (e.g., cap and/or flow restrictor) is disposed inside the distal end 58 of the handpiece 50. Embodiments of the guide tube 100 can be sized or shaped such that a distal end 104 of the guide tube 100 can be positioned through an endodontic access opening formed in the tooth 10, for example, on an occlusal surface, a buccal surface, or a lingual surface. For example, the distal end 104 of the guide tube 100 may be sized or shaped so that the distal end 104 can be positioned in the pulp cavity 26 of the tooth 10, e.g., near the pulpal floor, near openings to the canal space 30, or inside the canal openings. The size of the distal end 104 of the guide tube 100 can be selected so that the distal end 104 fits through the access opening of the tooth 10. In some embodiments, the width of the guide tube 100 can be approximately the width of a Gates-Glidden drill, for example, a size 4 Gates-Glidden drill. In some embodiments, the guide tube 100 can be sized similarly to gauge 18, 19, 20, or 21 hypodermic tubes. The width of the guide tube 100 may be in a range from about 0.1 mm to about 5 mm, in a range from about 0.5 mm to about 2.0 mm, or some other range. The length of the guide tube 100 can be selected so that the distal end 104 of the guide tube 100 can be disposed at a desired location in the mouth. For example, the length of the guide tube 100 between a proximal end 102 and the distal end 104 may be in a range from about 1 mm to about 50 mm, from about 10 mm to about 25 mm, or in some other range. In some embodiments, the length can be about 13 mm or about 18 mm, which may allow the distal end 104 of the guide tube 100 to reach the vicinity of the pulpal floor in a wide range of teeth. For teeth that may not have a pulpal chamber or a pulpal floor (e.g., anterior teeth), the distal end 104 of the guide tube 100 can be inserted into the canal space of the tooth 10. The guide tube 100 may be attached to the handpiece 50, or, in some cases, be a detachable or removable member. The guide tube 100 may be single-use or disposable. In some implementations, a kit of guide tubes is provided, and a dental practitioner can select a guide tube having a desired length (see, e.g., description of tooth sizing below).

Certain embodiments of the guide tube 100 can comprise an impingement member 110 (which also may be referred to herein as a deflector). The jet 60 can propagate along the channel 84 and impinge upon a surface of the impingement member 110, whereby at least a portion of the jet 60 can be slowed, disrupted or deflected, which can produce a spray 90 of liquid. The spray 90 may comprise droplets, beads, mist, jets, or beams of liquid in various implementations. Embodiments of the guide tube 100 which include an impingement member 110 may reduce or prevent possible damage that may be caused by the jet 60 during certain dental treatments. For example, use of the impingement member 110 may reduce the likelihood that the jet 60 may undesirably cut tissue or propagate into the root canal spaces 30 (which may undesirably pressurize the canal spaces in some cases). The design of the impingement member 110 may also enable a degree of control over the fluid circulation or dynamic pressures that can occur in the pulp cavity 26 during treatment.

The impingement member 110 may be disposed in a chamber 63, 65 or cavity in the tooth 10. In some methods, the impingement member 110 is disposed in fluid in the tooth 10, and the liquid jet 60 impacts an impingement surface of the impingement member 110 while the impingement member 110 is disposed in the cavity. The liquid jet 60 may be generated in air or fluid, and in some cases, a portion of the liquid jet 60 passes through at least some (and possibly a substantial portion) of fluid in the cavity in the tooth 10 before impacting the impingement member 110. In some cases, the fluid in the tooth cavity 65 may be relatively static; in other cases, the fluid in the tooth cavity 65 may circulate, be turbulent, or have fluid velocities that are less than (or substantially less than) the speed of the high-velocity liquid jet.

In some implementations, the impingement member 110 is not used, and the jet 60 can exit the guide tube 100 without substantial interference from portions of the guide tube 100. In some such implementations, after exiting the guide tube 100, the jet 60 may be directed toward a dentinal surface, where the jet 60 may impact or impinge upon the dentinal surface to provide acoustic energy to the tooth 10, to superficially clean the tooth 10, and so forth.

The guide tube 100 can include an opening 120 that permits the spray 90 to leave the distal end 104 of the guide tube 100. In some embodiments, multiple openings 120 can be used, for example, two, three, four, five, six, or more openings. The opening 120 can have a proximal end 106 and a distal end 108. The distal end 108 of the opening 120 can be disposed near the distal end 104 of the guide tube 100. The opening 120 can expose the liquid jet 60 (and/or the spray 90) to the surrounding environment, which may include air, liquid, organic material, etc. For example, in some treatment methods, when the distal end 104 of the guide tube 100 is inserted into the pulp cavity 26, the opening 120 permits the material or fluid inside the pulp cavity 26 to interact with the jet 60 or spray 90. A hydroacoustic field (e.g., pressure waves, acoustic energy, etc.) may be established in the tooth 10 (e.g., in the pulp cavity 26, the canal spaces 30, etc.) by the impingement of the jet 60 on the impingement member 110, interaction of the fluid or material in the tooth 10 with the jet 60 or they spray 90, fluid circulation or agitation generated in the pulp cavity 26, or by a combination of these factors (or other factors). The hydroacoustic field may include acoustic power over a relatively broad range of acoustic frequencies (e.g., from about a few kHz to several hundred kHz or higher; see, e.g., FIG. 2B-1). The hydroacoustic field in the tooth may influence, cause, or increase the strength of effects including, e.g., acoustic cavitation (e.g., cavitation bubble formation and collapse, microjet formation), fluid agitation, fluid circulation, sonoporation, sonochemistry, and so forth. It is believed, although not required, that the hydroacoustic field, some or all of the foregoing effects, or a combination thereof may act to disrupt or detach organic or inorganic material in the tooth, which may effectively clean the pulp cavity 26 and/or the canal spaces 30.

The length of the opening 120 between the proximal end 106 and the distal end 108 is referred to as X (see, e.g., FIG. 8). In various embodiments, the length X may be in a range from about 0.1 mm to approximately the overall length of the guide tube 100. In some embodiments, the length X is in a range from about 1 mm to about 10 mm. In some cases, the length X is selected so that the opening 120 remains submersed by fluid or material in the pulp cavity 26 of the tooth 10 during treatment. A length X of about 3 mm can be used for a wide variety of teeth. In some embodiments, the length X is a fraction of the overall length of the guide tube 100. The fraction can be about 0.1, about 0.25, about 0.5, about 0.75, about 0.9, or a different value. In some embodiments, the length X is a multiple of the width of the guide tube 100 or the channel 84. The multiple can be about 0.5, about 1.0, about 2.0, about 4.0, about 8.0, or a different value. The multiple can be in a range from about 0.5 to about 2.0, about 2.0 to about 4.0, about 4.0 to about 8.0, or more. In other embodiments, the length X is a multiple of the width of the jet, e.g., 5 times, 10 times, 50 times, or 100 times the width of the jet. The multiple can be in a range from about 5 to about 50, about 50 to about 200, about 200 to about 1000, or more. In some implementations, the length X of the opening 120 can be selected (at least in part) such that the hydroacoustic field generated in a tooth has desired properties including, e.g., desired acoustic power in the tooth at one or more acoustic frequencies. In some implementations, the length of X is selected so that both the proximal and distal ends 106, 108 of the opening 120 remain submerged in fluid during treatment.

Thus, the guide tube 100 can be used to deliver a pressure wave generator 64 to the tooth chamber 65. Embodiments of the guide tube 100 may, but need not, be used with non-jet pressure wave generators. For example, in an optical arrangement, an optical fiber can be disposed along the lumen or channel 84 of the guide tube 100. The fiber can have a tip configured to radiate light energy propagating in the fiber out into the fluid in the tooth chamber 65. The tip may be disposed so that the radiating light energy can exit the tip through a window 120 in the guide tube 100. In other embodiments, the tip of the fiber may extend beyond the distal end 104 of the guide tube 100 (e.g., the impingement member 110 (described below) and the window 120 need not be used). In an acoustic arrangement, an ultrasonic tip or an ultrasonic paddle can be disposed along the lumen or channel 84 of the guide tube 100. The guide tube 100 can protect the optical fiber or ultrasonic tip/transducer from damage when inserted into the tooth 10.

(vi) Examples of Flow Restrictors (e.g., Sponges, Vents, etc.)

As discussed herein, embodiments of flow restrictors may be used to help retain fluid in the tooth chamber 65, to inhibit backflow or splashing of fluid from the tooth, to permit fluid to leave the tooth chamber 65 to (e.g., to reduce the potential for over-pressurization of the chamber), to inhibit air from entering the tooth chamber 65 (which may reduce the effectiveness of pressure waves), and/or to permit air to be entrained with fluid removed from the tooth chamber 65 (e.g., to reduce the potential for under-pressurization of the chamber). In various embodiments, flow restrictors 68 can include sponges, vents, permeable or semi-permeable membranes, etc. that will be described with reference to FIGS. 12A and 12B.

(1) Examples of Sponges

In some cases the flow restrictor 68 can comprise a sponge. With reference to FIG. 12A, the sponge can be substantially cylindrical and can substantially surround the guide tube 100. The sponge can be used in addition to or as an alternative to a cap 70 that can be disposed toward the distal end 58 of the handpiece 50. In some embodiments, the sponge can be disposed within the cap 70 (see, e.g., FIGS. 3B, 3C, 9, 10A, and 11) to assist cushioning and positioning the cap 70 on the tooth 10 and to help prevent leakage between the cap 70 and the tooth 10 (or the tooth seal 75, if used). The sponge may be configured to contact a portion of the tooth 10 during the dental treatment. In some cases, the sponge is disposed loosely around the guide tube 100. The sponge may be removably attached to the guide tube 100 in some cases. The sponge can be configured to conform to the crown 12 of the tooth 10 under treatment. The sponge can be configured such that jet or spray that emerges from the opening 120 (or liquid from other sources such as, e.g., the flow tube) is sufficiently retained within the pulp cavity 26 so that the distal end 104 of the guide tube 100 may be contained or submersed in the fluid. The sponge may be attached to the distal end 58 of the handpiece 50 via an adhesive, clip, etc. The sponge may instead be attached directly to the tooth (or to the tooth seal 75, if used).

In certain treatment methods, the flow restrictor 68 may, but does not need to, substantially seal the opening to a cavity in the tooth 10 such that the cavity is substantially water tight. For example, in certain treatment methods, the flow restrictor 68 inhibits back flow (e.g., splashback) of fluid out of the cavity but need not prevent all fluid outflow from the tooth 10. For example, in some treatment methods, one or more openings may be formed in the tooth (e.g., via drilling) to allow some fluid to flow out of the cavity in the tooth 10, and the restrictor can be used to reduce or prevent fluid backflow out of other opening(s) (e.g., a coronal access opening).

As discussed, the flow restrictor 68 may include a sponge. The sponge may be formed from a material that is not adversely affected by chemicals or irrigation solutions such as, e.g., sodium hypochlorite, used during root canal procedures. The sponge may comprise any suitable porous and/or absorbent material (or materials). For example, the sponge may comprise a porous material (e.g., elastomeric, plastic, rubber, cellulose, fabric, foam, etc.) that can at least partially absorb liquid. The porous material may comprise an open-cell foam or a closed-cell foam. The foam can comprise polyvinyl foam, polyethylene foam, polyvinyl alcohol (PVA) foam, urethane foam, cellulose foam, silicone foam, etc. The flow restrictor 68 may comprise a permeable or semi-permeable membrane. The flow restrictor 68 material may be deformable and may be capable of deforming to contours of tooth surfaces. In some embodiments, the sponge comprises a material having a density in a range from about 1 to about 1000 kg/m$^3$, or in a range of about 10 to about 400 kg/m$^3$. In some embodiments, the sponge comprises a closed-cell vinyl foam having a density of about 160 kg/m$^3$ or about 176 kg/m$^3$. In other embodiments, a silicone foam can be used.

The sponge can have a tensile strength in a range from about 1 kPa to about 3000 kPa or in a range of about 50 kPa to about 400 kPa. The sponge can have an ultimate elongation in a range of about 5% to about 800% or in a range of about 50% to about 300%. In some embodiments, the sponge comprises cells and can have a visual cell count in a range of about 1 to about 250/cm or in a range from about 10 to about 40/cm. The foam may comprise an ester or another type of foam.

(2) Examples of Vents

In some cases the flow restrictor 68 can comprise one or more vents, e.g., openings, pores, channels, lumens, etc. that may permit some passage of air or liquid. FIG. 12A schematically depicts two example handpieces having different arrangements of vents 73 toward the distal end 58 of the handpiece 50. The vents 73 can have any size, shape, and/or configuration. For example, the vents 73 may be circular, oval, elliptical, rectangular, polygonal, etc. Any number of vents can be used including, zero, one, two, three, four, five, or more vents. The vents 73 may be disposed on the distal end 58 of the handpiece 50, on the cap 70, or elsewhere on the handpiece 50. In various embodiments, the vents may be disposed along (and be in fluid communication with) a fluid outlet and/or a fluid inlet.

Figure 12A:
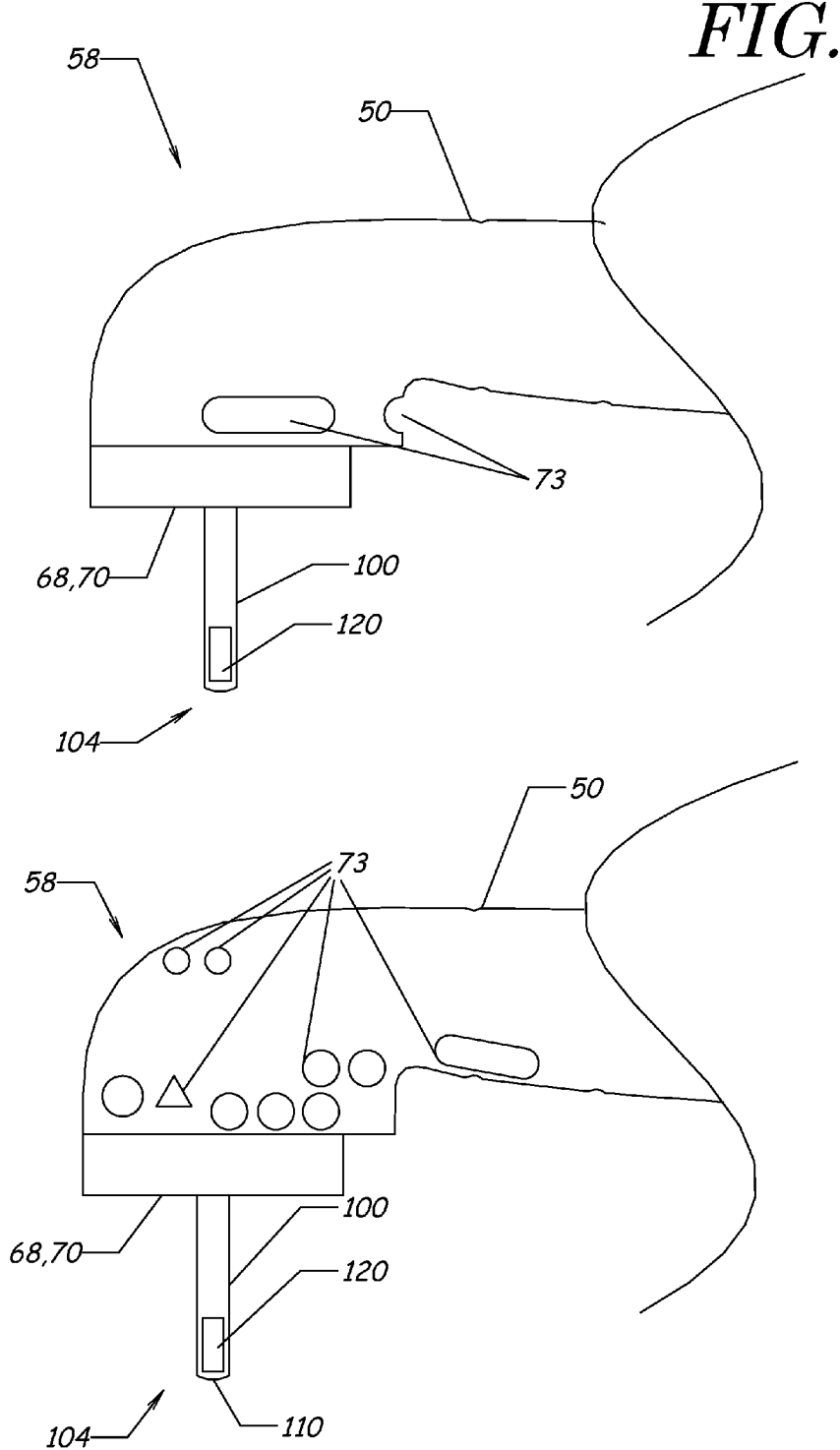
FIG. 12A schematically illustrates embodiments of a handpiece that includes flow restrictors, which can include, for example, sponges and/or vents.
Figure 12B:
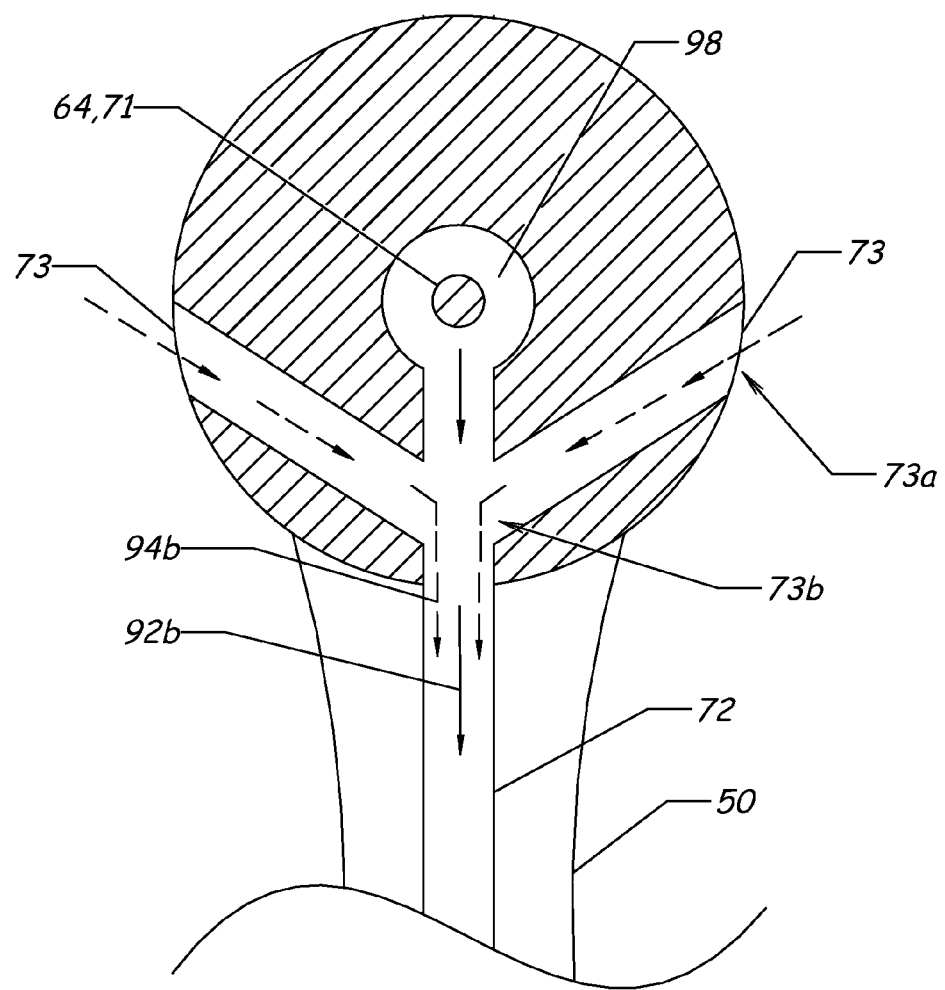
FIG. 12B is a top view that schematically illustrates an example arrangement of vents in a handpiece.

FIG. 12B is a top cross-section view of an embodiment of a handpiece 50 that schematically illustrates an example configuration of vents 73, which inhibits or prevents air from entering the pulp chamber 28 of the tooth 10. At the center is a pressure wave generator 64 (or a fluid inflow line). The fluid outflow surrounds the pressure wave generator (or fluid inflow line). Two vents 73 are shown that are angled away from the pressure wave generator 64 (or fluid inflow line) and angled toward the direction of fluid flow in the fluid outlet 72 (see, e.g., arrow 94a). In this example, the vents 73 comprise channels or lumens with a first end 73a on the outer surface of the handpiece 50, and a second end 73b joining the fluid outlet 72. Ambient air can flow from the first end 73a to the second end 73b and join or be entrained in flow in the fluid outlet 72. Also, as described herein, if fluid pressure in the tooth chamber becomes too large, fluid in the tooth chamber can flow out the vents 73 (e.g., the fluid can enter the second end 73b of the vent and leave the handpiece at the first end 73a of the vent). For example, the fluid outlet 72 may have an outlet axis generally along the fluid outflow direction (e.g., the arrow 94a), and a vent may have a vent axis generally along the airflow direction (e.g., the arrow 92b). In some embodiments, an angle between the vent axis and the outlet axis may be less than about 90 degrees, less than about 60 degrees, less than about 45 degrees, less than about 30 degrees, less than about 15 degrees, or some other angle. An advantage of some embodiments in which the angle is an acute angle is that the ambient airflow 92b can relatively smoothly join (or be entrained in) the fluid flow in the outlet 72. Further, some such embodiments may inhibit ambient air from flowing against the flow in the outlet 72 and entering the tooth chamber 65, where such ambient air may tend to inhibit cavitation effects in some treatments.

The vents 73 can extend from the outside of the handpiece 50 (where they can communicate with ambient air) to the fluid outlet line 72. In this example, the ambient air can flow towards an evacuation or suction unit that may also be used for removing waste fluid. During treatment, the outflow line therefore can include both fluid 92b (e.g., waste fluid from the tooth) and ambient air 94b from the vents 73. In this embodiment, by angling the vents 73 away from the center of the handpiece 50 where the pressure wave generator 64 (or inlet 71) is disposed, ambient air may be less likely to flow into the tooth chamber 65 (where the pressure is higher) and more likely to flow toward the outlet 72 (where the pressure is lower). In some embodiments, the vents can be positioned with respect to an evacuation line in such a way that air entrained into the handpiece 50 does not flow over the access opening of the tooth, where the waste fluid comes out.

The vents 73 can be designed to improve the safety of the fluid platform so that operating fluid pressures within the tooth chamber 65 remain at desired or safe levels. Use of the vents 73 can allow for a fluid platform which is open but in which the pressure and fluid flow is at least partially controlled. Although some closed fluid platforms may be relatively straightforward, in practice, they may require that the fluid inflow and outflow be highly controlled or precisely matched, or that the system be equipped with safety valves and/or shutoff switches. In some cases, such additions to the system not only can complicate the design of the system but may raise the number of possible failure points within the system.

System embodiments that are configured with vents 73 may allow the fluid platform to operate in a controlled and safe way. Additionally, the simplicity of the design of certain vents 73 can reduce the number of potential failure points. Further, some or all of the possible failure points may be reduced to failure points which cause little or no hazard to the patient or practitioner.

The use of vents 73 can provide for a self-regulating fluid platform, which depending on the state of the system, may allow air to be drawn into the fluid outflow path or may allow treatment fluid to overflow from the treatment area. The size and position of the vents 73 can be configured such that the system maintains a safe apical pressure during the following scenarios: while there is little or no flow or pressure through the inlet 71 or outlet 72, while there is an excess of flow or pressure through the inlet 71 or outlet 72, while there is a deficiency of flow or pressure through the inlet 71 or outlet 72, or combinations of the above scenarios.

In various embodiments, some or all of the following design considerations may be used in configuring vents 73 for a particular handpiece. The vents 73 can be placed along the fluid outlet path, away from the fluid inlet path, such that little or no air can be drawn into the tooth chamber 65. For example, the vents 73 can be designed such that air entering a fluid outflow line flows towards an evacuation unit; thereby inhibiting air from flowing toward the pulp chamber 28 of tooth, as air in the pulp chamber 28 may reduce the efficacy of treatment in some cases. The vents 73 can be placed relatively close to the distal end 58 of the handpiece 50. The vents 73 should not be placed too far away from the tooth such that during treatment, or in case of any failures, the treatment fluid does not build up too much static pressure (positive or negative) inside the tooth and cause adverse effects (e.g. due to elevation difference or flow resistance in the outflow line). In some embodiments, the fluid outlet 72 may have a distal end in the fluid retainer 66. The vents 73 may be placed about 0 to about 5 mm from the end of the fluid outlet 72, about 0 to about 25 mm from the end of the fluid outlet 72, or about 0 to about 100 mm from the end of the fluid outlet 72, or any other value. In some embodiments, rather than being measured from the end of the fluid outlet 72, the aforelisted distances may be measured with respect to an occlusal surface of the tooth or the endodontic access opening of the tooth.

In other embodiments, the vents 73 can be placed along the fluid inflow path (e.g., the fluid inlet side of the fluid retainer) and not along the fluid flow path. For example, in cases when fluid pressure in the tooth chamber rises toward or above a threshold (e.g., due to a blockage or clogging of the fluid outlet), a vent disposed along the fluid inflow path may open to shunt fluid out of the inflow path before such fluid would be delivered to the tooth chamber, which can at least partially alleviate the pressure rise. Some embodiments can utilize vents on both the fluid inflow and the fluid outflow paths (e.g., vents disposed along the fluid inlet and along the fluid outlet).

In some embodiments, the shape of the vents 73 can have a relatively large aspect ratio (e.g., the vent may have an elongated shape as opposed to a circle of the equivalent area). A vent 73 with a relatively large aspect ratio may enable the vent 73 to avoid spilling fluid during normal operation (e.g., due to liquid surface tension) while providing air flow along the suction line. The height of the vents may be between about 0 to 1 mm, about 0 to 3 mm, about 0 to 10 mm, or about 0 to 20 mm. The width of the vents may be between about 0 to 2 mm, about 0 to 6 mm, or about 0 to 20 mm. The aspect ratio (e.g., ratio of width to height) of the vent may be about 1:1, 1.25:1, 1.5:1, 2:1, 2.5:1, 3:1, or higher. The aspect ratio may be larger than about 1.5:1, larger than about 2:1, larger than about 2.5:1, or larger than about 3:1. Some vents may be circular or nearly circular (e.g., aspect ratio of about 1:1). In some embodiments, some vents that are closer to the distal end 58 of the handpiece 50 (e.g., closer to the tooth during treatment) are more elongated than some vents farther from the distal end 58 (e.g., farther from the tooth during treatment). In various embodiments, the area of each vent can be in a range from about 0.5 $mm^2$ to 4 $mm^2$, about 0.1 $mm^2$ to 3 $mm^2$, about 0.01 $mm^2$ to 10 $mm^2$, or larger (e.g., up to about 100 $mm^2$).

Multiple vents 73 may be used, for example, from 2 to 10, 2 to 50, or higher. It may be advantageous to have more than one vent spaced away from at least one other vent for the following some or all of the following reasons: to inhibit accidental blockage of a vent 73, to relieve pressure exerted via an additional suction system applied to a vent 73 (e.g., a hand-held dental suction tube operated by a dental practitioner or assistant), to maintain the size of each vent 73 small enough to reduce waste fluid from spilling out of a vent 73 during normal operation (e.g., using surface tension), and/or to provide the air flow along the fluid outlet 72. Multiple vents 73 can also be used to accommodate different positioning scenarios for the handpiece or fluid platform, e.g., left side of jaw, right side of jaw, upper teeth, or lower teeth). Multiple vents 73 can also help ensure that the fluid platform functions as desired when there are internal or external obstructions to fewer than all of the vents 73.

Accordingly, in various embodiments, the vents 73 may be properly sized, shaped, and arranged to allow for some or all of the following scenarios (or other scenarios). In some of these scenarios, the system can be configured so that little or no pressure is exerted on the pulp chamber.

(1) Waste treatment fluid suctioned through an outflow conduit; no external dental suction (e.g., no dental assistant providing external suction outside of the tooth): If the waste treatment fluid produced during the procedure is actively suctioned through the outflow conduit, the vents can allow air to enter the handpiece and further enter the outflow conduit. The vents can be properly balanced to maintain fluid in the tooth while not spilling fluid into the mouth. For example, if the cross-sectional area of the vents is too large, treatment solution introduced into the tooth may enter the vents and might spill into the mouth. If the cross-sectional area of the vents is too small, treatment solution may be suctioned out of the tooth, which may reduce cleaning effectiveness.

(2) Waste treatment fluid suctioned through the outflow conduit; external suction provided by the dental assistant: In this scenario, the dental assistant is actively using a dental suction wand to suction near the outside the handpiece. The vents may be sized and shaped such that an external suction source (e.g., the dental suction wand) has relatively little effect on treatment solution inside the handpiece.

(3) No active suction through the outflow conduit; no external dental suction: In this scenario, the operator may not have connected the outflow conduit to an evacuation unit or the fluid outlet may have become blocked or clogged. The waste treatment fluid can spill or flow through the vents into the patient's mouth (and may be suctioned out by a dental assistant). Fluid may be maintained in the tooth.

(4) No active suction through the outflow conduit; external suction provided by the dental assistant: In this scenario, an operator has not connected the outflow conduit to the evacuation unit, but a dental assistant is suctioning fluid spilled through the vents into the mouth. Fluid can still be maintained in the mouth.

In other implementations, the vents 73 may include one or more one-way or check valves configured with a cracking pressure(s) to allow fluid from the tooth chamber 65 to leave (e.g., if the fluid pressure in the tooth chamber 65 exceeds the cracking pressure) while preventing ambient air from entering the tooth chamber 65 (unless the pressure in the tooth chamber 65 becomes too low).

In various implementations, some or all of the foregoing design considerations may depend on several parameters including, e.g., the operating pressure and flow rate of the evacuation units used with the system, the treatment fluid flow rate, the diameter of the fluid outflow line, etc. The number, size, location, shape, and/or configuration of the vents 73 may vary in different embodiments. More than one possible design of vents 73 may function adequately for a certain set of operating parameters, and the design may be selected to achieve or optimize one or more of the foregoing design considerations (or other design objectives).

(vii) Additional Examples of Liquid Jet Devices

Figure 9:
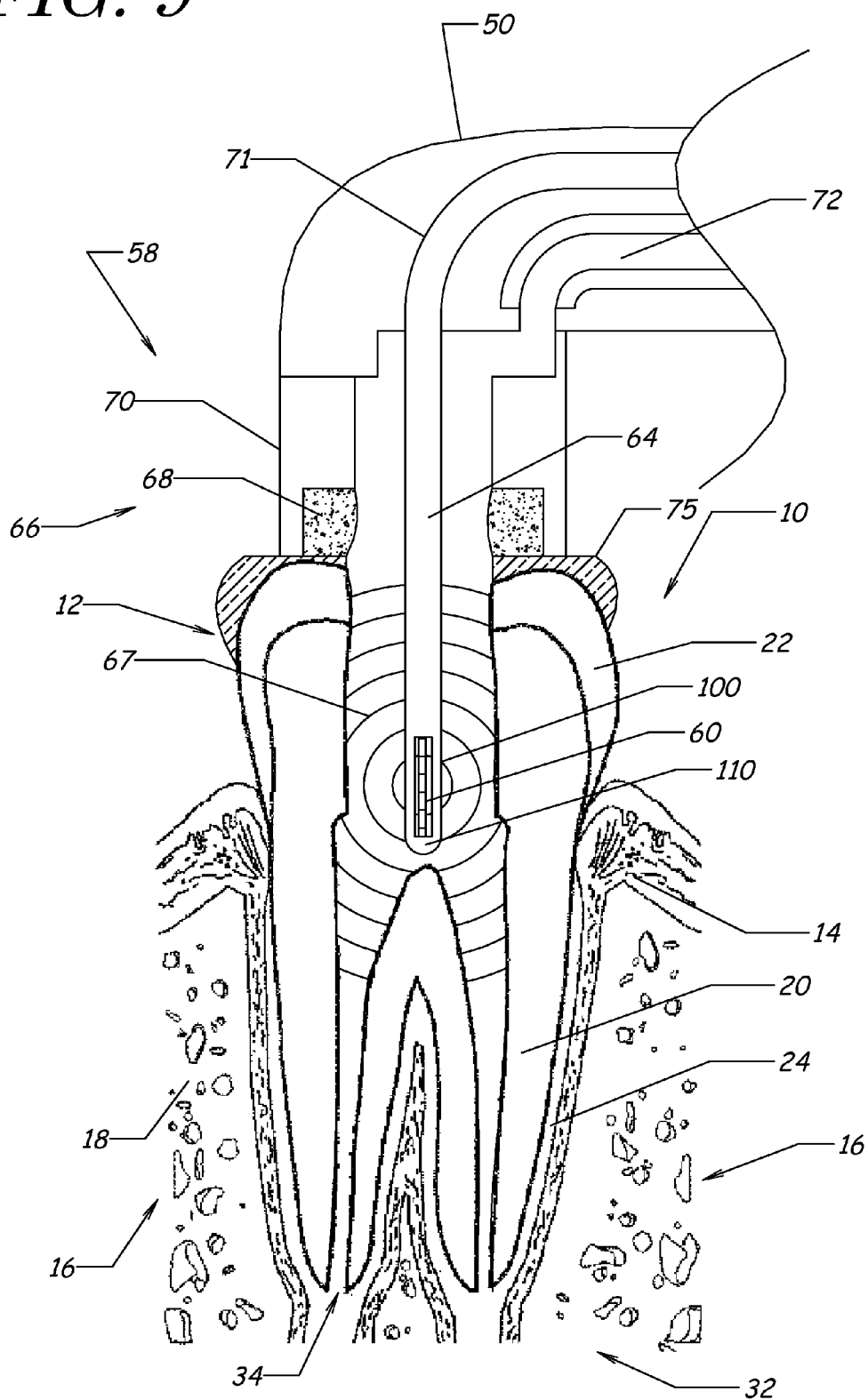
FIG. 9 schematically illustrates an example of a handpiece comprising a pressure wave generator comprising a liquid jet device. The handpiece comprises a fluid outlet, and the pressure wave generator provides a fluid inlet (the liquid jet).

FIG. 9 schematically illustrates an embodiment of a handpiece 50 that includes a fluid inlet 71 to deliver fluid to the guide tube 100, which can be disposed in the tooth chamber 65. As discussed, the fluid can emerge as a high-velocity jet beam 60, interact with ambient fluid in the tooth chamber, strike an impingement surface 110 at the distal end of the guide tube 100, and disperse as a spray 90 to generate pressure waves 67. The handpiece 50 also includes a fluid outlet 72 for removing fluid from the tooth 10. For example, the fluid outlet 72 can be fluidly coupled to a suction line or evacuation system commonly found in dental offices.

Figure 10A:
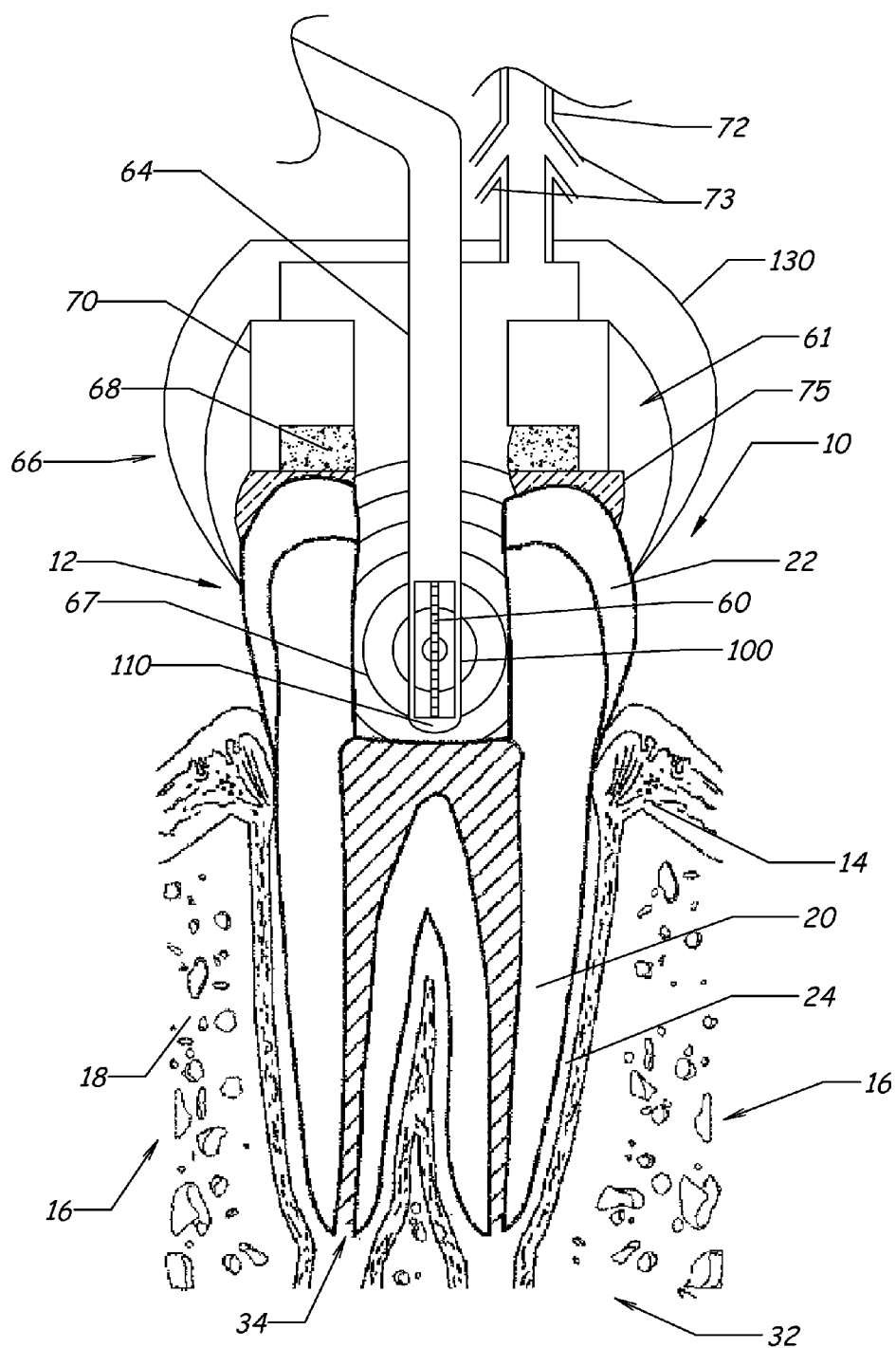
FIG. 10A is a cross-section view that schematically illustrates an example of a fluid platform that can be applied to a tooth using a clamp. The fluid platform comprises a pressure wave generator (e.g., liquid jet) and a vented fluid outlet.
Figure 10B:
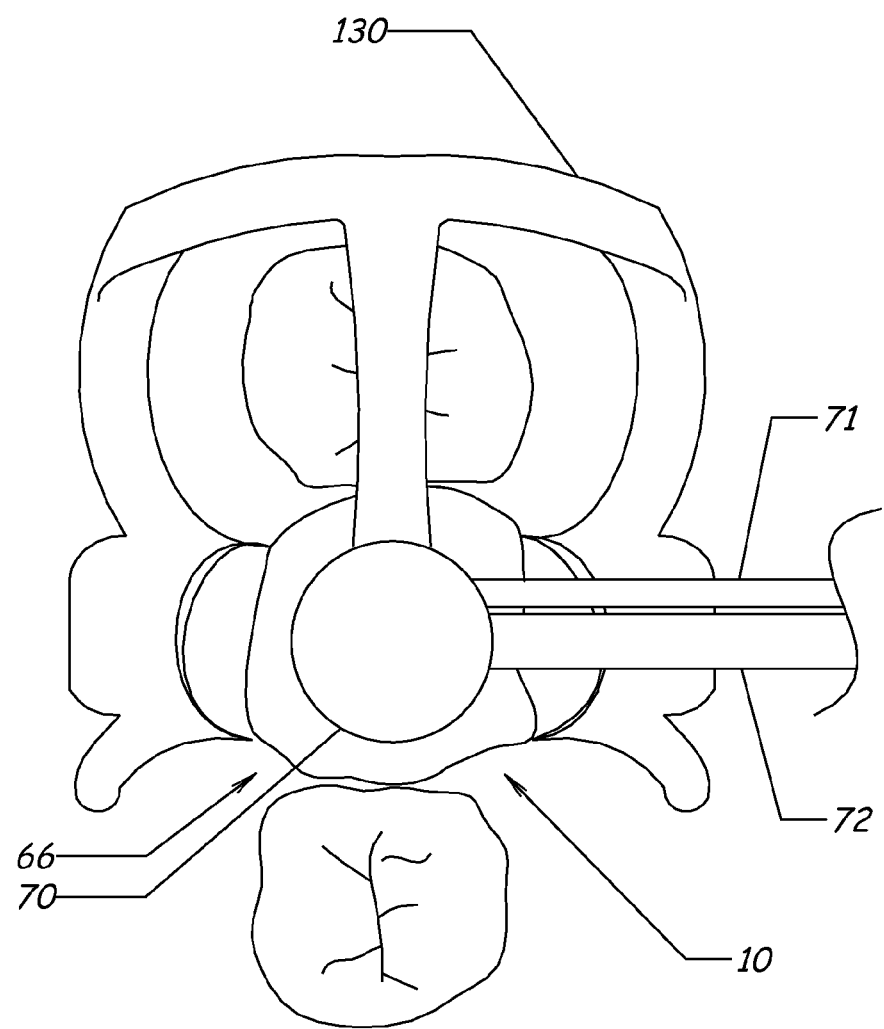
FIG. 10B is a top view that schematically illustrates an example of a fluid platform that can be attached to the tooth with a rubber dam clamp. A fluid inlet and fluid outlet are shown.

FIG. 10A is a cross-section view and FIG. 10B is a top view that schematically illustrate an example of a fluid platform 61 that can be applied to a tooth (e.g., on the flat surface of a tooth seal 75, if used). In this example, the fluid platform 61 includes a fluid retainer 66 including a pressure wave generator 64 (e.g., liquid jet) and a fluid outlet 72 comprising two vents 73. The fluid retainer 66 can be attached to the tooth with a rubber dam clamp 130. In this example, an elongated handpiece is not used, and the fluid retainer 66 can be maneuvered into position manually by the dental practitioner. The rubber dam clamp 130 can be clamped to the fluid retainer 66 and the tooth under treatment (and/or adjacent teeth) when the fluid platform 61 (or the pressure wave generator 64) is in the desired position for treatment.

Figure 11:
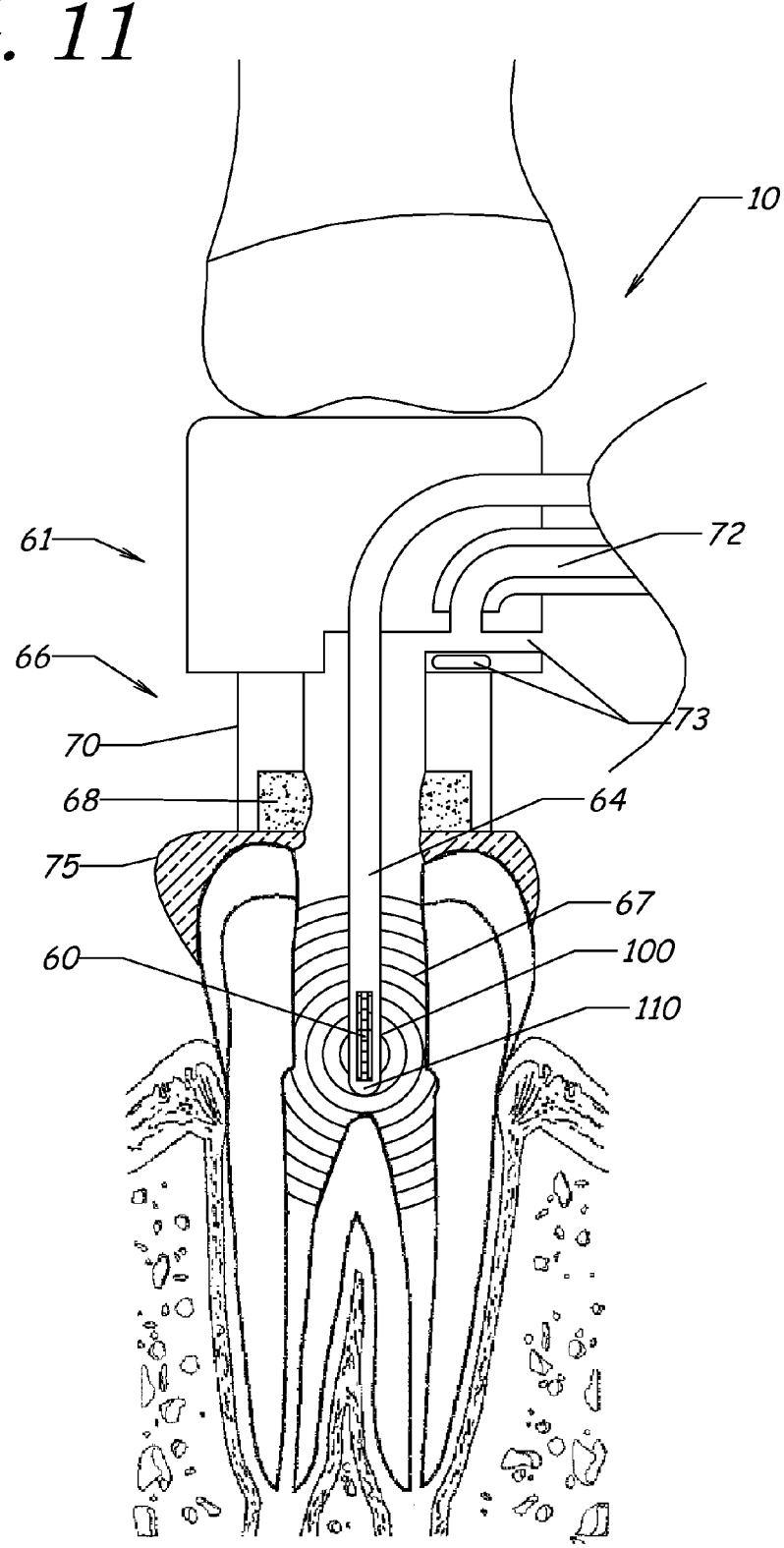
FIG. 11 schematically illustrates an alternative example of a fluid platform that can be applied to a tooth under treatment and held in place with pressure applied by the patient's opposing tooth.

FIG. 11 schematically illustrates an alternative example of a fluid platform 61 that can be applied to a tooth 10. In this example, the fluid retainer 66 is placed on the tooth seal 75 (if used) of the tooth under treatment and can be held in place by the patient biting down on the fluid platform 61 with the opposing tooth. In some embodiments, a rubber dam clamp 130 may additionally be used (see, e.g., FIGS. 10A and 10B). In this embodiment, the fluid retainer includes a pressure wave generator 64 (e.g., a liquid jet), and a fluid outlet 72 comprising vents 73.

2. Additional Examples of Pressure Wave Generators

As has been described, a pressure wave generator can be any physical device or phenomenon that converts one form of energy into pressure waves within the treatment fluid. Many different types of pressure wave generators (or combinations of pressure wave generators) are usable with embodiments of the systems and methods disclosed herein.

(i) Mechanical Energy

Pressure wave generators can include liquid jet devices. Mechanical energy pressure wave generators can also include rotating objects, e.g. miniature propellers, an eccentrically-confined rotating cylinder, a perforated rotating disk, etc. These types of pressure wave generators can also include vibrating, oscillating, or pulsating objects such as sonication devices that create pressure waves via piezoelectricity, magnetostriction, etc. In some pressure wave generators, electric energy transferred to a piezoelectric transducer can pressure waves in the treatment fluid. In some cases, the piezoelectric transducer can be used to create acoustic waves having ultrasonic frequencies.

(ii) Electromagnetic Energy

An electromagnetic beam of radiation (e.g., a laser beam) can propagate energy into the tooth chamber, and the electromagnetic beam energy can be transformed into pressure waves as it enters the treatment fluid. For example, at least some of the electromagnetic energy may be absorbed by the fluid (e.g., water) in the tooth chamber, which can generate localized heating and pressure waves that propagate in the fluid. The pressure waves generated by the electromagnetic beam can generate photo-induced or photo-acoustic cavitation effects in the fluid. The electromagnetic radiation from a radiation source (e.g., a laser) can be propagated to the tooth chamber by an optical waveguide (e.g., an optical fiber), and dispersed into the fluid at a distal end of the waveguide (e.g., a shaped tip of the fiber, e.g., a conically-shaped tip). In other implementations, the radiation can be directed to the tooth chamber by a beam scanning system.

The wavelength of the electromagnetic energy may be in a range that is strongly absorbed by water molecules. The wavelength may in a range from about 300 nm to about 3000 nm. In some embodiments, the wavelength is in a range from about 400 nm to about 700 nm, about 700 nm to about 1000 nm (e.g., 790 nm, 810 nm, 940 nm, or 980 nm), in a range from about 1 micron to about 3 microns (e.g., about 2.7 microns or 2.9 microns), or in a range from about 3 microns to about 30 microns (e.g., 9.4 microns or 10.6 microns). The electromagnetic energy can be in the ultraviolet, visible, near-infrared, mid-infrared, microwave, or longer wavelengths.

The electromagnetic energy can be pulsed or modulated (e.g., via a pulsed laser), for example with a repetition rate in a range from about 1 Hz to about 10 kHz. The pulse energy can be in a range from about 1 mJ to about 1000 mJ. The pulse width can be in a range from about 10 µs to about 500 µs, about 1 ms to about 500 ms, or some other range. In some cases, nanosecond pulsed lasers can be used with pulse rates in a range from about 100 ns to about 500 ns. The foregoing are non-limiting examples of radiation parameters, and other repetition rates, pulse widths, pulse energies, etc. can be used in other embodiments.

The laser can include one or more of a diode laser, a solid state laser, a fiber laser, an Er:YAG laser, an Er:YSGG laser, an Er, Cr:YAG laser, an Er, Cr:YSGG laser, a Ho:YAG laser, a Nd:YAG laser, a CTE:YAG laser, a $CO_2$ laser, or a Ti:Sapphire laser. In other embodiments, the source of electromagnetic radiation can include one or more light emitting diodes (LEDs). The electromagnetic radiation can be used to excite nanoparticles (e.g., light-absorbing gold nanorods or nanoshells) inside the treatment fluid, which may increase the efficiency of photo-induced cavitation in the fluid. The treatment fluid can include excitable functional groups (e.g., hydroxyl functional groups) that may be susceptible to excitation by the electromagnetic radiation and which may increase the efficiency of pressure wave generation (e.g., due to increased absorption of radiation). During some treatments, radiation having a first wavelength can be used (e.g., a wavelength strongly absorbed by water) followed by radiation having a second wavelength not equal to the first wavelength (e.g., a wavelength less strongly absorbed by water). For example, in some such treatments, the first wavelength may help create bubbles in the tooth fluid, and the second wavelength may help disrupt the tissue.

The electromagnetic energy can be applied to the tooth chamber for a treatment time that may be in a range from about one to a few seconds up to about one minute or longer. A treatment procedure may include one to ten (or more) cycles of applying electromagnetic energy to the tooth. A fluid platform may be used to circulate a fluid in the tooth chamber during the treatment process, which advantageously may inhibit heating of the tooth (which may cause discomfort to the patient). The fluid platform may include a fluid retainer to assist retaining fluid in the tooth. The fluid retainer may inhibit splashback of fluid, which can occur by hydraulic self-ejection during certain pulsed laser treatments. The circulation of treatment fluid (e.g., water with a tissue dissolving agent) by the fluid platform may bring fresh treatment fluid to tissue and organic matter as well as flush out dissolved material from the tooth. In some treatments using electromagnetic radiation, circulation of the treatment fluid can increase the effectiveness of the cleaning (as compared to a treatment with little or no fluid circulation).

In some implementations, electromagnetic energy can be added to other pressure wave generation modalities. For example, electromagnetic energy can be delivered to a tooth chamber in which a mechanical energy pressure wave generator (e.g., a liquid jet) is used to generate the acoustic waves.

(iii) Acoustic Energy

Acoustic energy (e.g., ultrasound) can be generated from electric energy transferred to an ultrasound transducer or an ultrasonic tip (or file or needle) that creates pressure waves in the treatment fluid. The ultrasonic transducer may comprise a piezoelectric crystal that physically oscillates in response to an electrical signal or a magnetostrictive element that converts electromagnetic energy into mechanical energy. The transducer can be disposed in the treatment fluid, for example, in the fluid inside the pulp cavity or in the fluid contained within the fluid platform (but outside the pulp cavity). An example of the power spectrum that can be produced by an ultrasonic device is shown in FIG. 2B-2. Ultrasonic sources can provide acoustic power in a frequency range from about 20 kHz to about 40 kHz (e.g., about 30 kHz) in various embodiments. Sonic (e.g., frequencies less than about 20 kHz such as about 1 kHz to 8 kHz) or megasonic energy (e.g., frequencies greater than about 1 MHz) can be used in some embodiments.

(iv) Further Properties of Some Pressure Wave Generators

A pressure wave generator 64 can be placed at a desired location with respect to the tooth. The pressure wave generator 64 creates pressure waves 67 within the fluid inside the tooth (the generation of pressure waves 67 may or may not create or cause cavitation). The pressure waves 67 propagate throughout the fluid inside the tooth, with the fluid in the tooth serving as a propagation medium for the pressure waves 67. The pressure waves 67 can also propagate through tooth material (e.g., dentin). It is believed, although not required, that as a result of application of a sufficiently high-intensity pressure wave, acoustic cavitation may occur. The collapse of cavitation bubbles may induce, cause, or be involved in a number of processes described herein such as, e.g., sonochemistry, tissue dissociation, tissue delamination, sonoporation, and/or removal of calcified structures. A smear layer in a canal space includes a layer of dentin, organic and inorganic debris, and bacteria created during instrumentation of canals (e.g., by endodontic files). The cavitation effects discussed herein can be effective at removing the smear layer. In some embodiments, the pressure wave generator 64 may be configured such that the pressure waves 67 (and/or cavitation) do not substantially break down natural dentin in the tooth. The pressure wave field by itself or in addition to cavitation may be involved in one or more of the abovementioned processes.

In some implementations, the pressure wave generator generates primary cavitation, which creates pressures waves, which may in turn lead to secondary cavitation. The secondary cavitation may be weaker than the primary cavitation and may be non-inertial cavitation. In other implementations, the pressure wave generator generates pressure waves directly, which may lead to secondary cavitation.

In various implementations, the pressure wave generator 64 can be disposed in suitable locations. For example, the pressure wave generator 64 can be attached to a handpiece 50 that can be maneuvered in a patient's mouth. The distal end of the pressure wave generator 64 can be disposed inside the pulp cavity 26, for example, in close proximity to the canals on the pulp chamber 28 floor. In such implementations, for a given amount of energy emitted by the pressure wave generator 64, the pressure waves 67 may have an increased effect on cleaning, decalcifying, and removing a smear layer within the canals and the pulpal chamber the closer the pressure wave generator 64 is to the canals. In some cases, the distal end of the pressure wave generator 64 is located at a distance of about 1 mm to about 3 mm from the pulp chamber floor. The desired distance may depend on the modality used to create the pressure waves 67 in the fluid (e.g., mechanical, electromagnetic, acoustic). In other embodiments, the distal end of the pressure wave generator 64 may be located inside a root canal 30. For example, the guide tube 100 can comprise a flexible material that can be directed down a canal toward the apex of the canal. In one embodiment, the distal end of the pressure wave generator 64 is positioned outside the pulp cavity 26 but exposed to fluid in the pulpal cavity. In another embodiment, the distal end of the pressure wave generator 64 is positioned inside the root canal space 30.

In some embodiments in which the pressure wave generator 64 (or fluid inlet 71) causes a stream of fluid to flow into the root canal, dynamic pressurization of the root canal may occur, which in turn may cause periapical extrusion of materials in some patients. The parameters influencing dynamic pressurization can include, e.g., the direction, shape, and speed of the stream of fluid with respect to the canal orifices and also the pulp cavity shape and topology. Also, in some implementations, if the pressure wave generator 64 enters the root canal orifice and substantially blocks the root canal pathway, the blockage may decelerate or even stop the set of physicochemical phenomena used to clean and disinfect the root canals. Thus, as discussed above, the pressure wave generator 64 can be designed such that the distal end of the pressure wave generator 64 is located at a desired or prescribed location in the pulp chamber 28 of the teeth.

The energy source that provides the energy for the pressure wave generator 64 can be located outside the handpiece, inside the handpiece, integrated with the handpiece, etc.

Figure 13A:
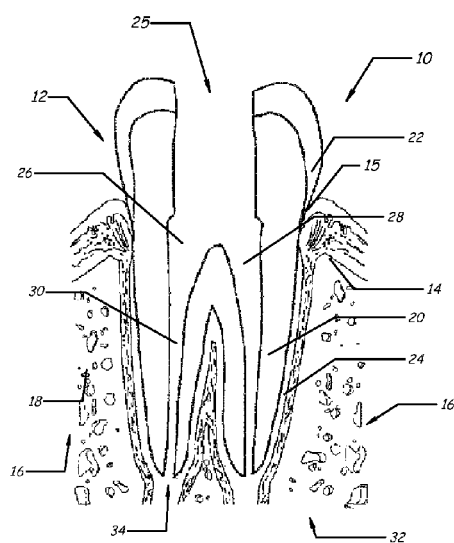
FIG. 13A schematically illustrates an access opening formed in a tooth.

B. Examples of Methods and Apparatus for Endodontic Treatment with Fluid Platforms FIG. 13A schematically illustrates an access opening 25 formed in a tooth 10. A drill or grinding tool can initially be used to make the opening 25 in the tooth 10. The opening 25 may extend through the enamel 22 and the dentin 20 to expose and provide access to pulp in the pulp cavity 26. The opening 25 may be made in a top portion of the crown 12 of the tooth 10 or in another portion such as a side of the crown 12, near the cemento-enamel junction 15, or in the root 16 below the gum 14. The opening 25 may be sized and shaped as needed to provide suitable access to the diseased pulp and/or some or all of the canal spaces 30. A fluid platform 61 or handpiece 50 can be applied or attached to the tooth so as to enable an endodontic procedure in the tooth.

(1) Examples of a Tooth Seal

Figure 13B:
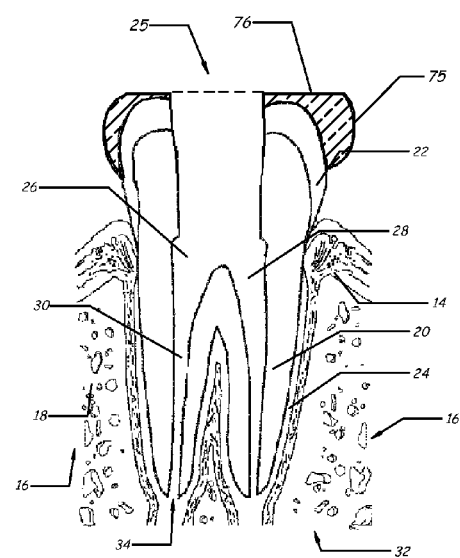
FIG. 13B schematically illustrates an embodiment of a tooth seal applied to a perimeter of a crown of the tooth of FIG. 13A. The upper surface of the tooth seal can be made substantially flat after application and removal of a flat plate.

In other methods, an (optional) tooth seal 75 can be formed on the tooth to provide a flat surface 76 to which a fluid platform 61 or handpiece 50 can be applied. FIG. 13B schematically illustrates an embodiment of the tooth seal 75 applied to a crown 12 of the tooth 10 of FIG. 13A. As will be described, the upper surface 76 of the tooth seal 75 can be made substantially flat after application and removal of a flat plate.

The tooth seal 75 can be used to temporarily fill grooves, dents, or imperfections of the occlusal surface of the tooth or to create a substantially flat surface 76 that a cap 70 of a fluid platform 61 or handpiece 50 can engage with. A tooth seal 75 can facilitate a water-tight and/or air-tight seal that substantially inhibits entry into and/or escape of liquid or air from the pulp chamber 28. The tooth seal 75 may be used to form a substantially hermetic seal of the pulp chamber 28. The tooth seal 75 can help the cap 70 engage with a tooth with substantial crown irregularities or irregularities due to other reasons, thereby sealing irregularities that the cap 70 would not be able to easily fill in by itself.

Figure 13C:
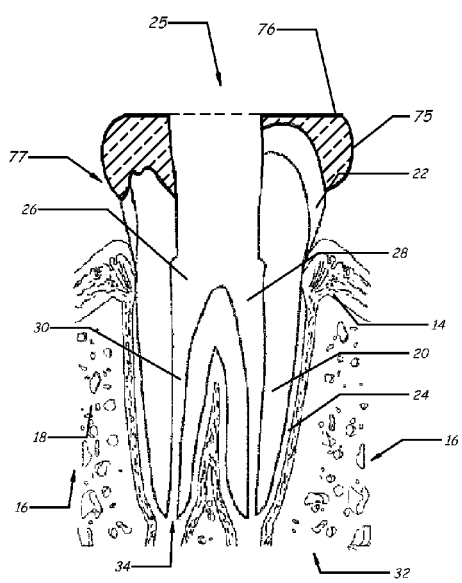
FIG. 13C schematically illustrates an embodiment of a tooth seal applied to a tooth in which a portion of the crown is missing due to decay. The tooth seal can be used to cover or build up the portion of the crown so that the tooth seal (and the non-decayed portion of the crown) form a substantially complete chamber for fluid treatments.

In some instances where a tooth 10 is missing a wall, or has decay, the tooth seal 75 (or one or more dental composite materials) may be used to rebuild the damaged or decayed portion of the tooth 10 before forming the tooth seal 75 on the crown 12. FIG. 13C schematically illustrates an embodiment of a tooth seal 75 applied to a tooth 10 in which a portion 77 of the crown 12 is missing due to decay or damage. The tooth seal 75 has been used to cover or build up the portion 77 of the crown 12 so that the tooth seal 75 (and the non-decayed portion of the tooth) form a substantially complete chamber for subsequent fluid treatments.

The tooth seal 75 can comprise a material that can easily be removed from the tooth after use. The material may be reshaped using tools such as dental bur, scalpel, etc. The material can be substantially pliable or semi-flexible that will set in a relatively short time (e.g., less than about 30 seconds) either by itself or with curing (e.g. via curing light). Examples of materials that can be used, alone or in combination, to form the tooth seal 75 include silicones, impression materials, 3M Imprint™ Bite, Jet Blue Bite by Colténe Whaledent®, etc.

An example method for applying the tooth seal 75 to a tooth is as follows. An endodontic access opening 25 in the tooth can be made, e.g., using standard endodontic access preparation techniques, substantially as used in conventional root canal procedures. In some embodiments, the canals can be prepared using standard techniques. In other embodiments, the canals are not prepared. Tooth seal material can be applied on the occlusal surface of the tooth and/or also around perimeter of the crown 12. Decayed or diseased portions of the tooth may be built up using the tooth seal material or other composite material. A flat plate can be applied to the tooth seal material, e.g., by pushing the plate onto the material, thereby creating a substantially flat surface beneath the plate. The operator can wait until the material sets or can use a curing light to cure the material (if photo-curable). The flat plate can be removed from the tooth seal material. If any of the material has penetrated the pulp chamber 28 or blocked the endodontic access opening 25, the material can be removed with a tool (e.g. dental bur). A fluid platform 61, handpiece 50, or cap 70 can be applied to the flat surface of the tooth material and the endodontic procedure can begin.

In some such methods, the tooth seal 75 may be applied to the tooth before the endodontic access opening 25 is formed. The endodontic access opening 25 can then be formed for both dentin and the tooth seal material. In this case, using a substantially transparent material may be preferred to improve visibility for endodontic access.

The tooth seal material may adhere to the tooth by itself or may be attached to the tooth using adhesive. In some methods, the tooth seal material may be applied in such a way so that it flows over and into a rubber dam clamp, which upon setting/curing enforces the attachment of the tooth seal material onto the tooth. In some such methods, the material at least partially adheres to the tooth while engaging with the rubber dam clamp.

An example method of applying a tooth seal 75 to a tooth comprises applying a tooth seal material to a surface of the tooth, and planarizing a surface 76 of the tooth seal material. In some embodiments, the method includes forming an access opening 25 in the tooth, wherein the access opening 25 can be formed prior to applying the tooth seal material or after applying the tooth seal material. In some embodiments, planarizing the surface of the tooth comprises apply a flat surface to the tooth seal material. The method may include curing the tooth seal material. The method may include removing the flat surface from the tooth seal material. The method may include building up a portion of a tooth using a composite material or the tooth seal material.

(2) Examples of a Tooth Sizer

In some methods, the distal end of a fluid inlet 71 and/or a pressure generator 64 can be positioned inside the pulp chamber 28 with the distal end at a desired distance from a root canal orifice. By positioning the distal end of the fluid inlet 71 at a suitable location in the pulp chamber 28, patient safety may be improved by, e.g., not over-pressurizing root canal spaces 30. By positioning the distal end of the pressure wave generator 64 at a suitable location in the pulp chamber 28, effectiveness of the acoustic waves 67 at generating cavitation and cleaning effects may be increased. Further, fluid circulation in portions of the tooth chamber (e.g., circulation in a root canal space) may be enhanced. In various methods, the vertical distance between the distal end of the fluid dispenser and/or the pressure wave generator 64 and the highest point of the pulpal floor may be in a range from about 0 to 1 mm, 0 to 5 mm, 5 to 10 mm, 10 to 15 mm, 15 to 30 mm, 0 to 30 mm, or some other range.

Figure 14A:
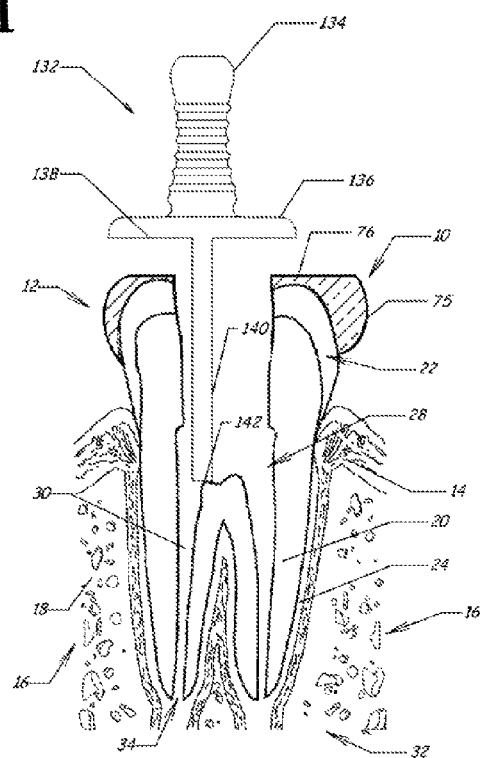
FIG. 14A schematically illustrates an example of a sizer inserted into a pulp chamber of an example tooth. In this example, the sizer is too large for the pulp chamber.
Figure 14B:
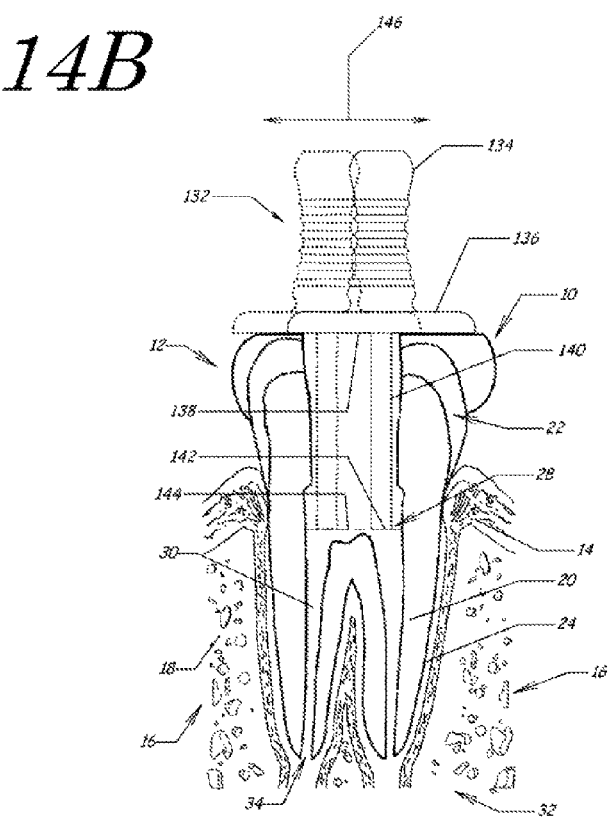
FIG. 14B schematically illustrates another example of a sizer inserted into the pulp chamber of a tooth. In this example, the sizer is the correct size for the pulp chamber. The sizer can be moved laterally across the width of the chamber, with the solid lines showing the sizer in a first position and the dotted lines showing the sizer in a different position in the pulp chamber.

With reference to the examples shown in FIGS. 14A and 14B, a set or kit of sizers can be used to measure the distance between the substantially flat surface 76 created by the tooth seal material on the occlusal surface and the highest point on the pulpal floor.

FIG. 14A schematically illustrates an example of a sizer 132 inserted into a pulp chamber 28 of an example tooth 10. In this example, the sizer 132 is too large for the pulp chamber 28. FIG. 14B schematically illustrates another example of a sizer 132 inserted into the pulp chamber 28 of a tooth 10. In this example, the sizer 132 is the desired size for the pulp chamber 28. The sizer 132 can be moved laterally across the width of the chamber, with the solid lines showing the sizer 132 in a first position and the dashed lines showing the sizer 132 in a different position in the pulp chamber 28.

In the example shown in FIGS. 14A and 14B, the sizer 132 has a handle 134 (which may be similar to that of endodontic files), a pin 140 whose length varies among sizers of different sizes, and a disk 136 separating the handle 134 from the pin 140. The handle 134 can be grasped in the fingers or by dental pliers. The distal surface 138 of the disk 136 can be substantially flat. The sizer pin 140 can be inserted into the pulp chamber 28 of the tooth 10. The dental practitioner may determine the depth or size of the pulp chamber 28 by inserting sizers 132 with different pin lengths into the pulp chamber 28. In FIG. 14A, the sizer pin 140 is too long for the pulp chamber 28, because the sizer disk 136 extends above the flat surface 76 of the tooth seal 75 when a distal end 142 of the pin 140 touches the pulp chamber floor. A shorter sizer pin 140 can be selected and moved laterally around the pulp chamber 28. This process can be repeated until a sizer pin 140 is found that does not contact the pulp floor as it is moved around the pulp chamber 28. The sizer 132 having the correct or desired length may have the longest pin 140 that does not come in contact with the pulp floor when the sizer disk 136 is placed over and slid laterally (schematically shown by solid double-headed arrow 146 in FIG. 14B) on the flat surface 76 of the tooth seal 75. FIG. 14B shows a sizer 132 with an appropriate pin length for the illustrated tooth 10, because the distal end 142 of the pin 140 is positioned an appropriate height above the pulp floor (as indicated by the horizontal dashed line 144). This sizer 132 can be used to establish the depth of the pulp chamber 28.

In another implementation, a single sizer 132 can be used. The sizer pin 140 can be marked or scaled with measurement indicia, and the sizer disk 136 can be adjustable and configured to move up or down relative to the pin 140. The dental practitioner can insert the sizer 132 into the pulp chamber 28 and move the sizer disk 136 until it contacts the upper surface 76 of the tooth seal 75. The sizer 132 is then removed from the pulp chamber 28, and the position of the disk 136 relative to the measurement indicia provides a measurement of the depth of the pulp chamber 28. The distal end of the pressure wave generator (or fluid inlet) may be positioned at a depth slightly less than the measured depth of the pulp chamber 28 so that the distal end is at a desired height above the pulp chamber floor (e.g., from about 1 mm to a 5 mm above the floor)

In other embodiments, a ruler or depth gauge graduated with suitable indicia can be inserted into the pulp chamber 28 to measure the distance from an upper surface (e.g., the flat surface 76 of a tooth seal 75, if used) to a lower surface (e.g., the floor of the pulp chamber). In other embodiments, a radiograph (e.g., X-ray) of the tooth may be taken, and the size or depth of the pulp chamber 28 determined from the radiograph.

An example method of determining a depth of a tooth chamber 65 comprises providing a kit comprising a set of sizers, where each sizer in the set is configured to measure a different tooth chamber depth. The method includes repeatedly inserting different sizers into the tooth chamber 65 to determine the depth. In some embodiments of the method, the depth is determined as the longest sizer that does not contact the pulpal floor. In some embodiments, the method includes moving a sizer laterally around the tooth chamber 65.

(3) Examples of a Cap and Sealer

The fluid retainer 66 may include a cap 70 (and an optional sealer 68) that can be sized so that a distal end of a fluid inlet 71 or pressure wave generator 64 is at a desired location in the tooth chamber 65. In some systems, each sizer 132 can be associated with a cap 70 that can be applied to the tooth. As described, the cap 70 can, in some cases, be attached to the distal end 58 of the handpiece 50 or manually applied to the tooth 10 (without using the handle of a handpiece). The cap 70 can be used so that the distal end of the fluid inlet 71 or pressure wave generator 64 is located at the desired height above the pulp floor (indicated by the horizontal dashed line 144 in FIG. 15C) when the handpiece 50 is applied to the tooth seal 75. The size increments of the caps may be substantially equal to the size increments of the pins on the sizers. After the depth of the pulp chamber 28 is determined using the sizers 132, an appropriately-sized cap can be selected and (optionally) mounted on the handpiece 50 or fluid platform 61. The cap 70 can be attached to the handpiece 50 chemically (e.g. glued, using an adhesive), mechanically (e.g., snapped or screwed), magnetically (e.g., by making the cap 70 and the distal end of the handpiece of opposite magnetic polarities), or by a combination of the foregoing. Alternatively, the cap 70 can be attached (e.g., glued) onto tooth.

In some embodiments, the cap 70 can include a sealer 68, which may be a flexible gasket (e.g., a sponge) that helps maintain water-tight or air-tight coupling between the cap 70 and the tooth seal 75, so that fluid does not leak out of the tooth 10 during treatment. A flexible sealer 68 may be able to accommodate movement of the handpiece 50 on the tooth as the dental practitioner maneuvers the handpiece into position. The sealer 68 can be disposed at the distal end of the cap 70 (see, e.g., FIG. 3A) or may be disposed inside the cap 70 (see, e.g., FIG. 3B). In some embodiments, the sealer functions as the flow restrictor 68 and inhibits backflow or splashing from the tooth chamber 65, helps retain fluid in the tooth chamber 65, and can permit air to flow into a suction line.

The sealer 68 can comprise sponge (e.g., a closed-cell foam). The sealer material advantageously may be able to withstand chemicals (e.g., bleach) used during endodontic treatments. The sealer 68 can be formed from material that is elastic to properly seal between the handpiece and the tooth. Examples include a sponge, e.g., polyvinyl foam, polyethylene, polyvinyl alcohol (PVA), cellulose foam, silicone foam, etc. Other examples include silicone, elastomer, rubber, latex, etc. In one embodiment, a material with substantially little acoustic dampening is used.

In some methods, a tooth seal is not used, and the cap 70 of the handpiece 50 (or fluid platform 61) may be applied directly to the tooth. In some such methods, the sealer 68 can provide adequate sealing between the cap 70 and the tooth 10 to inhibit flow of treatment fluid and organic matter from the tooth chamber 65 during treatment.

The cap 70 may have an internal chamber 69 that allows fluid to flow from the tooth chamber 65 into a fluid outlet 72. The internal chamber 69 may have an opening 98 that may be large enough so that a portion of a pressure wave generator 64 can pass through the opening (see, e.g., FIG. 12B). The opening 98 can be configured to be sufficiently large to allow the waste fluid to leave the pulp cavity 26 without substantial pressurization of the cavity (or canal apices) and can be configured to be small enough not to interfere with the sealing of the pulpal cavity. In some embodiments, the size of the opening can be adjusted based at least in part on the flow rate of the fluid dispensed into the chamber. In some embodiments, the opening comprises a substantially circular opening. In some such embodiments, the guide tube 100 can be disposed in the opening 98 (e.g., in the middle of the opening 98; see, e.g., FIG. 12B). In some embodiments, the effective area of the opening is in a range from about 5 mm$^2$ to 15 mm$^2$. The opening may have an area in a range from about 1 mm$^2$ to 25 mm$^2$. The sealer 68 may substantially surround the opening at the distal end of the cap 70 (see, e.g., FIG. 11).

The fluid connection created between the cap 70 and the tooth 10 (or tooth seal 75) may be flexible in nature such that the connection can accommodate movements in the handpiece related to the tooth while maintaining the fluid connection. In some embodiments, the cap 70 is formed from a durable, biocompatible material, and the sealer 68 is used to accommodate movements and provide a good fluid connection. In other embodiments, the cap 70 may be made from one or more materials with different elasticities, permeabilities, and/or degrees of firmness. For example, a softer, more permeable material can be used to engage with the tooth, reducing (or potentially eliminating) the need for a separate sealer 68. Caps can have different shapes depending on which tooth is being treated (e.g., molar, incisor, canine, etc.).

In some cases, a relatively small amount of force is used to create a positive seal between the tooth 10 (or tooth seal 75) and the cap 70. For example, in the case of a handpiece 50, the pressure applied to the handpiece 50 to form the seal can be low enough for the operator to comfortably apply during the procedure. In case where the handpiece is not handheld, the cap 70 can be applied to the tooth 10 (or tooth seal 75) without excessive clamping/holding force (e.g., by the patient biting down). The cap 70 can be used throughout the procedure and can be configured to withstand chemical exposure (such as irrigants introduced during the procedure).

(4) Examples of a Handpiece Applied to a Tooth Seal

Figure 15A:
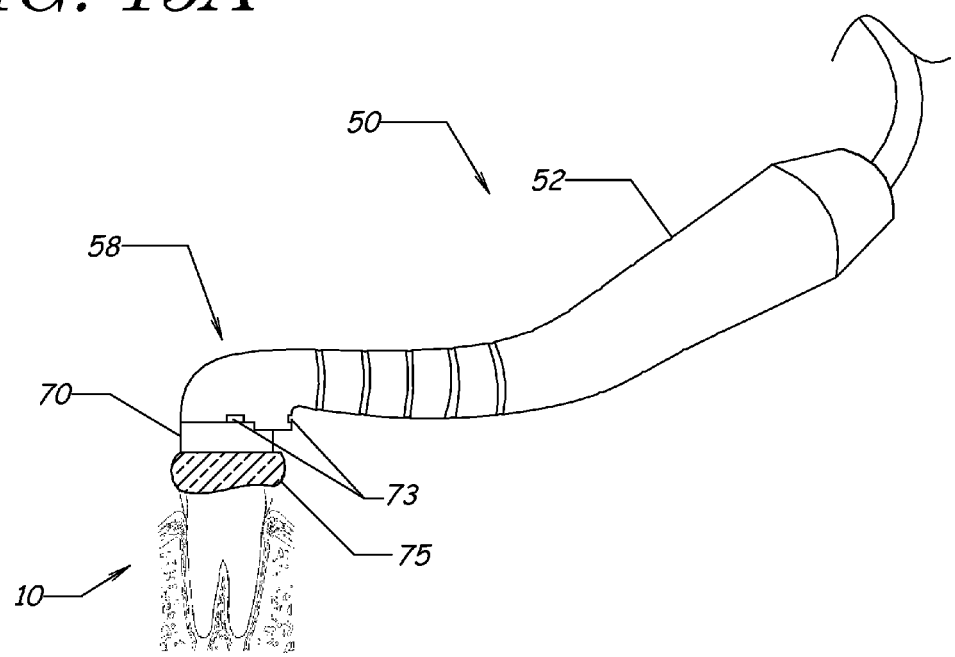
FIGS. 15A, 15B, and 15C schematically illustrate a handpiece applied to a tooth seal on a tooth.
Figure 15B:
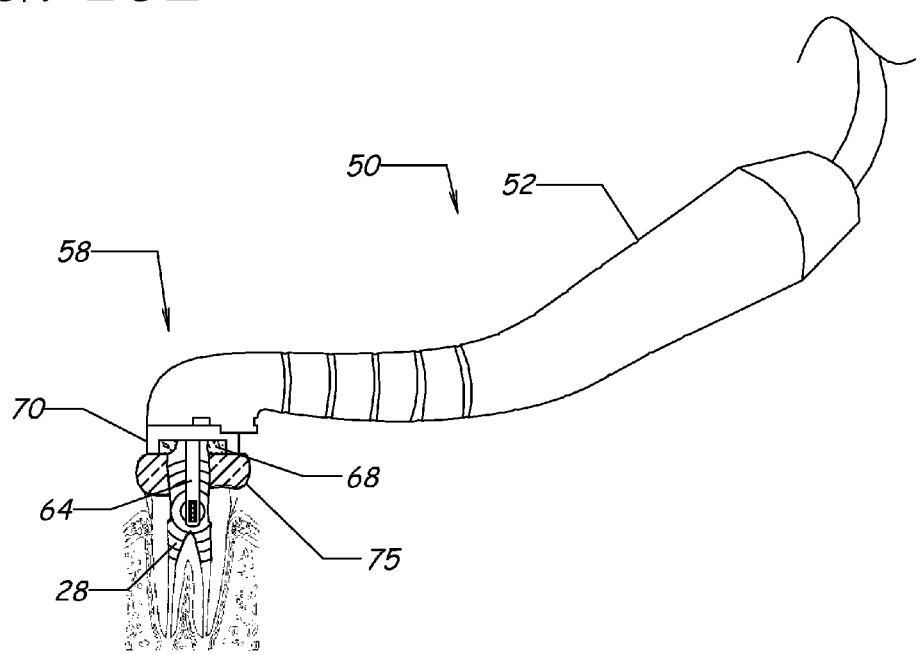
Figure 15C:
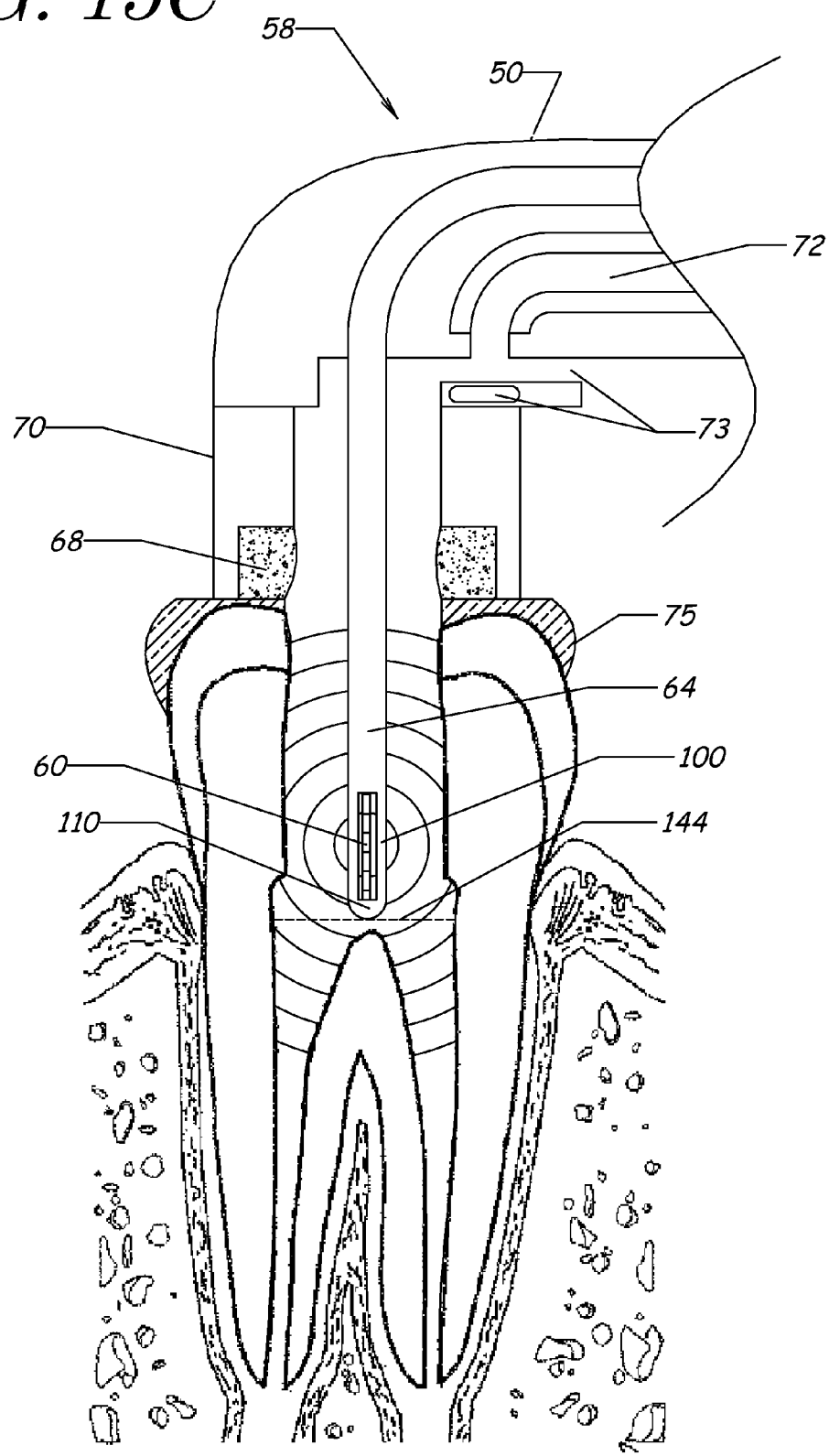

FIGS. 15A, 15B, and 15C schematically illustrate a handpiece 50 applied to a tooth seal 75 on a tooth 10. FIG. 15A is a side view, FIG. 15B is a partial cutaway view that shows a pressure wave generator 64 disposed in the tooth chamber 65, and FIG. 15C is a close-up view showing the distal end 58 of the handpiece 50 and the pressure wave generator 64.

The distal end 58 of the handpiece 50 includes a cap 70 that was selected as described above so as to position the distal end of the pressure wave generator 64 at a desired distance above the pulp chamber floor (shown by the horizontal dashed line 144 in FIG. 15C). In this example, the cap 70 includes a sealer 68 to assist in providing a substantially water-tight connection between the cap 70 and the upper surface 76 of the tooth seal 75 (see, e.g., FIGS. 15B and 15C). FIG. 15C shows that, in this example, the handpiece 50 includes the pressure wave generator 64 (a liquid jet) and a vented fluid outlet 72, 73. In this example, treatment fluid enters the cavity via the liquid jet and is removed by the fluid outlet 72.

(5) Examples of Treatment Procedures

FIGS. 16A, 16B, 16C, and 16D are flowcharts illustrating examples of techniques that may be used during various endodontic procedures. These techniques are intended to be illustrative and not limiting. The techniques can be performed in any suitable sequence. None of the techniques is necessary or indispensable to every endodontic procedure. Also, techniques can be added or removed.

Figure 16A:
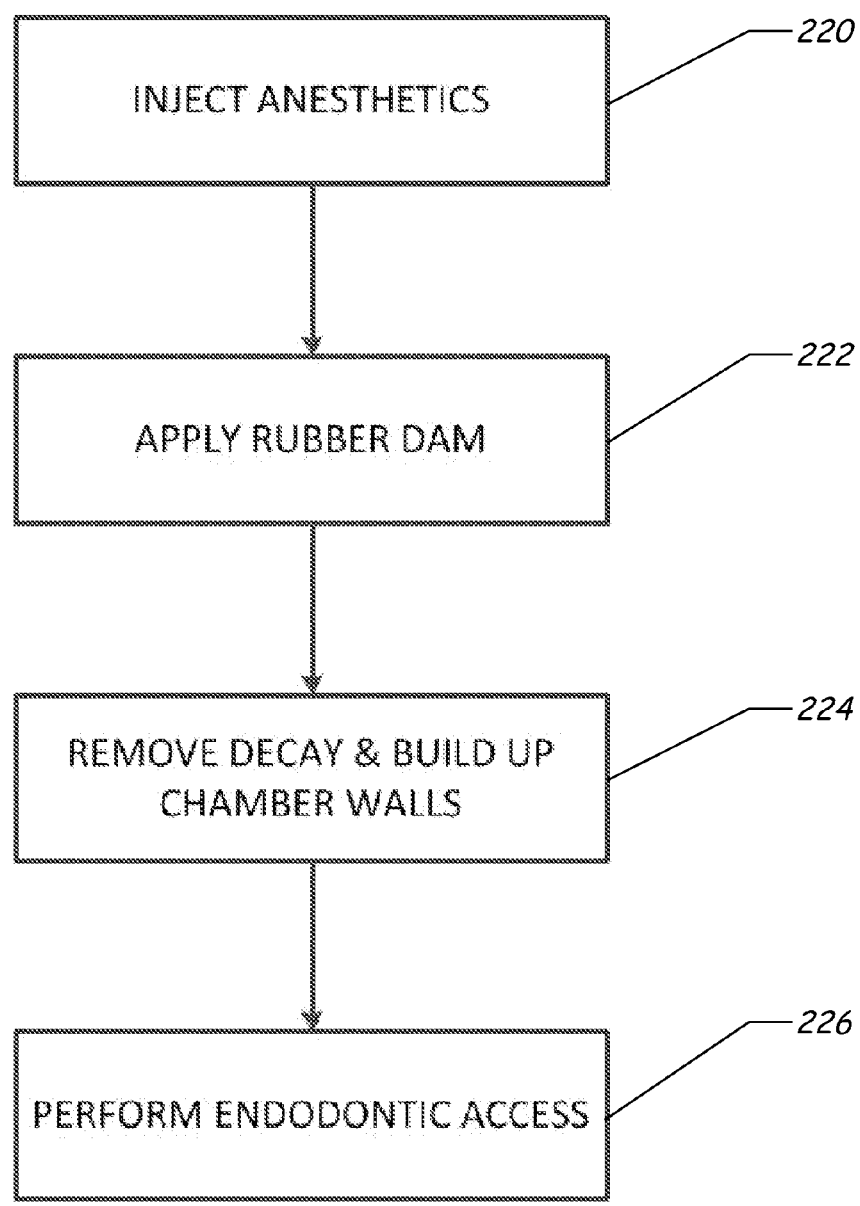
FIGS. 16A, 16B, 16C, and 16D are flowcharts illustrating examples of techniques that may be used during various endodontic procedures.

In FIG. 16A, at block 220, anesthetics can be injected into the patient to numb the tooth area. At block 222, a rubber dam can be applied to the tooth area and the rubber dam can be disinfected. At block 224, the dental practitioner may remove decay from the tooth 10 and, if necessary, build up walls of the tooth chamber 65, e.g., with a composite material or a tooth seal material. For example, the dental practitioner may decide to build up a wall due to decay or damage to the tooth structure (see, e.g., FIG. 13C). At block 226, the practitioner may then perform an endodontic access to provide an opening 25 into the tooth chamber. The access may be coronal, buccal, lingual, or any other type of access. In some procedures, multiple openings 25 can be formed, e.g., one opening to provide access to the tooth chamber for a fluid inlet or pressure wave generator and a second opening to permit fluid to drain from the tooth chamber 65.

Figure 16B:
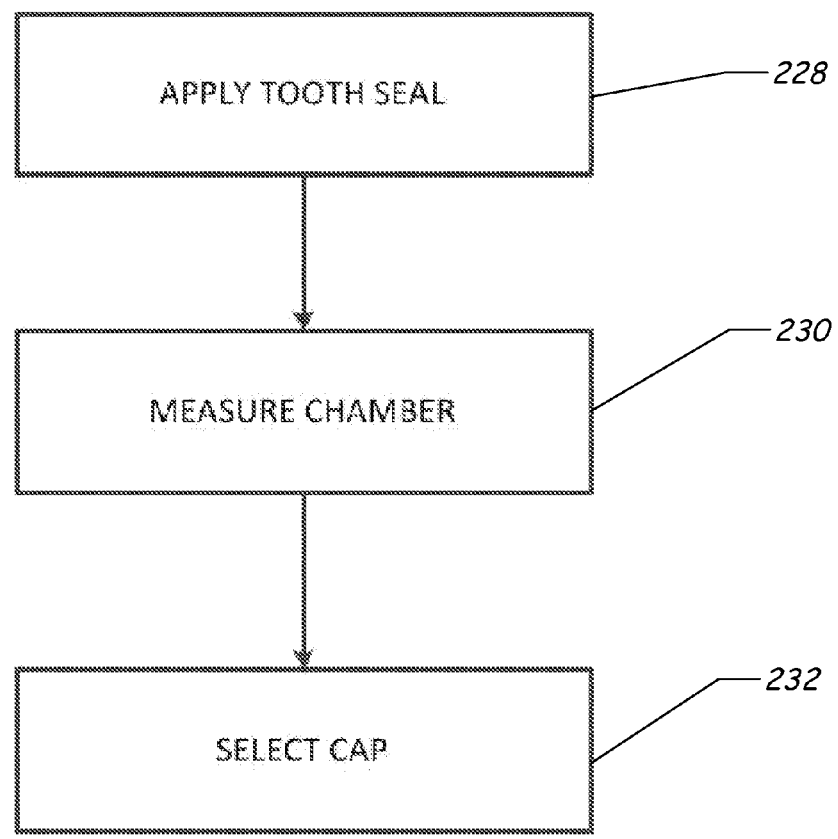
Figure 16C:
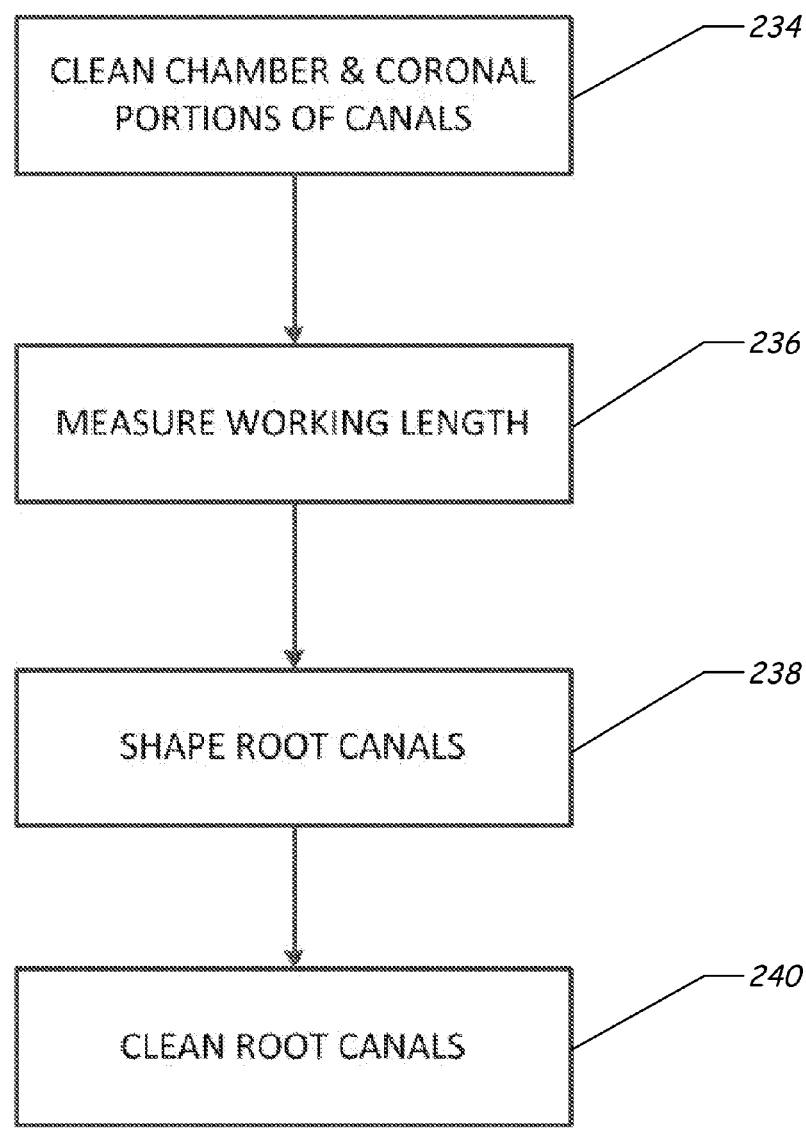

In FIG. 16B, at block 228, a tooth seal 75 may be applied to the tooth 10 to provide a substantially flat surface 76 on which the fluid platform 61 or a handpiece 50 can be applied. In some procedures, the tooth seal 75 may not be used, and, for example, a flow restrictor (e.g., a sponge) may be applied to the access opening to retain fluid in the tooth chamber. At block 230, the depth of the tooth chamber 65 can be measured. For example, the depth can be measured using a kit of one or more tooth sizers (see, e.g., FIGS. 14A and 14B) or using a graduated gauge or file. Once the desired size of the tooth chamber 65 is determined, a corresponding cap can be selected from a kit of caps at block 232. The cap may be attached to a fluid retainer (e.g., on a distal end of a handpiece 50). The cap 70 can be sized so that a distal end of a fluid inlet 71 or a distal end of a pressure wave generator 64 is at a desired position in the tooth 10, e.g., a desired distance above the pulp chamber floor. The cap 70 may include a sealer 68 (e.g., sponge or foam) to provide a substantially water-tight or air-tight connection between the cap 70 and the tooth seal 75 (or tooth, if a tooth seal is not used). As discussed herein, the cap need not In FIG. 16C, at block 234, the pulp chamber 28 and the coronal portions of the root canal spaces may be cleaned, if desired, for example, to facilitate use of an apex locator to measure working length of the canals. At block 236, the working length of a root canal space can be measured, for example, with an apex locator, an instrument (e.g., a file), or a radiograph (e.g., an X-ray). For example, the working length can be a measure of the length of a canal space from an apical constriction to a cusp on an occlusal surface of the tooth 10. If desired, at block 238, the dental practitioner can shape the root canals, e.g., to enlarge or shape the canal space as desired. At block 240, the tooth chamber 65 can be cleaned. For example, a fluid retainer 66 can be applied to the tooth and used to circulate a cleaning solution (e.g., antiseptic or antibiotic) in the tooth chamber 65 (see, e.g., FIG. 3A). A pressure wave generator 64 can be activated to generate acoustic waves 67 that propagate through the tooth 10 (see, e.g., FIG. 2A). The acoustic waves 67 can generate acoustic cavitation, which may effectively clean the root canals of the tooth 10. In some procedures, the fluid flowing from the tooth 10 may be monitored to determine when the cleaning is complete (see, e.g., FIG. 3C).

Figure 16D:
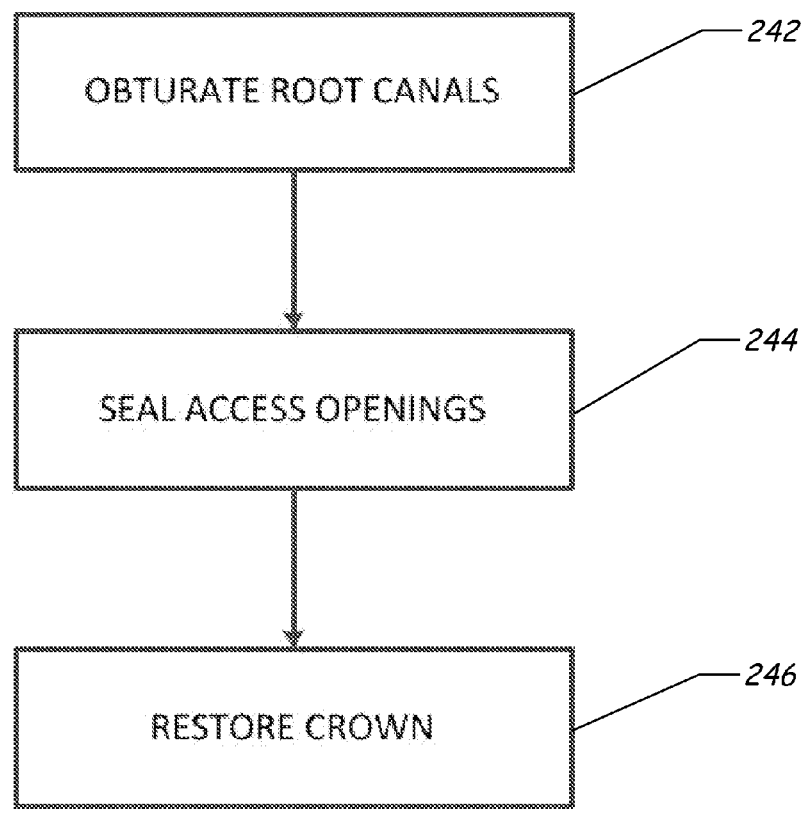

In FIG. 16D, at block 242, the tooth chamber 65 may be at least partially obturated with an obturation material to substantially fill and seal the canal spaces. In some procedures, obturation is optional, because the cleaning may be so complete that there is little likelihood of future infection or reinfection. By not obturating the tooth chamber 65, the duration and cost of the procedure may be reduced for the patient. At block 244, the access openings 25 may be sealed, for example, with a coronal seal (if a coronal access opening is used). At block 246, a crown can be restored over the access opening.

Figure 17:
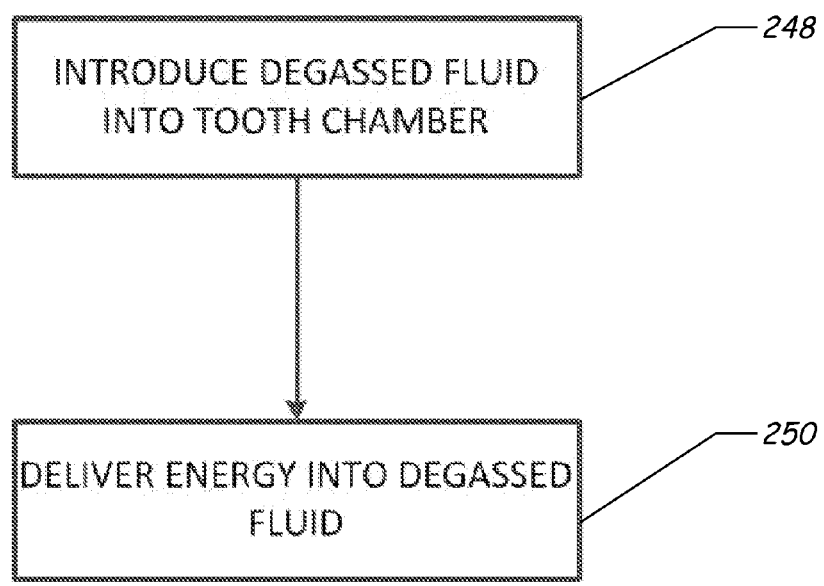
FIG. 17 is a flowchart illustrating an example method of using a degassed fluid during an endodontic procedure.

FIG. 17 is a flowchart illustrating an example method of using a degassed fluid during an endodontic procedure. In this example method, at block 248, a degassed fluid is introduced into a tooth chamber 65. The degassed fluid may be delivered from a source of degassed fluid such as, e.g., a reservoir (e.g., bottle) or may be delivered as the output from a degassing unit. The degassed fluid may be introduced into the tooth chamber using a fluid inlet or fluid introducer in various embodiments. The degassed fluid may circulate in the tooth chamber. The degassed fluid may have a sufficiently low percentage of dissolved gasses so as to penetrate openings in the dentin of the tooth having a dimension less than about 500 microns, less than about 250 microns, less than about 100 microns, less than about 50 microns, less than about 25 microns, less than about 10 microns, less than about 5 microns, or some other value. The use of degassed fluid may inhibit formation of gas bubbles in the tooth chamber.

Energy may be delivered into the degassed fluid. For example, at block 250, acoustic waves may be generated in the degassed fluid in the tooth. The acoustic waves may, but need not, generate acoustic cavitation in fluid in the tooth. The acoustic waves may propagate through the degassed fluid to surrounding dentin structure of the tooth. Block 250 can be optional in some procedures, as the flowing degassed fluid may be used to irrigate tooth tissue. Also, the degassed fluid may include solutes (e.g., an antiseptic, antibiotic, or decalcifying agent) that may clean the tooth chamber. The degassed fluid may inhibit the formation of gas bubbles in the tooth chamber, and may allow the degassed fluid to flow into small tooth spaces (e.g., tubules, small canals) to provide more effective cleaning.

In some implementations, an apparatus for treating a tooth can be used to implement embodiments of the method shown in FIG. 17. The apparatus can comprise a degassed liquid source, and a fluid introducer that is configured to supply fluid from the degassed liquid source to a tooth chamber formed in a tooth.

III. ADDITIONAL EXAMPLE ASPECTS OF PRESSURE WAVE TISSUE CLEANING

It is believed, although not required, that some or all of the effects described below may be at least in part responsible for advantageous effects, benefits, or results provided by various implementations of the treatment methods and systems described herein. Accordingly, various embodiments of the systems disclosed herein can be configured to provide some or all of these effects.

In the following description, unless a different meaning is indicated, the following terms have their ordinary and customary meaning. For example, a chemical reaction front may generally refer to an interface between the tissue and the solution which contains a chemical such as a tissue dissolving agent. Tissue may refer to all types of cells existing in the tooth as well as bacteria and viruses. Calcified tissue may refer to calcified pulp, pulp stones, and tertiary dentin. Bubbles includes but is not limited to bubbles created due to a chemical reaction, dissolved gas remaining in the fluid after degassing (if used) and released as bubbles in the fluid, and any bubbles which are introduced into the tooth due to imperfect sealing.

Tissue cleaning treatments may utilize one or more of the physicochemical effects described herein to clean and remove tissue and/or calcified tissue from a tooth chamber. In some cleaning treatments, the combination of (1) pressure waves (e.g., generation of acoustic cavitation), (2) circulation of fluid in the tooth chamber (e.g., macroscopic eddies and flows), and (3) chemistry (e.g., use of a tissue dissolving agent, use of degassed fluids) can provide highly effective cleaning. Accordingly, certain embodiments of the systems disclosed herein utilize a pressure wave generator to generate the acoustic waves, a fluid platform (e.g., fluid retainer) to retain treatment fluid in the tooth chamber and to enable circulation of the treatment fluid, and a treatment fluid that is degassed or includes a chemical agents such as a tissue dissolving agent.

A. Acoustic Waves

A pressure wave generator can be used to generate pressure waves that propagate through the fluid in the tooth chamber (and the tooth). Upon irradiation of a fluid with high intensity pressure waves (e.g., sonic or ultrasonic frequencies), acoustic cavitation may occur. As has been described herein, the implosive collapse of the cavitation bubbles can produce intense local heating and high pressures with short lifetimes. Therefore, in some treatment methods, acoustic cavitation may be responsible for or involved in enhancing chemical reactions, sonochemistry, sonoporation, tissue dissociation, tissue delamination, as well as removing the bacteria and/or the smear layer from the root canals and tubules. The effects of enhancing chemical reaction via vibrations or sonochemistry will be described below in the section on chemistry.

Sonoporation is the process of using an acoustic field (e.g., ultrasonic frequencies in some cases) to modify the permeability of the cell plasma membrane. This process may greatly expedite the chemical reaction. It may be advantageous if the acoustic field has a relatively broad bandwidth (e.g., from hundreds to thousands of kHz). Some frequencies (e.g., low frequency ultrasound) may also result in cellular rupture and death (e.g., lysis). This phenomenon may kill bacteria which might otherwise reinfect the tooth. Pressure waves and/or acoustic cavitation may loosen the bond between cells and/or may dissociate the cells. Pressure waves and/or acoustic cavitation may loosen the bond between cells and dentin and/or delaminate the tissue from the dentin.

For removing calcified tissue, pressure waves may induce sonochemistry and microscopic removal of calcified structures due to shock waves and/or microjets created as a result of cavitation bubble implosion. Pressure waves may break microscopic calcified structures through structural vibrations. If a chemical (e.g., a chelating agent such as, e.g., EDTA) is used for this procedure, the pressure waves may enhance the chemical reaction.

Certain properties of the system can be adjusted to enhance the effects of the acoustic waves. For example, properties of the fluid including, e.g., surface tension, boiling or vapor temperature, or saturation pressure can be adjusted. A degassed fluid with a reduced dissolved gas content can be used, which may reduce the energy loss of pressure waves that may be generated by hydrodynamic cavitation or any other sources. The fluid can be degassed, which may help preserve the energy of the pressure waves and may increase the efficiency of the system.

B. Fluid Circulation

Some treatment systems and methods use diffusion and/or ultrasonically enhanced diffusion of reactants and byproducts to and away from the chemical reaction front. However, due to the relatively short time scale of the reaction process, a faster mechanism of reactant delivery such as "macroscopic" circulation, convection, voracity, or turbulence may be advantageous in some of the embodiments disclosed herein. For example, fluid inflow into the tooth chamber may induce a macroscopic circulation in the pulp cavity (see, e.g., FIG. 3B). A liquid jet device not only may create pressure waves but may also induce circulation as the jet and/or spray enter the tooth chamber. Other pressure wave generators can produce fluid circulation via their interaction with ambient fluid (e.g., via localized heating of the fluid, which may induce convection currents and circulation).

Fluid circulation with a time scale comparable to (and preferably faster than) that of chemical reaction may help replenish the reactants at a chemical reaction front and/or may help to remove reaction byproducts from the reaction site. The convective time scale, which may relate to effectiveness of the convection or circulation process, can be adjusted depending on, e.g., the location and characteristics of the source of circulation. The convective time scale is approximately the physical size of the tooth chamber divided by the fluid speed in the tooth chamber. Introduction of circulation generally does not eliminate the diffusion process, which may still remain effective within a thin microscopic layer at the chemical reaction front. Fluid circulation may create flow-induced pressure oscillations inside the root canal which may assist in delaminating, loosening, and/or removing larger pieces tissue from the root canal.

For removing calcified tissue, fluid circulation may create flow-induced pressure oscillations inside the root canal which may assist in removing larger pieces of calcified structures from the root canal.

Certain properties of the system can be adjusted to enhance the effects of the circulation in the tooth. For example, the location of the source of circulation inside the tooth, the source flow characteristics such as shape (e.g. planar vs. circular jets) or velocity and/or direction of a fluid stream, and the fluid kinematic viscosity may be adjusted. The circulation may also be effected by the anatomy of the tooth or the canal orifice or root canal size. For example, a narrow root canal with constrictions may have a lower solution replenishment rate than a wide canal with no constrictions. If the source of convection/circulation is placed near the pulp chamber floor, a tooth with a smaller pulp chamber may have stronger circulation than one with a larger pulp chamber. Convection-induced pressure exerted at the periapical region of the tooth may be controlled to reduce or avoid extrusion of the treatment fluid into the periapical tissues. Large magnitude vacuum or low pressure in the tooth may cause discomfort in some patients. Thus, the properties of the fluid platform (e.g., vents, sponges, flow restrictors, etc.) can be adjusted to provide a desired operating pressure range in the tooth chamber.

C. Chemistry

A tissue dissolving agent (e.g., sodium hypochlorite) may be added to the treatment fluid to react with tissue. Tissue dissolution may be a multi-step and complex process. Dissolution of sodium hypochlorite in water can include a number of reactions such as, e.g., the sodium hypochlorite (bleach) reaction, a saponification reaction with triglycerides, an amino acid neutralization reaction, and/or a chloramination reaction to produce chloramine. Sodium hypochlorite and its by-products may act as dissolving agents (e.g. solvents) of organics, fats, and proteins; thereby, degrading organic tissue in some treatments.

Sodium hypochlorite may exhibit a reversible chemical equilibrium based on the bleach reaction. Chemical reactions may occur between organic tissue and sodium hypochlorite. For example, sodium hydroxide can be generated from the sodium hypochlorite reaction and can react with organic and fat (triglycerides) molecules to produce soap (fatty acid salts) and glycerol (alcohol) in the saponification reaction. This may reduce the surface tension of the remaining solution. Sodium hydroxide can neutralize amino acids forming amino acid salts and water in the amino acid neutralization reaction. Consumption of sodium hydroxide can reduce the pH of the remaining solution. Hypochlorous acid, a substance that can be present in sodium hypochlorite solution, can release chlorine that can react with amino groups of proteins and amino acids to produce various chloramines derivatives. For example, hypochlorous acid can react with free amino acids in tissue to form N-chloro amino acids which can act as strong oxidizing agents that may have higher antiseptic activity than hypochlorite.

Chemical(s) in the fluid, depending on their type, may affect the surface tension of the solution, which in turn may modify the cavitation phenomenon. For example, solution of an inorganic chemical such as, e.g., sodium hypochlorite in water, may increase the ion concentration in the solution which may increase the surface tension of the solution, which may result in stronger cavitation. In some cases, the magnitude of a cavitation inception threshold may increase with increasing surface tension, and the cavitation inducing mechanism (e.g., a pressure wave generator) may be sufficiently intense to pass the threshold in order to provide inception of cavitation bubbles. It is believed, but not required, that once the cavitation threshold is passed, increased surface tension may result in stronger cavitation. Reducing the dissolved gas content of a fluid (e.g., via degassing) can increase the surface tension of the fluid and also may result in stronger cavitation. Addition of chemicals, agents, or substances (e.g., hydroxyl functional groups, nanoparticles, etc.) to the treatment may increase the efficiency of conversion of a pressure wave into cavitation, and such chemoacoustic effects may be desirable in some treatment procedures.

In some methods, a chemical, such as sodium hypochlorite, may cause saponification. The removal of bubbles created or trapped inside the root canals (or tubules) may be accelerated due to local reduction of surface tension at the chemical reaction front as a result of saponification. Although in some methods it may be desirable to have a relatively high surface tension at the pressure wave source (e.g. inside the pulp chamber), inside the canals it may be beneficial to have locally reduced surface tension to accelerate bubble removal. This phenomenon may happen as tissue dissolving agent(s) react with the tissue. For example, sodium hypochlorite can act as a solvent degrading fatty acids, transforming them into fatty acid salts (soap) and glycerol (alcohol) that can reduce the surface tension of the remaining solution at the chemical reaction front.

A number of variables or factors may be adjusted to provide effective cleaning. For example, each chemical reaction has a reaction rate determining the speed of reaction. The reaction rate may be dependent on several parameters including temperature. The concentration of reactants can be a factor and may affect the time for the reaction to complete. For instance, a 5% sodium hypochlorite solution generally may be more aggressive than a 0.5% sodium hypochlorite solution and may tend to dissolve tissue faster.

The refreshment rate of reactants may be affected by some or all of the following. Bubbles may form and stay at the chemical reaction front (e.g., due to surface tension forces) and may act as barriers at the chemical reaction front impeding or preventing fresh reactants from reaching the reaction front. Accordingly, circulation of the treatment fluid can help remove the bubbles and the reaction byproducts, and may replace them with fresh treatment fluid and fresh reactants. Thus, use of an embodiment of the fluid platform that can provide fluid circulation in the tooth chamber advantageously may improve the cleaning process.

Heat may increase the chemical reaction rate and may be introduced through a variety of sources. For example, the treatment solution may be preheated before delivery to the tooth chamber. Cavitation, exothermic chemical reactions, or other internal or external dissipative sources may produce heat in the fluid, which may enhance, sustain, or increase reaction rates.

Sonication of the fluid may increase chemical reaction rates or effectiveness. For example, upon irradiation of a fluid (e.g., water) with high intensity pressure waves (including, e.g., sonic or ultrasonic waves, or broad spectrum acoustic power produced by a liquid jet) acoustic cavitation may occur. The implosive collapse of the cavitation bubbles can produce intense local heating and high pressures with short lifetimes. Experimental results have shown that at the site of the bubble collapse, the temperature and pressure may reach around 5000 K and 1000 atm, respectively. This phenomenon, known as sonochemistry, can create extreme physical and chemical conditions in otherwise cold liquids. Sonochemistry, in some cases, has been reported to enhance chemical reactivity by as much as a million fold. In cases where acoustic cavitation does not occur (or occurs at a relatively low amplitude), the vibration of reactants, due to the pressure waves, may enhance the chemical reaction as it assists in replacing the byproducts by fresh reactants.

For removing calcified tissue, a decalcifying agent (e.g., an acid such as, e.g., EDTA or citric acid) may be added to the treatment fluid. The decalcifying agent may remove calcium or calcium compounds from the tooth dentin. The substances remaining after treatment with the decalcifying agent may be relatively softer (e.g., gummy) than prior to treatment and more easily removable by the fluid circulation and acoustic waves.

IV. ADDITIONAL EXAMPLES AND EMBODIMENTS

Additional examples and embodiments of apparatus, methods, and compositions will be described. The examples are intended to illustrate and not limit the disclosure. Accordingly, all possible combinations and subcombinations of the features described below can be included in other embodiments. Additional features can be added or features can be removed. The features can be rearranged. In the procedures and methods, the operations or acts are not limited to the disclosed sequence, and the operations or acts may be performed in a different sequence.

Fluids as described herein generally means liquids, and the liquids may include a certain amount of dissolved gas. For example, a fluid can include water (having a normal dissolved gas (e.g., air) content as can be determined from Henry's law for the appropriate temperature and pressure conditions) or degassed water, which can have a reduced dissolved gas content as compared to water with a normal dissolved gas content. A tooth chamber may include at least a portion of any space, opening, or cavity of the tooth, including any portion of spaces, openings, or cavities already present in the tooth (either by normal or abnormal dentin and/or tissue structure or by degeneration, deterioration, or damage of such structure) and/or any portion of spaces, openings, or cavities formed by a dental practitioner during a treatment. For example, the tooth chamber may include at least a portion of the pulp chamber and may also include at least a portion of one or more of the following: an access opening to the tooth, a root canal space, and a tubule. In some treatments, the tooth chamber can include some or all of the root canal spaces, accessory canals, and tubules in the tooth. In some procedures, the access opening can be formed apart or separately from the tooth chamber.

1. Examples of Procedures with Fluid Platforms and Pressure Wave Generators

In one aspect, a procedure for treating a tooth is disclosed. The procedure comprises forming at least an access opening into a tooth chamber in a tooth, introducing fluid into at least a portion of the tooth chamber to provide a fluid level in the tooth, and using a fluid retainer to inhibit uncontrolled flow of fluid from the tooth chamber. The procedure may further comprise inserting a pressure wave generator into the tooth chamber and at least partially below the fluid level, activating the pressure wave generator in the tooth chamber to produce acoustic energy waves in the fluid, and maintaining the fluid in the tooth chamber such that the pressure wave generator remains submerged below the fluid level during at least a portion of the procedure.

In some aspects, the procedure may further comprise introducing fluid comprising introducing a degassed liquid. The procedure may further comprise using the fluid retainer to inhibit uncontrolled flow of fluid, including retaining sufficient fluid within the tooth chamber to permit the acoustic energy waves to propagate within the fluid, wherein the acoustic energy waves retain sufficient energy to create at least some fluid cavitation within the tooth chamber. Using the fluid retainer may comprise substantially inhibiting air flow into the tooth chamber, additionally comprising removing waste fluid from the tooth chamber, and substantially inhibiting leakage of introduced fluid, waste fluid, and organic material from the tooth chamber. In another aspect, using the fluid retainer may comprise permitting at least some of the fluid to leave the tooth chamber while substantially inhibiting air from entering the chamber.

In other aspects, using the fluid retainer may involve positioning a cap around the tooth chamber such that the cap substantially closes the access opening into the tooth chamber. The procedure may further comprise positioning the cap on a tooth seal region of the tooth, wherein the tooth seal region comprises a tooth seal, and wherein positioning the cap on the tooth seal region comprises planarizing a surface of the tooth seal. In some embodiments, using the fluid retainer may also involve positioning a flow restrictor around the tooth chamber and within the cap. The procedure may further comprise positioning the cap on the tooth seal region, which may substantially seal the tooth chamber so as to allow for controlled ingress and egress of fluid. Using the fluid retainer may also comprise providing a vent to regulate fluid pressure within the tooth chamber. Providing the vent may include permitting at least some air flow to be entrained with fluid removed from the tooth chamber. In some other aspects, providing the vent includes permitting at least some air flow to be entrained with fluid removed from the tooth chamber and may further comprise providing a fluid outlet configured to permit fluid to flow from the tooth chamber.

Using the fluid retainer may maintain the fluid pressure within the tooth at pressures below a predetermined pressure level. The procedure may further comprise activating the pressure wave generator, which may comprise activating a fluid jet. Activating the pressure wave generator may also comprise activating a laser, and activating the pressure wave generator may create at least some fluid cavitation in the tooth chamber.

2. Examples of Procedures Using Energy Beams Impacting an Instrument Surface

In another aspect, a procedure for treating a tooth is disclosed. The procedure comprises forming at least an access opening into a tooth chamber in a tooth, introducing fluid into at least a portion of the tooth chamber to provide a fluid level in the tooth, and inserting an instrument surface into the tooth chamber, the instrument surface below the fluid level during at least a portion of the procedure. The procedure may further comprise impacting the instrument surface with an energy beam to produce acoustic energy waves in the fluid, and maintaining the fluid in the tooth chamber such that the instrument surface remains submerged below the fluid level during at least a portion of the procedure.

In other aspects, introducing the fluid comprises introducing a degassed liquid. Further, in some embodiments, impacting the instrument surface with the energy beam produces sufficient acoustic energy for the acoustic energy waves to cause at least some fluid cavitation within the tooth chamber, and may further comprise substantially clearing the tooth chamber of organic matter. In another aspect, the procedure may comprise activating a pressure wave generator to create the energy beam. Activating the pressure wave generator may comprise activating a fluid jet. Activating the fluid jet may include introducing a high velocity beam of degassed liquid into the tooth chamber. In other aspects, activating the fluid jet comprises impacting the instrument surface with the jet. Inserting the instrument surface into the tooth chamber may include inserting a distal portion of an instrument into the tooth chamber. The instrument may include a channel having an opening in a distal portion of the channel. In some aspects, activating the fluid jet includes propagating the fluid jet through the channel. Impacting the instrument surface with the fluid jet may comprise deflecting the fluid jet from the instrument surface and discharging the fluid jet through the opening in the channel.

In another embodiment, activating the pressure wave generator comprises activating a laser, while in another aspect, activating the pressure wave generator comprises activating an ultrasonic device. In yet another aspect, activating the pressure wave generator comprises activating a mechanical stirrer. In yet another aspect, activating the pressure wave generator creates at least some fluid cavitation in the tooth chamber.

3. Examples of Procedures with Fluid Jet Beams

In yet another aspect, a procedure for treating a tooth is disclosed. The procedure comprises forming at least an access opening into a tooth chamber in a tooth, providing a fluid jet beam by passing fluid through an orifice, and introducing the fluid jet beam into the tooth chamber, the fluid jet beam discharging from a distal portion of an instrument. The procedure may further comprise providing a fluid level in the tooth, positioning the distal portion of the instrument in the tooth chamber, the distal portion of the instrument below the fluid level during at least a portion of the procedure, and maintaining the fluid in the tooth chamber such that the distal portion of the instrument remains submerged below the fluid level during at least a portion of the procedure.

In other aspects, introducing the fluid jet beam into the tooth chamber may include producing acoustic energy wave. Providing the fluid jet beam may comprise imparting sufficient energy to the fluid jet beam to produce acoustic energy waves. The procedure may further comprise maintaining the fluid at a sufficient fluid level to permit propagation of the acoustic energy waves and imparting sufficient energy to the fluid jet beam to produce at least some fluid cavitation within the tooth chamber. The method may further comprise substantially clearing the tooth chamber of organic matter.

In other embodiments, introducing the fluid jet beam may include impacting an impingement surface with the fluid jet beam to produce acoustic energy waves in the fluid. In another aspect, introducing the fluid jet beam comprises passing the fluid jet beam through a channel of the instrument, and may further comprise providing an impingement surface near the distal portion of the instrument, and impacting the impingement surface with the fluid jet beam. The procedure may further comprise providing a vented fluid outlet to enable fluid removal from the tooth chamber and to limit overpressurization, underpressurization, or both overpressurization and underpressurization of the tooth chamber. The procedure may further comprise providing a vented fluid inlet to enable fluid delivery to the tooth chamber and to limit overpressurization, underpressurization, or both overpressurization and underpressurization of the tooth chamber. In some aspects, impacting the impingement surface and discharging the fluid jet beam may produce acoustic energy waves that cause at least some fluid cavitation within the tooth chamber. In some embodiments, providing a fluid jet beam may comprise producing a high velocity beam of degassed liquid.

4. Examples of Procedures Using Broadband Frequency Pressure Wave Generators

In yet another aspect, a procedure for treating a tooth is disclosed. The procedure comprises forming at least an access opening into a tooth chamber in a tooth, introducing fluid into at least a portion of the tooth chamber to provide a fluid level in the tooth, and inserting at least a portion of a pressure wave generator into the tooth chamber, the at least a portion of the pressure wave generator below the fluid level during at least a portion of the procedure. The procedure may further comprise producing with the pressure wave generator acoustic energy waves of a broadband spectrum in the fluid, and maintaining the fluid in the tooth chamber such that the portion of the pressure wave generator remains submerged below the fluid level.

In other embodiments, introducing the fluid may comprise introducing degassed liquid into at least the portion of the tooth chamber. The procedure may further comprise producing sufficient acoustic energy to cause at least some fluid cavitation within the tooth chamber. In some aspects, inserting at least the portion of the pressure wave generator into the tooth chamber comprises providing a fluid jet beam within the tooth chamber, and may further comprise impacting an impingement surface with the fluid jet beam.

In some aspects of the procedure, a substantial amount of the acoustic energy waves propagate at frequencies above about 0.5 kHz, while in other aspects, a substantial amount of the acoustic energy waves propagate at frequencies above about 1 kHz, about 10 kHz, or about 100 kHz. In some aspects of the procedure, the acoustic energy waves have a power with a bandwidth of at least 50 kHz, while in other aspects, the acoustic energy waves have a power with a bandwidth of at least 100 kHz. In some embodiments, the acoustic energy waves have a power with a bandwidth of at least 500 kHz, while in other embodiments, the acoustic energy waves have a power with a bandwidth between about 50 kHz and about 500 kHz. Additionally, inserting at least the portion of the pressure wave generator into the tooth chamber may comprise activating a laser. In other aspects, inserting at least the portion of the pressure wave generator into the tooth chamber may comprise activating an ultrasonic device. In yet other aspects, inserting at least the portion of the pressure wave generator into the tooth chamber may comprise activating a mechanical stirrer.

5. Examples of Procedures Using Pressure Wave Generators with Energy Above 1 kHz In yet another embodiment, a procedure for treating a tooth is disclosed. The procedure comprises forming at least an access opening into a tooth chamber in a tooth, introducing fluid into at least a portion of the tooth chamber to provide a fluid level in the tooth, and inserting at least a portion of a pressure wave generator into the tooth chamber below the fluid level. The procedure may further comprise producing with the pressure wave generator acoustic energy waves, at least a substantial amount of the acoustic energy waves having frequencies of 1 kHz or greater, and maintaining the fluid in the tooth chamber such that the portion of the pressure wave generator remains submerged below the fluid level during at least a portion of the procedure.

In other aspects, introducing the fluid may comprise introducing degassed liquid into at least the portion of the tooth chamber, and the procedure may also comprise producing sufficient acoustic energy to cause at least some fluid cavitation within the tooth chamber. Further, inserting at least the portion of the pressure wave generator into the tooth chamber may comprise providing a fluid jet beam within the tooth chamber, and may further comprise impacting an impingement surface with the fluid jet beam. In some aspects of the procedure, the acoustic energy waves may propagate at least at frequencies above about 0.5 kHz, while in other aspects, the acoustic energy waves may propagate at least at frequencies at least above about 1 kHz, 10 kHz, 50 kHz, or 100 kHz. Inserting at least the portion of the pressure wave generator into the tooth chamber may also comprise activating a laser, and in some other embodiments, inserting at least the portion of the pressure wave generator into the tooth chamber comprises activating an ultrasonic device. Additionally, inserting at least the portion of the pressure wave generator into the tooth chamber may comprise activating a mechanical stirrer.

6. Examples of Apparatus Having a Fluid Retainer

In another aspect, an apparatus for treating a tooth is disclosed. The apparatus comprises a fluid retainer configured to be applied to the tooth to substantially retain fluid in a tooth chamber in the tooth, and a pressure wave generator having a distal portion. The distal portion of the pressure wave generator can be configured to be inserted into the tooth chamber.

The distal portion of the pressure wave generator may be inserted through the fluid retainer so as to be inserted into the tooth chamber. For example, the distal portion may be inserted through a sponge-like material that retains fluid in the tooth chamber. The distal portion of the pressure wave generator may be attached to a distal portion of the fluid retainer so that when the fluid retainer is applied to the tooth, the distal portion of the pressure wave generator is inserted into the tooth chamber.

The fluid retainer may be configured to be applied to the tooth, for example, by placing the retainer on an occlusal surface of the tooth (with or without an adhesive or flow restrictor such as a sponge), by covering or plugging an access opening to the tooth chamber, by wrapping a portion of the fluid retainer around the tooth, etc.

The fluid retainer can substantially retain fluid in the tooth chamber. For example, the fluid retainer can retain most or substantially all of the fluid in the tooth chamber by providing a water-resistant seal between the retainer and the tooth. The fluid retainer may, but need not, retain all the fluid in the tooth. For example substantially retaining fluid in the tooth chamber does not require that there be no amount of leakage of the fluid from the tooth chamber. The fluid retainer can be applied to the tooth to reduce or minimize the amount of fluid that leaks into the patient's mouth during treatment, which may improve patient safety and experience since some fluids can contain caustic or unpleasant tasting substances.

In other embodiments, the apparatus may comprise a body. The body can include the fluid retainer and one or more vents configured to permit at least some of the fluid to leave the tooth chamber while inhibiting air from entering the tooth chamber. The vent can be configured to permit at least some air flow to be entrained with fluid leaving the tooth chamber. In some aspects, the body may further comprise a fluid outlet configured to permit fluid to flow from the tooth chamber. The body may further comprise a handpiece. Additionally, the pressure wave generator may be configured to generate acoustic energy waves, and the fluid retainer may be configured to retain sufficient fluid within the tooth chamber to permit acoustic energy waves to propagate within the fluid. A substantial amount of the acoustic energy waves generated by the pressure wave generator can retain sufficient energy to create at least some fluid cavitation within the tooth chamber. The fluid retainer can comprise at least one vent to regulate pressure within the tooth chamber. The at least one vent may be disposed along a fluid inlet, along a fluid outlet, or on both the fluid inlet and the fluid outlet.

In some aspects, the fluid retainer comprises a flow restrictor. In some embodiments, the flow restrictor may comprise a sponge, and in some embodiments, the flow restrictor may comprise a vent. In yet other embodiments, the fluid retainer may be configured to substantially inhibit air flow into the tooth chamber. The fluid retainer may include at least one outlet. The fluid retainer may be configured to substantially inhibit leakage of fluid, organic material, or both from the tooth chamber. The fluid retainer may also be configured to permit at least some of the fluid to leave the tooth chamber, and to substantially inhibit air from entering the tooth chamber. In some aspects, the fluid retainer may comprise a cap, wherein the cap may be positioned around the tooth chamber such that the cap substantially closes an access opening into the tooth chamber. The cap may also be positioned on a tooth seal region of the tooth, wherein the cap may include a planar surface that mates to a tooth seal having a planar surface.

In some embodiments, the fluid retainer may comprise a flow restrictor positioned around the tooth chamber and within the cap, and in other aspects, the cap may substantially seal the tooth chamber so as to allow for controlled ingress and egress of fluid. In other aspects, the fluid retainer may be configured to maintain the fluid pressure within the tooth at pressures below a predetermined pressure level. In yet other aspects, the pressure wave generator may comprise one or more devices selected from the group consisting of: a fluid jet, a laser, a mechanical stirrer, and an ultrasonic device. The pressure wave generator may also be configured to create at least some fluid cavitation in the tooth chamber. In some embodiments, the fluid retainer may comprise one or more vents configured to permit at least some of the fluid to leave the tooth chamber while inhibiting air from entering the tooth chamber, wherein the pressure may be regulated to be above about −300 mmHg and below about +300 mmHg.

7. Examples of Apparatus Including Pressure Wave Generators Having a Reverberation Surface In yet another embodiment, an apparatus for treating a tooth is disclosed. The apparatus comprises a pressure wave generator having an energy guide and a distal portion with a reverberation surface. The energy guide can be arranged relative to the reverberation surface so as to direct a beam of energy onto the reverberation surface to produce acoustic pressure waves. The distal portion can be sized or shaped to fit within a tooth chamber in a tooth.

The energy guide can be arranged relative to the reverberation surface, for example, by being positioned or spaced a distance away from the reverberation surface and oriented so that the beam of energy can intercept the reverberation surface.

In some aspects, the beam of energy may comprise a fluid jet beam. The fluid jet beam may comprise degassed liquid. In other embodiments, the pressure wave generator comprises one or more devices selected from the group consisting of: a fluid jet source, a laser, an ultrasonic device, and a mechanical stirrer. Further, the energy guide may also comprise a guide tube having a channel with an opening on the distal portion of the guide tube. The pressure wave generator can be configured to output sufficient energy so as to cause at least some fluid cavitation within the tooth chamber.

8. Examples of Apparatus with Pressure Wave Generators Including an Impact Surface In another aspect, an apparatus for treating a tooth is disclosed. The apparatus comprises a pressure wave generator having a fluid beam forming portion including an orifice and an impact surface. The impact surface may be spaced from the orifice and positioned such that an axis through the orifice extends to the impact surface. The impact surface may be configured to be inserted into a tooth chamber in a tooth.

In other aspects, the fluid beam forming portion may be configured to form a fluid jet beam that will substantially impact the impact surface. The fluid beam forming portion may be configured to form a fluid jet beam having sufficient energy to cause at least some cavitation within the tooth chamber when the fluid jet beam impacts the impact surface. The apparatus may further comprise a guide tube having a channel extending along the axis and configured to permit the fluid jet beam to flow therethrough.

In some aspects, the apparatus may also comprise a fluid retainer positioned around the pressure wave generator such that the fluid retainer substantially closes an access opening into the tooth chamber. The fluid retainer may be configured to retain at least some fluid within the tooth chamber. The apparatus may further comprise a body. The body can comprise one or more vents configured to permit at least some of the fluid in the tooth chamber to leave the tooth chamber while substantially inhibiting air from entering the tooth chamber. Further, the one or more vents may be configured to permit at least some air flow to be entrained with fluid leaving the tooth chamber. In some aspects, the body may further comprise a fluid outlet configured to permit fluid to flow from the tooth chamber. The body can comprise a handpiece.

9. Examples of Apparatus with Broadband Pressure Wave Generators

In one aspect, an apparatus for treating a tooth is disclosed. The apparatus comprises a pressure wave generator having at least a distal portion configured to be inserted into a tooth chamber in a tooth and submerged in fluid in the tooth chamber. The pressure wave generator may produce acoustic pressure waves having a broadband spectrum.

The distal portion of the pressure wave generator configured to be inserted into a tooth chamber can include the distal portion being sized or shaped to fit into the tooth chamber.

In other aspects, the broadband spectrum comprises power at least at frequencies above about 1 kHz, while in yet other aspects, the broadband spectrum may comprise power at least at frequencies above about 10 kHz. In some embodiments, the broadband spectrum may comprise power at least at frequencies above about 100 kHz or above about 500 kHz. The broadband spectrum may have a bandwidth greater than about 50 kHz. The broadband spectrum may have a bandwidth greater than about 100 kHz. Additionally, the broadband spectrum may have a bandwidth greater than about 500 kHz.

The pressure wave generator may comprise one or more devices selected from the group consisting of: a fluid jet, a laser, a mechanical stirrer, and an ultrasonic device. In some embodiments, the distal portion of the pressure wave generator may comprise an impingement surface, and the pressure wave generator may also comprise a liquid jet configured to impact the impingement surface. The apparatus may further comprise a source of degassed liquid configured to provide liquid for the liquid jet. The apparatus may also comprise a fluid retainer positioned around the pressure wave generator such that the fluid retainer substantially closes an access opening into the tooth chamber. The fluid retainer may be configured to substantially inhibit flow of air into the tooth chamber. In some aspects, the fluid retainer may comprise a sponge, and in other aspects, the fluid retainer may comprise a vent to regulate fluid pressure within the tooth chamber. In yet other embodiments, the fluid retainer may comprise a fluid outlet port for removal of fluid from the tooth chamber. The fluid outlet port may further comprise a vent in fluid communication with the fluid outlet port. In other aspects, the vent may be configured to permit air to be entrained into flow of fluid removed from the tooth chamber via the fluid outlet port, and the vent can be further configured to inhibit flow of air into the tooth chamber.

10. Examples of Apparatus with Pressure Wave Generators Generating Frequencies Above 1 kHz In another embodiment, an apparatus for treating a tooth is disclosed. The apparatus comprises a pressure wave generator having at least a distal portion configured to be inserted into a tooth chamber in a tooth and submerged in fluid in the tooth chamber. The pressure wave generator may produce acoustic pressure waves at least having frequencies of 1 kHz or greater. The distal portion of the pressure wave generator configured to be inserted into a tooth chamber can include the distal portion being sized or shaped to fit into the tooth chamber.

In some embodiments, the acoustic pressure waves may at least have frequencies of 10 kHz or greater, while in other embodiments, the acoustic pressure waves may at least have frequencies of 100 kHz or greater. In other embodiments, the acoustic pressure waves at least have frequencies of 10 kHz or greater. The acoustic pressure waves may have substantial power at frequencies greater than about 1 kHz, greater than about 10 kHz, greater than about 100 kHz, or greater than about 500 kHz. Substantial power can include, for example, an amount of power that is greater than 10%, greater than 25%, greater than 35%, or greater than 50% of the total acoustic power (e.g., the acoustic power integrated over all frequencies). In some aspects, the acoustic pressure waves have a bandwidth of at least about 10 kHz. In other aspects, the acoustic pressure waves have a bandwidth of at least about 50 kHz, while in some aspects, the acoustic pressure waves have a bandwidth of at least about 100 kHz. The pressure wave generator may comprise one or more devices selected from the group consisting of: a fluid jet, a laser, a mechanical stirrer, and an ultrasonic device. In some embodiments, the pressure wave generator comprises a liquid jet configured to impact an impingement surface of the distal portion of the pressure wave generator. The liquid jet may comprise a degassed liquid.

11. Examples of Procedures Using Pressure Wave Generators Having an Energy Outlet in a Fluid In another aspect, a procedure for treating a tooth is disclosed. The procedure comprises forming at least an access opening into a tooth chamber in a tooth, inserting fluid into at least a portion of the tooth chamber, and providing a pressure wave generator having an energy outlet disposed in the fluid during at least a portion of the procedure. The procedure may further comprise positioning the energy outlet such that pressure waves generated from the outlet are delivered to the fluid and into the tooth chamber through the fluid. Further, the procedure may comprise activating the pressure wave generator so as to produce acoustic pressure waves with at least a substantial amount of the produced acoustic pressure waves having frequencies of 1 kHz or greater. The procedure may further comprise using the pressure wave generator to deliver sufficient energy to the fluid so as to dissociate tissue in the tooth.

In some aspects, inserting fluid may comprise introducing a degassed liquid. Further, in some cases, at least a substantial amount of the produced acoustic pressure waves may have frequencies of 50 kHz or greater. Activating the pressure wave generator may comprise activating a fluid jet beam. The procedure may further comprise impacting an impingement surface with the fluid jet beam. In addition, activating the pressure wave generator may comprise activating a laser, and activating the pressure wave generator may also produce acoustic pressure waves that create at least some fluid cavitation in the tooth chamber.

12. Examples of Procedures Using Pressure Wave Generators and Limiting Apical Pressure In another aspect, a procedure for treating a tooth is disclosed. The procedure comprises forming at least an access opening into a tooth chamber in a tooth, inserting fluid into at least a portion of the tooth chamber, and providing a pressure wave generator having an energy outlet disposed in the fluid during at least a portion of the procedure. The procedure may further comprise positioning the energy outlet such that energy generated from the outlet is delivered to the fluid and into the chamber through the fluid, and such that the energy does not create an apical pressure above about 100 mmHg in a canal of the tooth. The procedure may further comprise activating the pressure wave generator, maintaining the energy outlet of the pressure wave generator in the fluid during at least part of the procedure, and using the pressure wave generator to delivery sufficient energy to the fluid so as to dissociate tissue in the tooth.

In some aspects, the procedure may comprise providing an impingement surface positioned near the energy outlet. Activating the pressure wave generator may comprise forming an energy beam and impacting the impingement surface with the energy beam. In some cases, the energy beam may comprise a fluid jet beam. In some embodiments, the procedure may further comprise deflecting the fluid jet beam from the impingement surface when the fluid jet beam impacts the impingement surface. In addition, the procedure may comprise positioning the energy outlet such that the deflected fluid jet beam passes through the energy outlet. In some aspects, forming the energy beam may comprise activating a laser, activating an ultrasonic device, or activating a mechanical stirrer. In some cases, the energy may not create a jet stream of fluid down a canal of the tooth.

13. Examples of Procedures Using Fluid Retainers

In yet another aspect, a procedure for treating a tooth is disclosed. The procedure comprises forming at least an access opening into a tooth chamber in a tooth, and applying a fluid retainer onto the tooth. The fluid retainer may comprise an inner chamber that communicates with the tooth chamber when the fluid retainer is applied to the tooth. The procedure may further comprise supplying fluid into at least a portion of the tooth chamber and into at least a portion of the inner chamber of the fluid retainer. Further, the procedure may comprise positioning a pressure wave generator in the inner chamber such that, during at least part of the procedure, an energy outlet of the pressure wave generator extends into the inner chamber and is disposed within the fluid. In addition, the procedure may comprise activating the pressure wave generator to produce acoustic energy waves in the fluid in the tooth chamber, and using the pressure wave generator to delivery sufficient energy to the fluid so as to dissociate tissue in the tooth.

In some aspects, supplying fluid may comprise supplying a degassed liquid. The procedure may further comprise using the fluid retainer to inhibit uncontrolled flow of fluid. In some cases, using the fluid retainer to inhibit uncontrolled flow of fluid may include retaining sufficient fluid within the tooth chamber to permit the acoustic energy waves to propagate within the fluid. In addition, the acoustic energy waves may retain sufficient energy to create at least some fluid cavitation within the tooth chamber. Using the fluid retainer may further comprise substantially inhibiting air flow into the tooth chamber.

In some embodiments, the procedure may comprise removing waste fluid from the tooth chamber. In some cases, using the fluid retainer may substantially inhibit leakage of supplied fluid, waste fluid, and organic material from the tooth chamber. Using the fluid retainer may comprise permitting at least some of the fluid to leave the tooth chamber while substantially inhibiting air from entering the chamber. In some aspects, using the fluid retainer involves positioning a cap around the tooth chamber such that the cap substantially closes the access opening into the tooth chamber. In other aspects, the procedure may comprise positioning the cap on a tooth seal region of the tooth. The tooth seal region may comprise a tooth seal, and positioning the cap on the tooth seal region may comprise planarizing a surface of the tooth seal.

Using the fluid retainer may involve positioning a flow restrictor around the tooth chamber and within the cap. Positioning the cap on the tooth seal region may also substantially seal the tooth chamber so as to allow for controlled ingress and egress of fluid. In some cases, using the fluid retainer may further comprise providing a vent to regulate fluid pressure within the tooth chamber. Additionally, providing the vent may include permitting at least some air flow to be entrained with fluid removed from the tooth chamber. In some embodiments, the procedure may also comprise providing a fluid outlet configured to permit fluid to flow from the tooth chamber. Using the fluid retainer may maintain the fluid pressure within the tooth at pressures below a predetermined pressure level. In some embodiments, activating the pressure wave generator may comprise activating a fluid jet or activating a laser. In some cases, activating the pressure wave generator may create at least some fluid cavitation in the tooth chamber.

14. Examples of Procedures Using Auxiliary Chambers

In another embodiment, a procedure for treating a tooth is disclosed. The procedure comprises forming at least an access opening into a tooth chamber in the tooth, and providing an auxiliary chamber disposed adjacent the tooth. The auxiliary chamber may comprise an inner or interior chamber of a fluid retainer. The procedure may further comprise providing a fluid filling at least a portion of the tooth chamber and at least a portion of the auxiliary chamber. The fluid may provide a common energy transmission medium between the tooth chamber and the auxiliary chamber. The procedure may also comprise inserting an energy outlet of a pressure wave generator into the auxiliary chamber so as to extend into and be immersed in the fluid within the auxiliary chamber. Further, the procedure may comprise activating the pressure wave generator to produce acoustic energy waves in the fluid in the tooth chamber, and using the pressure wave generator to delivery sufficient energy to the fluid in the tooth chamber so as to dissociate tissue in the tooth.

In some embodiments, providing an auxiliary chamber may comprise positioning a fluid retainer around the access opening of the tooth chamber. Positioning the fluid retainer may further comprise positioning a cap around the access opening such that the cap substantially closes the access opening into the tooth chamber. In some aspects, the procedure may comprise positioning the cap on a tooth seal region of the tooth. In some cases, the tooth seal region may comprise a tooth seal. Further, positioning the fluid retainer may involve positioning a flow restrictor around the access opening and within the cap. In some embodiments, positioning the cap on the tooth seal region substantially seals the tooth chamber and the auxiliary chamber so as to allow for controlled ingress and egress of fluid.

The procedure may further comprise providing a vent to regulate fluid pressure within the tooth chamber. In some aspects, providing the vent includes permitting at least some air flow to be entrained with fluid removed from the tooth chamber. Additionally, the procedure may comprise providing a fluid outlet configured to permit fluid to flow from the tooth chamber. Activating the pressure wave generator may comprise activating a fluid jet or activating a laser. In some cases, activating the pressure wave generator creates at least some fluid cavitation in the tooth chamber.

15. Examples of Apparatus with Fluid Retainers Having an Inner Chamber

In another aspect, an apparatus for treating a tooth is disclosed. The apparatus comprises a fluid retainer configured to be applied to the tooth to substantially retain fluid in a tooth chamber in the tooth. The fluid retainer may include an inner chamber. The apparatus may also comprise a pressure wave generator having an energy outlet disposed within the inner chamber of the fluid retainer. In some cases, when the fluid retainer is applied to the tooth, the inner chamber may be disposed so as to be in communication with the tooth chamber, and the energy outlet of the pressure wave generator may be disposed outside the tooth chamber.

In some aspects, the apparatus may comprise a body that includes the fluid retainer and one or more vents configured to permit at least some of the fluid to leave the tooth chamber while inhibiting air from entering the tooth chamber. The body may comprise an outer housing substantially surrounding the fluid retainer. In some aspects, the fluid retainer comprises one or more vents configured to permit at least some of the fluid to leave the tooth chamber while inhibiting air from entering the tooth chamber. The one or more vents may be configured to permit at least some air flow to be entrained with fluid leaving the tooth chamber. In some embodiments, the body may comprise a fluid outlet configured to permit fluid to flow from the tooth chamber. The body may also comprise a handpiece. In some cases, the pressure wave generator may be configured to generate acoustic energy waves. Further, the fluid retainer may be configured to retain sufficient fluid within the tooth chamber to permit acoustic energy waves to propagate within the fluid. A substantial amount of the acoustic energy waves generated by the pressure wave generator may also retain sufficient energy to create at least some fluid cavitation within the tooth chamber.

In some embodiments, the fluid retainer may comprise a flow restrictor. The flow restrictor may comprise a sponge or a vent. Additionally, the fluid retainer may be configured to substantially inhibit air flow into the tooth chamber. The fluid retainer may also include at least one outlet. In some embodiments, the fluid retainer may be configured to substantially inhibit leakage of fluid, organic material, or both from the tooth chamber. In yet other aspects, the fluid retainer may be configured to permit at least some of the fluid to leave the tooth chamber. The fluid retainer may also be configured to substantially inhibit air from entering the chamber.

The fluid retainer may comprise a cap. In some aspects, the cap may be configured to be positioned around the tooth chamber such that the cap substantially closes an access opening into the tooth chamber. Further, the cap may be configured to be positioned on a tooth seal region of the tooth, and the cap may also include a planar surface that mates to a tooth seal having a planar surface. In some embodiments, the fluid retainer may comprise a flow restrictor configured to be positioned around the tooth chamber and within the cap. The cap may also substantially seal the tooth chamber so as to allow for controlled ingress and egress of fluid. The fluid retainer may be configured to maintain the fluid pressure within the tooth at pressures below a predetermined pressure level. In addition, the pressure wave generator may comprise one or more devices selected from the group consisting of: a fluid jet, a laser, a mechanical stirrer, and an ultrasonic device. Further, the pressure wave generator may be configured to produce acoustic energy waves capable of creating at least some fluid cavitation in the tooth chamber.

16. Examples of Apparatus with Pressure Wave Generators Generating Frequencies Above 1 kHz In another aspect, an apparatus for treating a tooth is disclosed. The apparatus comprises a body having a fluid chamber with an opening to communicate with a tooth chamber in a tooth when the body is disposed adjacent a tooth. The apparatus may further comprise a pressure wave generator having an energy outlet disposed within the fluid chamber. The pressure wave generator may be configured to produce acoustic pressure waves. At least a substantial amount of the produced acoustic pressure waves can have frequencies of 1 kHz or greater.

In certain embodiments, the energy outlet can comprise a point or a set of points in the pressure wave generator that transmit energy into the ambient medium (e.g., fluid in the tooth chamber). For example, the energy outlet for some liquid jet devices may comprise a distal end of a guide tube having an impingement or reverberation surface. The jet may impact the impingement or reverberation surface and form a spray that leaves the guide tube through one or more windows to interact with fluid in the tooth chamber. As another example, an energy outlet for an electromagnetic laser device may comprise a tapered tip of an optical fiber.

In other aspects, a substantial amount of the produced acoustic pressure waves may have frequencies of 10 kHz or greater, or 100 kHz or greater. The acoustic pressure waves may have substantial power at frequencies greater than about 1 kHz, greater than about 10 kHz, greater than about 100 kHz, or greater than about 500 kHz. Substantial power can include, for example, an amount of power that is greater than 10%, greater than 25%, greater than 35%, or greater than 50% of the total acoustic power (e.g., the acoustic power integrated over all frequencies). The produced acoustic pressure waves may also have a bandwidth of at least about 10 kHz, at least about 50 kHz, or at least about 100 kHz.

In some embodiments, the pressure wave generator may comprise one or more devices selected from the group consisting of: a fluid jet, a laser, a mechanical stirrer, and an ultrasonic device. The pressure wave generator may also comprise a liquid jet. Additionally, the energy outlet may comprise a reverberation surface, and the liquid jet may be configured to impact a portion of the reverberation surface. The apparatus may further comprise a source of degassed liquid configured to provide liquid for a liquid jet. In some cases, the body may be configured to substantially close an access opening into the tooth chamber, and the body may further comprise a vent to regulate fluid pressure within the tooth chamber. The body can substantially close the access opening to retain most or substantially all of the fluid in the tooth chamber by providing a water-resistant seal between the retainer and the tooth. The body may, but need not, retain all the fluid in the tooth chamber. For example substantially retaining fluid in the tooth chamber does not require that there be no amount of leakage of the fluid from the tooth chamber. The body can be applied to the tooth to reduce or minimize the amount of fluid that leaks into the patient's mouth during treatment, which may improve patient safety and experience since some fluids can contain caustic or unpleasant tasting substances.

In yet other aspects, the body may comprise a fluid outlet port for removal of fluid from the tooth chamber, and the body may further comprise a vent in fluid communication with the fluid outlet port. In some cases, the vent may be configured to permit air to be entrained into flow of fluid removed from the tooth chamber via the fluid outlet port, and the vent may further be configured to inhibit flow of air into the tooth chamber.

17. Examples of Procedures for Treating a Tooth Using Vented Ports

In another aspect, a procedure for treating a tooth is disclosed. The procedure comprises forming at least an access opening into a tooth chamber in a tooth, closing the tooth chamber using a fluid retainer applied to the tooth, and introducing fluid through an ingress port into at least a portion of the tooth chamber. The procedure may further comprise removing fluid from the tooth chamber through an egress port, and venting fluid from the tooth chamber through a vent port when fluid pressure within the tooth chamber generally exceeds a predefined pressure level. Further, the procedure may comprise inhibiting air flow into the tooth chamber through the vent port.

In some aspects, venting fluid from the tooth chamber may further comprise permitting at least some air flow to be entrained with fluid removed from the tooth chamber. In some cases, introducing fluid may comprise introducing a degassed liquid. The procedure may further comprise inserting a pressure wave generator into the tooth chamber and at least partially below a fluid level of the introduced fluid. The procedure may also comprise activating the pressure wave generator in the tooth chamber to produce acoustic energy waves in the fluid. In some cases, the acoustic energy waves may retain sufficient energy to create at least some fluid cavitation within the tooth chamber. In some embodiments, the procedure may comprise using the fluid retainer to inhibit uncontrolled flow of fluid. Further, using the fluid retainer to inhibit uncontrolled flow may include retaining sufficient fluid within the tooth chamber to permit the acoustic energy waves to propagate within the fluid.

In some aspects, using the fluid retainer may involve positioning a cap around the tooth chamber such that the cap substantially closes the access opening into the tooth chamber. The procedure may also comprise positioning the cap on a tooth seal region of the tooth. In some cases, the tooth seal region may comprise a tooth seal. In addition, positioning the cap on the tooth seal region may comprise planarizing a surface of the tooth seal. In some embodiments, using the fluid retainer may involve positioning a flow restrictor around the tooth chamber and within the cap. Additionally, positioning the cap on the tooth seal region may substantially seal the tooth chamber so as to allow for controlled ingress and egress of fluid.

18. Examples of Apparatus for Treating a Tooth Using Vented Ports

In another embodiment, an apparatus for treating a tooth comprises a fluid retainer configured to be applied to the tooth to substantially retain fluid in a tooth chamber in the tooth. A suction port on the fluid retainer may be configured to remove fluid from the tooth chamber. The apparatus may further comprise a vent in fluid communication with the suction port. The vent may be configured to permit air to be entrained into the flow of fluid removed from the tooth chamber via the suction port. In addition, the vent may further be configured to inhibit flow of air into the chamber in the tooth.

In some aspects, the apparatus may comprise an inlet port configured to deliver fluid into the tooth chamber. In some cases, the vent may comprise an elongated shape with a ratio of length to width greater than about 1.5 to 1. The vent may also be configured such that pressure of the fluid at an apex of the tooth (or in the tooth chamber) is less than about 100 mmHg. In some embodiments, the vent may further be configured to allow degassed fluid to exit the tooth chamber. The vent may comprise a plurality of vents. In some aspects, the apparatus may further comprise a housing in fluid connection with the suction port.

The apparatus may comprise a pressure wave generator having a distal portion. The distal portion of the pressure wave generator may be configured to be inserted through the fluid retainer into the tooth chamber. In some cases, the pressure wave generator may comprise one or more devices selected from the group consisting of: a fluid jet, a laser, a mechanical stirrer, and an ultrasonic device. The pressure wave generator may also be configured to generate acoustic energy waves. In some embodiments, the fluid retainer may be configured to retain sufficient fluid within the tooth chamber to permit acoustic energy waves to propagate within the fluid. Additionally, a substantial amount of the acoustic energy waves generated by the pressure wave generator may retain sufficient energy to create at least some fluid cavitation within the tooth chamber.

In some aspects, the fluid retainer may comprise a flow restrictor. In some embodiments, the flow restrictor may comprise a sponge or a vent. The fluid retainer may also be configured to substantially inhibit leakage of fluid, organic material, or both from the tooth chamber. In some aspects, the fluid retainer may comprise a cap. The cap may be configured to be positioned around the tooth chamber such that the cap substantially closes an access opening into the tooth chamber. Further, the cap may be configured to be positioned on a tooth seal region of the tooth, and the cap may include a planar surface that mates to a tooth seal having a planar surface. In some cases, the pressure wave generator may be configured to create at least some fluid cavitation in the tooth chamber. Also, in some embodiments, the fluid retainer may be in fluid connection with a distal portion of a housing. In some aspects, the fluid retainer may comprise a flow restrictor configured to be positioned around the tooth chamber and within the cap. The cap may also substantially seal the tooth chamber so as to allow for controlled ingress and egress of fluid.

19. Examples of Methods of Cleaning a Tooth Using Degassed Fluids

In another embodiment, a method of treating a tooth comprises forming at least an access opening into a tooth chamber in a tooth, introducing degassed liquid from a source of degassed liquid into the tooth chamber, and cleaning organic material from dentin in the tooth using the degassed liquid.

In other embodiments, the method may further comprise providing the degassed liquid from a reservoir of degassed liquid. The method may also comprise providing the degassed liquid from a degassing system. The degassed liquid may have an amount of dissolved gases less than 18 mg/L, less than 12 mg/L, less than 6 mg/L, or less than 3 mg/L. In some aspects, introducing the degassed liquid may comprise irrigating the tooth chamber with the degassed liquid. In yet other aspects, introducing the degassed liquid may comprise propagating a high velocity liquid beam into the tooth chamber, and the liquid beam may in some cases comprise the degassed liquid. In some embodiments, cleaning the organic material may comprise generating pressure waves using the high velocity liquid beam. Introducing the degassed liquid may also comprise circulating the degassed liquid in the tooth chamber. The method may further comprise cleaning inorganic material from dentin in the tooth using the degassed liquid. The degassed liquid may include a tissue dissolving agent. The degassed liquid may include a decalcifying agent.

20. Examples of Methods of Generating Acoustic Waves in Degassed Fluids

In another aspect, a method for treating a tooth comprises flowing a degassed fluid into a tooth chamber in a tooth, and generating acoustic waves in the degassed fluid in the tooth.

In some cases, flowing the degassed liquid may comprise propagating a high velocity liquid beam into the tooth chamber, and the liquid beam may further comprise the degassed liquid. Generating acoustic waves may comprise generating acoustic waves using the high velocity liquid beam. In addition, flowing the degassed liquid may comprise circulating the degassed liquid in the tooth chamber. The method may further comprise generating acoustic cavitation using the acoustic waves. The method may comprise providing the degassed liquid from a reservoir of degassed liquid, and the method may further comprise providing the degassed liquid from a degassing system. In some cases, the degassed liquid may have an amount of dissolved gases less than 18 mg/L, less than 12 mg/L, less than 6 mg/L, or less than 3 mg/L. Further, the method may comprise cleaning organic or inorganic matter from the tooth chamber. For example, the acoustic waves may provide the cleaning, or the acoustic waves may induce cavitation effects that provide the cleaning.

21. Examples of Methods of Generating Liquid Beams Using Degassed Fluids

In another embodiment, a method of treating a tooth comprises providing a source of degassed liquid, and generating a collimated beam of degassed liquid from the source of degassed liquid. The method may further comprise using the collimated beam of degassed liquid to produce an acoustic wave within a tooth chamber in the tooth, and dissociating organic material within the tooth chamber using the acoustic wave.

In some aspects, generating the collimated beam of degassed liquid may comprise passing the degassed liquid through an orifice. For example, the orifice may include an opening in a nozzle of a liquid jet device wherein high-pressure liquid passes through the opening in the form of a high-velocity beam. In some cases, using the collimated beam of degassed liquid to produce the acoustic wave may comprise generating acoustic power at least having substantial power at frequencies greater than about 1 kHz, greater than about 10 kHz, or greater than about 100 kHz. Substantial power can include, for example, an amount of power that is greater than 10%, greater than 25%, greater than 35%, or greater than 50% of the total acoustic power (e.g., the acoustic power integrated over all frequencies). Further, using the collimated beam of degassed liquid to produce the acoustic wave may comprise generating acoustic cavitation in the tooth chamber. The method may further comprise propagating the acoustic wave through fluid in the tooth chamber. In some cases, the degassed liquid may have an amount of dissolved gases less than 18 mg/L, less than 12 mg/L, less than 6 mg/L, or less than 3 mg/L.

22. Examples of Methods of Propagating Acoustic Pressure Waves in Degassed Fluids In yet another embodiment, a method for treating a tooth comprises introducing a degassed liquid into a tooth chamber in a tooth, and producing acoustic pressure waves in the degassed liquid. The method may further comprise propagating the acoustic pressure waves through the degassed liquid to surrounding dentin structure of the tooth. In some cases, the degassed liquid may have an amount of dissolved gases less than 18 mg/L, less than 12 mg/L, less than 6 mg/L, or less than 3 mg/L.

In some embodiments, introducing the degassed liquid may comprise propagating a high velocity liquid beam into the tooth chamber. The liquid beam may comprise the degassed liquid. Further, introducing the degassed liquid may comprise circulating the degassed liquid in the tooth chamber. The method may further comprise cleaning organic or inorganic material from the dentin structure of the tooth. In some cases, the method may comprise generating acoustic cavitation using the propagated acoustic pressure waves.

23. Examples of Methods of Inhibiting Gas Bubble Formation in Degassed Fluids

In another aspect, a method for treating a tooth comprises introducing a degassed liquid into a tooth chamber in a tooth. The method may further comprise delivering energy into the degassed liquid to clean organic or inorganic material from the dentin of the tooth, whereby the degassed liquid inhibits formation of gas bubbles in the tooth chamber.

In some aspects, the degassed liquid may have a dissolved gas content less than about 18 mg/L, less than about 12 mg/L, less than 6 mg/L, or less than 3 mg/L. In some cases, delivering energy may comprise delivering electromagnetic energy. In yet other cases, delivering energy may comprise delivering acoustic energy. The energy may be delivered using a laser or a high-velocity liquid jet. Further, delivering energy may also comprise generating pressure waves using the delivered energy.

24. Examples of Methods of Penetrating Small Openings in a Tooth Using Degassed Fluids In another embodiment, a method for treating a tooth comprises introducing a degassed liquid into a tooth chamber in a tooth, and promoting circulation of the degassed liquid within the tooth chamber. The degassed liquid may have a sufficiently low amount of dissolved gasses so as to penetrate openings in the tooth chamber having a dimension less than 500 microns.

In some embodiments, introducing the degassed liquid may comprise irrigating the tooth chamber with the degassed liquid. In other cases, introducing the degassed liquid may comprise propagating a high velocity liquid beam into the tooth chamber. The liquid beam may comprise the degassed liquid. Promoting circulation may comprise substantially inhibiting flow of the degassed liquid out of the tooth chamber. In some cases, promoting circulation may comprise regulating a fluid pressure in the tooth chamber. The amount of dissolved gasses may be less than 18 mg/L, less than 12 mg/L, less than 6 mg/L, or less than 3 mg/L. Further, the amount of dissolved gasses may be sufficiently low so that the degassed liquid can penetrate openings in the tooth chamber having a dimension less than 250 microns, less than 100 microns, less than 50 microns, less than 25 microns, less than 10 microns, less than 5 microns, less than 3 microns, less than 2 microns, or less than 1 micron in various embodiments. The method may further comprise propagating acoustic energy through the degassed fluid into the openings in the tooth chamber. In some cases, the method may further comprise cleaning the openings in the tooth chamber using the acoustic energy.

25. Examples of Apparatus Comprising a Degassed Liquid Source

In yet other aspects, an apparatus for treating a tooth is disclosed. The apparatus comprises a degassed liquid source, and a fluid retainer configured to be applied to a tooth. The fluid retainer may include a fluid inlet communicating with the degassed liquid source so as to deliver degassed fluid into a tooth chamber in the tooth.

In some aspects, the degassed liquid source may be configured to deliver degassed fluid to clear organic material from the tooth. In some cases, the degassed fluid may be free of dissolved gases to less than 0.1% by volume or less than 18 mg/L. In additional embodiments, the degassed fluid may have a percentage of dissolved oxygen less than about 7 mg/L. Further, the fluid retainer may be configured to substantially retain degassed fluid in the tooth chamber. The fluid retainer may also be configured to substantially inhibit air flow into the tooth chamber. In some aspects, the fluid retainer may include at least one fluid outlet. The fluid retainer may also be configured to substantially inhibit leakage of degassed fluid, organic material, or both from the tooth chamber.

In some instances, the fluid retainer may comprise a cap. The cap may be configured to be positioned around the tooth chamber such that the cap substantially closes an access opening into the tooth chamber. The cap may be configured to be positioned on a tooth seal region of the tooth. In some embodiments, the cap may include a planar surface that mates to a tooth seal having a planar surface. In some aspects, the apparatus may also comprise a pressure wave generator having an energy outlet disposed within the tooth chamber. The pressure wave generator may be configured to create at least some fluid cavitation in the tooth chamber. In some cases, the fluid retainer may comprise a flow restrictor configured to be positioned around the tooth chamber and within the cap. The cap may also substantially seal the tooth chamber so as to allow for controlled ingress and egress of degassed fluid.

In addition, the fluid retainer may comprise one or more vents configured to permit at least some of the degassed fluid to leave the tooth chamber while inhibiting air from entering the tooth chamber. In some embodiments, the one or more vents may be configured to permit at least some air flow to be entrained with degassed fluid leaving the tooth chamber. Further, the fluid retainer may comprise a fluid outlet configured to permit fluid to flow from the tooth chamber.

In some embodiments, the apparatus may comprise a pressure wave generator having an energy outlet disposed within the tooth chamber. The pressure wave generator may be configured to create at least some fluid cavitation in the tooth chamber. The apparatus may further comprise a pressure wave generator having an energy outlet disposed within the tooth chamber. In some aspects, the fluid retainer may be configured to maintain the fluid pressure within the tooth at pressures below a predetermined pressure level. In some instances, the pressure wave generator may comprise one or more devices selected from the group consisting of: a fluid jet, a laser, a mechanical stirrer, and an ultrasonic device. The pressure wave generator may also be configured to create at least some fluid cavitation in the tooth chamber.

26. Examples of Apparatus Comprising a Fluid Introducer

In another aspect, an apparatus for treating a tooth comprises a degassed liquid source. The apparatus may further include a fluid introducer configured to supply degassed fluid from the degassed liquid source to a tooth chamber in a tooth. The fluid introducer may comprise a fluid inlet. The fluid inlet may have a distal end sized or shaped to fit in the tooth chamber.

In other aspects, the degassed liquid source may be configured to deliver degassed fluid to clear organic material from the tooth. In some cases, the degassed fluid may be free of dissolved gases to less than 0.1% by volume or less than 18 mg/L. In other embodiments, the degassed fluid may have a percentage of dissolved oxygen less than about 7 mg/L. The fluid introducer may be configured to circulate the degassed fluid within the tooth chamber. In some cases, the degassed liquid source may comprise a reservoir. A distal portion of the fluid introducer may be configured to be positioned within the tooth chamber.

In some embodiments, the fluid introducer may comprise a channel configured to permit the degassed fluid to flow therethrough. The degassed fluid may comprise a high-velocity fluid jet beam. The channel may be configured to direct the fluid jet beam to impact an impingement member positioned near a distal portion of the channel. The channel may have an opening at the distal portion of the channel, and the opening may be configured to allow the fluid jet beam to exit the channel when it impacts the impingement member. The apparatus may further comprise a fluid retainer configured to substantially retain at least some of the fluid in the tooth chamber.

The fluid retainer may also be configured to substantially inhibit air flow into the tooth chamber. In some aspects, the fluid retainer may comprise one or more vents configured to permit at least some of the degassed fluid to leave the tooth chamber while inhibiting air from entering the tooth chamber. In addition, the one or more vents may be configured to permit at least some air flow to be entrained with degassed fluid leaving the tooth chamber. In some embodiments, the fluid retainer may further comprise a fluid outlet configured to permit fluid to flow from the tooth chamber.

In further embodiments, the apparatus may comprise a pressure wave generator having an energy outlet disposed within the tooth chamber. The pressure wave generator may be configured to create at least some fluid cavitation in the tooth chamber. In some cases, the pressure wave generator may comprise one or more devices selected from the group consisting of: a fluid jet, a laser, a mechanical stirrer, and an ultrasonic device.

27. Examples of Apparatus Comprising a Degassed Fluid and a Pressure Wave Generator In another embodiment, an apparatus for treating a tooth comprises a degassed liquid source for providing degassed liquid, and a fluid inlet configured to deliver degassed liquid from the degassed liquid source into a tooth chamber in the tooth. The apparatus may further comprise a pressure wave generator being configured to generate pressure waves in the degassed liquid in the tooth chamber.

In some embodiments, the pressure wave generator may include an energy outlet disposed within the tooth chamber. The pressure wave generator may also be configured to create at least some fluid cavitation in the tooth chamber. In some cases, the pressure wave generator may comprise one or more devices selected from the group consisting of: a fluid jet, a laser, a mechanical stirrer, and an ultrasonic device. The degassed liquid may be free of dissolved gases to less than 0.1% by volume or less than 18 mg/L. In addition, the degassed liquid may have a percentage of dissolved oxygen less than about 7 mg/L. In some aspects, the apparatus may comprise a fluid retainer configured to substantially retain at least some of the degassed liquid in the tooth chamber. The fluid retainer may also be configured to substantially inhibit air flow into the tooth chamber.

28. Examples of Degassed Fluids Comprising a Tissue Dissolving Agent

In some aspects, a fluid for treating a tooth comprises a tissue dissolving agent. The fluid can have an amount of dissolved gas less than 18 mg/L. The fluid can have an amount of dissolved gas less than 12 mg/L. The fluid can have an amount of dissolved gas less than 6 mg/L. The fluid can have an amount of dissolved gas less than 3 mg/L. The fluid can have an amount of dissolved gas less than 1 mg/L. The gas can comprise air (e.g., primarily nitrogen and oxygen). In some cases, the gas comprises oxygen, and the amount of dissolved oxygen is less than 7 mg/L or less than 3 mg/L.

The tissue dissolving agent can have a concentration less than 6% by volume, or less than 3% by volume, or less than 1% by volume. The tissue dissolving agent can comprise sodium hypochlorite. The fluid can comprise water or saline. The saline can be isotonic, hypotonic, or hypertonic.

The fluid can further comprise nanoparticles, biologically-active particles, or a chemical agent comprising hydroxyl functional groups. The fluid can further comprise a decalcifying agent. The decalcifying agent can comprise ethylenediaminetetraacetic acid (EDTA).

In other aspects, use of a fluid comprising a tissue dissolving agent with the fluid having an amount of dissolved gas less than 18 mg/L for treating a tooth is described. Treating a tooth can comprise at least one of irrigating a tooth, cleaning a tooth, generating acoustic waves in the fluid, producing a collimated beam of the fluid, propagating acoustic waves through the fluid, inhibiting formation of gas bubbles in the tooth chamber, or promoting circulation of the fluid in the tooth chamber.

29. Examples of Degassed Fluids Comprising a Decalcifying Agent

In some aspects, a fluid for treating a tooth comprises a decalcifying agent. The fluid can have an amount of dissolved gas less than 18 mg/L. The fluid can have an amount of dissolved gas less than 12 mg/L. The fluid can have an amount of dissolved gas less than 6 mg/L. The fluid can have an amount of dissolved gas less than 3 mg/L. The fluid can have an amount of dissolved gas less than 1 mg/L. The gas can comprise air (e.g., primarily nitrogen and oxygen). In some cases, the gas comprises oxygen, and the amount of dissolved oxygen is less than 7 mg/L or less than 3 mg/L.

The decalcifying agent can have a concentration less than 6% by volume, or less than 3% by volume, or less than 1% by volume. The decalcifying agent can comprise ethylenediaminetetraacetic acid (EDTA). The fluid can comprise water or saline. The saline can be isotonic, hypotonic, or hypertonic.

The fluid can further comprise nanoparticles, biologically-active particles, or a chemical agent comprising hydroxyl functional groups. The fluid can further comprise a tissue dissolving agent. The tissue dissolving agent can comprise sodium hypochlorite (NaOCl).

In other aspects, use of a fluid comprising a decalcifying agent with the fluid having an amount of dissolved gas less than 18 mg/L for treating a tooth is described. Treating a tooth can comprise at least one of irrigating a tooth, cleaning a tooth, generating acoustic waves in the fluid, producing a collimated beam of the fluid, propagating acoustic waves through the fluid, inhibiting formation of gas bubbles in the tooth chamber, or promoting circulation of the fluid in the tooth chamber.

30. Examples of Procedures for Maintaining Fluid in a Tooth Chamber

In another aspect, a procedure for maintaining fluid in a tooth chamber in a tooth comprises delivering a fluid into the tooth chamber in the tooth and permitting at least some of the fluid to leave the tooth chamber while inhibiting air from entering the chamber.

In some aspects, delivering the fluid may comprise delivering a degassed fluid. Delivering the fluid may comprise positioning a fluid inlet within the tooth chamber. In addition, positioning the fluid inlet may comprise positioning a tube, and the fluid may flow through the tube. In some embodiments, the procedure may also comprise activating a pressure wave generator that produces acoustic energy waves within the tooth chamber. The procedure may further comprise providing a fluid retainer that retains sufficient fluid within the tooth chamber such that the acoustic energy waves have sufficient energy to create at least some fluid cavitation within the tooth chamber. In some cases, activating the pressure wave generator may comprise activating a fluid jet beam.

In some aspects, permitting at least some of the fluid to leave the chamber may comprise providing one or more vents to regulate fluid pressure within the tooth chamber. Providing one or more vents may comprise permitting at least some air flow to be entrained with fluid removed from the tooth chamber. In some embodiments, the procedure may comprise providing a fluid outlet configured to permit fluid to flow from the tooth chamber. Also, the procedure may comprise activating a pressure wave generator that produces acoustic energy waves within the tooth chamber. In some aspects, the procedure may further comprise providing a fluid retainer that retains sufficient fluid within the tooth chamber such that the acoustic energy waves have sufficient energy to create at least some fluid cavitation within the tooth chamber.

31. Examples of Apparatus for Maintaining Fluid in a Tooth Chamber

In another aspect, an apparatus for maintaining fluid in a tooth chamber in a tooth comprises a fluid retainer configured to be applied to the tooth to substantially retain fluid in the tooth chamber. The fluid retainer may include including one or more vents configured to permit at least some of the fluid to leave the tooth chamber while inhibiting air from entering the tooth chamber. The apparatus may further comprise a fluid inlet configured to deliver fluid into the tooth chamber.

In some aspects, a portion of the fluid inlet may further comprise a pressure wave generator. The pressure wave generator may be configured to produce acoustic energy waves. The acoustic energy waves may retain sufficient energy to create at least some fluid cavitation within the tooth chamber. In some embodiments, the fluid may comprise a degassed fluid. Additionally, the fluid inlet may comprise a channel configured to permit the fluid to flow therethrough.

In some aspects, the apparatus may comprise a fluid outlet configured to permit the fluid to flow from the chamber. In some cases, the channel may be configured to be positioned within the tooth chamber. Additionally, the fluid outlet may be configured to provide suction. In some embodiments, the fluid may comprise a fluid jet beam. The fluid inlet may also comprise an impingement surface positioned near a distal portion of the channel. Further, the channel may be configured to direct the fluid jet beam to impact the impingement surface. In some aspects, the channel may be configured to direct the fluid jet beam such that when the fluid jet beam impacts the impingement surface, an acoustic energy wave is produced. Also, the fluid retainer may be configured to retain sufficient fluid in the tooth chamber such that the acoustic energy waves can propagate with sufficient energy to cause at least some fluid cavitation within the tooth chamber.

32. Examples of Methods for Monitoring a Tooth

In another aspect, a method for monitoring fluid from a tooth comprises delivering a fluid to a tooth chamber in a tooth, removing fluid from the tooth chamber, and electronically monitoring a property of the fluid removed from the tooth chamber. The fluid can be delivered or removed using a fluid platform. The fluid can be delivered by a fluid inlet (or fluid introducer) or removed by a fluid outlet. A monitoring sensor (e.g., optical, electrical, or electrochemical) can be used to perform the electronic monitoring.

In other aspects, the method can further comprise activating or deactivating a pressure wave generator based at least in part upon the monitored property. The method can further comprise activating or deactivating a source that delivers the fluid into the tooth chamber. The activating or deactivating can be based at least in part upon the monitored property. Monitoring the property can comprise optical monitoring, and the property can comprise a reflectivity or a transmittivity of the fluid removed from the tooth chamber. Monitoring the property can comprise electrical or electrochemical monitoring.

In other aspects, the method can further comprise communicating information related to or derived from the monitored property to a user interface. The user interface can include a display (e.g., an LCD), a web browser, a mobile phone, a portable computer or tablet, etc.

The method can further comprise automatically adjusting a tooth irrigation or cleaning device based at least in part on the monitored property. The method can further comprise electronically monitoring a property of the fluid delivered to the tooth chamber. The method can further comprise automatically taking an action based at least in part on the monitored property of the fluid delivered to the tooth chamber and the monitored property of the fluid removed from the tooth chamber. The action can comprise one or more of: adjusting an endodontic apparatus, outputting information via a user interface, or providing an alert.

33. Examples of Apparatus for Monitoring a Tooth

In another aspect, an apparatus for monitoring fluid from a tooth comprises a fluid inlet (or a fluid introducer) configured to deliver fluid to a tooth chamber in a tooth, a fluid outlet configured to remove fluid from the tooth chamber, and a monitoring system configured to monitor a property of the fluid removed from the tooth chamber. For example, the fluid inlet or fluid outlet may be in fluid communication with the tooth chamber via a fluid platform.

The monitoring system can comprise an optical sensor. The optical sensor can be configured to measure a reflectivity or a transmittivity of the fluid removed from the tooth chamber. The monitoring system can comprise an electrical sensor or an electrochemical sensor.

The apparatus can further comprise an endodontic device, and the apparatus can be configured to adjust the endodontic device based at least in part on the monitored property of the fluid removed from the tooth chamber. The endodontic device can comprise one or more devices selected from the group consisting of: an irrigation device, a fluid delivery device, a fluid removal device, a tooth cleaning device, and a fluid platform. The tooth cleaning device can comprise a liquid jet device, a laser, an ultrasonic device, or a mechanical stirrer.

The monitoring system can be further configured to monitor a property of the fluid delivered to the tooth. The apparatus can further comprise an interface system configured to output information related to or derived from the monitored property. The apparatus can further comprise a pressure wave generator, and the monitoring system can be configured to activate or deactivate the pressure wave generator based at least in part on the monitored property.

34. Examples of Apparatus for Cleaning a Tooth

In one aspect, an apparatus for cleaning a tooth comprises a fluid retainer configured to be applied to the tooth to substantially retain fluid in a tooth chamber of the tooth and a pressure wave generator having a distal portion configured to be inserted into the tooth chamber. The apparatus may also comprise a vent configured to regulate pressure in the tooth chamber.

In various embodiments, the fluid retainer can be configured to enable circulation of the fluid within the tooth chamber. The fluid retainer can be configured to retain sufficient fluid in the tooth chamber such that the distal portion of the pressure wave generator remains submerged in the fluid. The fluid retainer can comprise a fluid inlet configured to deliver fluid to the tooth chamber. The apparatus can further comprise a source of fluid. The source of fluid can be configured to be in fluid communication with the fluid inlet. The source of fluid can comprise degassed fluid. The source of fluid can comprise a fluid comprising a tissue dissolving agent or a decalcifying agent.

The fluid retainer can comprise a fluid outlet configured to remove fluid from the tooth chamber. The vent can be in fluid communication with the fluid outlet. The vent can be configured to permit fluid from the tooth chamber to flow out of the vent when the pressure in the tooth chamber exceeds a pressure threshold. The vent can be configured to substantially inhibit air from flowing into the tooth chamber. The vent can be configured to allow ambient air to be entrained with fluid in the fluid outlet.

The apparatus can further comprise a monitoring sensor configured to monitor a property of fluid in the fluid outlet. The apparatus can be configured to activate or deactivate the pressure wave sensor in response to a monitored property of the fluid in the fluid outlet. The monitoring sensor can comprise an optical sensor, an electrical sensor, or an electrochemical sensor.

The pressure wave generator can comprises a liquid jet, a laser, an ultrasonic device, a mechanical stirrer, or a combination thereof. The pressure wave generator can be configured to generate an acoustic wave in the fluid retained in the tooth. The acoustic wave can have broadband power with a bandwidth greater than 10 kHz.

V. CONCLUSION

Although the tooth 10 schematically depicted in some of the figures is a molar, the procedures may be performed on any type of tooth such as an incisor, a canine, a bicuspid, a pre-molar, or a molar. Further, although the tooth may be depicted as a lower (mandibular) tooth in the figures, this is for purposes of illustration, and is not limiting. The systems, methods, and compositions may be applied to lower (mandibular) teeth or upper (maxillary) teeth. Also, the disclosed apparatus and methods are capable of treating root canal spaces having a wide range of morphologies, including highly curved root canal spaces. Moreover, the disclosed apparatus, methods, and compositions may be applied to human teeth (including juvenile teeth) and/or to animal teeth.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner (including differently than shown or described) in other embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and subcombinations are intended to fall within the scope of this disclosure.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

What is claimed is:

1. An apparatus for treating a tooth, the apparatus comprising:
   a fluid retainer configured to be applied to the tooth to substantially retain fluid in a tooth chamber in the tooth, the fluid retainer comprising an internal chamber;
   an inlet opening to supply fluid to the internal chamber;
   a suction port on the fluid retainer to remove fluid from the tooth chamber, the suction port comprising an opening in the internal chamber;
   an outlet passage extending from the opening to convey the removed fluid from the opening; and
   a vent disposed along the outlet passage and in fluid communication with the suction port with the opening of the suction port being disposed between the internal chamber and the vent, the vent configured to be open to ambient air during a treatment procedure,
   the vent being configured to permit the ambient air to be entrained into flow of fluid removed from the tooth chamber via the suction port without the ambient air entering the tooth chamber, and
   the vent further being configured to inhibit flow of the ambient air into the chamber in the tooth.

2. The apparatus of claim 1, further comprising an inlet line for delivery of fluid to the inlet opening and into the tooth chamber.

3. The apparatus of claim 2, wherein the inlet port communicates with a source of degassed fluid.

4. The apparatus of claim 2, further comprising a housing in fluid connection with the suction port.

5. The apparatus of claim 1, wherein the vent comprises an elongated shape with a ratio of length to width greater than about 1.5 to 1.

6. The apparatus of claim 1, wherein the vent is configured such that pressure of the fluid at an apex of the tooth is less than about 100 mmHg.

7. The apparatus of claim 1 further comprising a plurality of vent openings.

8. The apparatus of claim 1, further comprising a pressure wave generator having a distal portion, the distal portion being configured to be inserted through the fluid retainer into the tooth chamber.

9. The apparatus of claim 8, wherein the pressure wave generator comprises one or more devices selected from the group consisting of: a fluid jet, a laser, a mechanical stirrer, and an ultrasonic device.

10. The apparatus of claim 8, wherein the pressure wave generator is configured to generate pressure waves, and wherein the fluid retainer is configured to retain sufficient fluid within the tooth chamber to permit pressure waves to propagate within the fluid.

11. The apparatus of claim 10, wherein the pressure wave generator is configured to produce sufficient energy to create at least some fluid cavitation within the tooth chamber.

12. The apparatus of claim 8, wherein the fluid retainer comprises a cap.

13. The apparatus of claim 12, wherein the cap is configured to be positioned around the tooth chamber such that the cap substantially closes an access opening into the tooth chamber.

14. The apparatus of claim 13, wherein the cap is configured to be positioned on a tooth seal region of the tooth.

15. The apparatus of claim 14, wherein the cap includes a planar surface that mates to a tooth seal having a planar surface.

16. The apparatus of claim 15, wherein the pressure wave generator is configured to create at least some fluid cavitation in the tooth chamber.

17. The apparatus of claim 16, wherein the fluid retainer is configured to couple with a distal portion of a housing.

18. The apparatus of claim 13, wherein the fluid retainer comprises a flow restrictor configured to be positioned around the tooth chamber and within the cap.

19. The apparatus of claim 13, wherein the cap substantially seals the tooth chamber so as to allow for controlled ingress and egress of fluid.

20. The apparatus of claim 8, wherein the distal portion of the pressure wave generator is configured to be inserted into the opening such that the removed fluid passes through the opening around the pressure wave generator.

21. The apparatus of claim 1, wherein the fluid retainer comprises a flow restrictor.

22. The apparatus of claim 21, wherein the flow restrictor comprises a sponge.

23. The apparatus of claim 1, wherein the fluid retainer is configured to substantially inhibit leakage of fluid, organic material, or both from the tooth chamber except through the suction port.

24. The apparatus of claim 1, wherein the vent is disposed near the suction port.

25. The apparatus of claim 1, wherein the suction port is in continuous, open communication with the vent.

26. The apparatus of claim 1, wherein the vent is angled towards a direction of fluid flow in the outlet passage.

27. The apparatus of claim 1, wherein the vent comprises a lumen having a first end on an outer surface of the apparatus and a second end that joins the outlet passage.

28. The apparatus of claim 1, wherein the vent comprises a vent axis along which air flows and the outlet passage comprises an outlet axis along which the removed fluid flows, wherein an angle between the vent axis and the outlet axis is an acute angle.

29. The apparatus of claim 1, wherein the outlet passage is configured to be in fluid communication with a suction pump that draws fluid away from the fluid retainer.

30. An apparatus for treating a tooth, the apparatus comprising:
   a fluid retainer configured to be positioned against a surface of the tooth to substantially retain fluid in a chamber formed between the fluid retainer and the surface of the tooth;
   an inlet opening to supply fluid to the chamber;
   a suction port on the fluid retainer to remove fluid from the chamber, the suction port comprising an opening in the chamber;
   an outlet passage extending from the opening to convey the removed fluid from the opening; and
   an ambient air vent disposed along the outlet passage and in fluid communication with the suction port with the opening of the suction port being disposed between the chamber and the vent, the vent configured to be open to ambient air during a treatment procedure,
   the vent being configured to permit the ambient air to be entrained into a flow of fluid removed from the chamber via the suction port without the ambient air entering the chamber, and
   the vent further being configured to inhibit flow of the ambient air into the chamber.

31. The apparatus of claim 30, further comprising an inlet line for delivery of fluid to the inlet opening and into the chamber.

32. The apparatus of claim 30, further comprising a pressure wave generator having a distal portion, the distal portion being configured to be inserted through the fluid retainer into the chamber.

33. The apparatus of claim 32, wherein the pressure wave generator comprises one or more devices selected from the group consisting of: a fluid jet, a laser, a mechanical stirrer, and an ultrasonic device.

34. The apparatus of claim 32, wherein the pressure wave generator is configured to generate pressure waves, and wherein the fluid retainer is configured to retain sufficient fluid within the chamber to permit pressure waves to propagate within the fluid.

35. The apparatus of claim 34, wherein the pressure wave generator is configured to produce sufficient energy to create at least some fluid cavitation within the chamber.

36. The apparatus of claim 32, wherein the distal portion of the pressure wave generator is configured to be inserted into the opening such that the removed fluid passes through the opening around the pressure wave generator.

37. The apparatus of claim 30, wherein the fluid retainer comprises a cap.

38. The apparatus of claim 37, wherein the cap substantially seals the chamber so as to allow for controlled ingress and egress of fluid.

39. The apparatus of claim 30, wherein the vent is disposed near the suction port.

40. The apparatus of claim 30, wherein no valves are disposed between the suction port and the vent.

41. The apparatus of claim 30, wherein the vent is angled towards a direction of fluid flow in the outlet passage.

42. The apparatus of claim 30, wherein the vent comprises a lumen having a first end on an outer surface of the apparatus and a second end that joins the outlet passage.

43. The apparatus of claim 30, wherein the vent comprises a vent axis along which air flows and the outlet passage comprises an outlet axis along which the removed fluid flows, wherein an angle between the vent axis and the outlet axis is an acute angle.

44. The apparatus of claim 30, wherein the outlet passage is configured to be in fluid communication with a suction pump that draws fluid away from the fluid retainer.

45. An apparatus for treating a tooth, the apparatus comprising:
a fluid retainer configured to be positioned against a surface of the tooth to substantially retain fluid in a chamber formed between the fluid retainer and the surface of the tooth;
an inlet opening to supply fluid to the chamber;
a suction port on the fluid retainer to remove fluid from the chamber; and
a vent in fluid communication with the suction port, the vent configured to be open to ambient air during a treatment procedure,
the vent being configured to permit the ambient air to be entrained into a flow of fluid removed from the chamber via the suction port without the ambient air entering the chamber, and
the vent further being configured to inhibit flow of the ambient air into the chamber.

46. The apparatus of claim 45, further comprising an inlet line for delivery of fluid to the inlet opening and into the chamber.

47. The apparatus of claim 46, wherein the inlet opening comprises a port configured to cause fluid circulation, agitation, or turbulence in the chamber.

48. The apparatus of claim 45, further comprising a pressure wave generator having a distal portion, the distal portion being configured to be inserted through the fluid retainer into the chamber.

49. The apparatus of claim 48, wherein the pressure wave generator comprises one or more devices selected from the group consisting of: a fluid jet, a laser, a mechanical stirrer, and an ultrasonic device.

50. The apparatus of claim 49, wherein the pressure wave generator comprises a fluid jet.

51. The apparatus of claim 49, wherein the pressure wave generator comprises a laser.

52. The apparatus of claim 48, wherein the pressure wave generator is configured to generate pressure waves, and wherein the fluid retainer is configured to retain sufficient fluid within the chamber to permit pressure waves to propagate within the fluid.

53. The apparatus of claim 52, wherein the pressure wave generator is configured to produce sufficient energy to create at least some fluid cavitation within the chamber.

54. The apparatus of claim 48, wherein the suction port comprises an opening in the chamber, wherein the distal portion of the pressure wave generator is configured to be inserted into the opening such that the removed fluid passes through the opening around the pressure wave generator.

55. The apparatus of claim 45, wherein the fluid retainer comprises a cap.

56. The apparatus of claim 55, wherein the cap substantially seals the chamber so as to allow for controlled ingress and egress of fluid.

57. The apparatus of claim 55, wherein the cap includes a surface that extends beyond at least a portion of an occlusal surface of the tooth.

58. The apparatus of claim 45, wherein the vent is disposed near the suction port such that the fluid flows through the suction port past the vent and such that air outside the apparatus flows through the vent and is entrained into the flow of fluid.

59. The apparatus of claim 45, wherein no valves are disposed between the suction port and the vent.

60. The apparatus of claim 45, further comprising an outlet passage extending from an opening of the suction port to convey removed fluid from the opening, wherein the vent is angled towards a direction of fluid flow in the outlet passage.

61. The apparatus of claim 45, further comprising an outlet passage extending from an opening of the suction port to convey removed fluid from the opening, wherein the vent comprises a lumen having a first end on an outer surface of the apparatus and a second end that joins the outlet passage.

62. The apparatus of claim 45, further comprising an outlet passage extending from an opening of the suction port to convey removed fluid from the opening, wherein the vent comprises a vent axis along which air flows and the outlet passage comprises an outlet axis along which the removed fluid flows, wherein an angle between the vent axis and the outlet axis is an acute angle.

63. The apparatus of claim 45, further comprising an outlet passage extending from an opening of the suction port to convey removed fluid from the opening, wherein the outlet passage is configured to be in fluid communication with a suction pump that draws fluid away from the fluid retainer.

64. The apparatus of claim 45, further comprising a pump to be in communication with the fluid retainer to supply fluid to the chamber;
a motor to drive the pump; and
a controller configured to control the operation of the motor, the pump, or both.

65. The apparatus of claim 64, further comprising a reservoir, the pump moving degassed liquid from the reservoir through the fluid retainer and into the chamber.

66. The apparatus of claim 45, further comprising a degassing system to provide degassed liquid to the fluid retainer.

67. The apparatus of claim 66, wherein the degassing system provides degassed liquid that is free of dissolved gases to less than 0.1% by volume.

68. The apparatus of claim 66, further comprising a mixing system to mix fluids supplied to the fluid retainer.

69. The apparatus of claim 68, wherein the mixing system is downstream of the degassing system, the mixing system configured to mix degassed liquids.

70. The apparatus of claim 45, further comprising a tooth monitoring system to monitor progress of a treatment procedure.

71. The apparatus of claim 45, further comprising a guide tube that supplies liquid to the chamber, the guide tube comprising an impingement plate at a distal end of the guide tube.

\* \* \* \* \*